(12) United States Patent
Pausch et al.

(10) Patent No.: US 6,607,906 B1
(45) Date of Patent: Aug. 19, 2003

(54) HETEROLOGOUS G PROTEIN COUPLED RECEPTORS EXPRESSED IN YEAST, THEIR FUSION WITH G PROTEINS AND USE THEREOF IN BIOASSAY

(75) Inventors: Mark Henry Pausch, Robbinsville, NJ (US); Bradley Alton Ozenberger, Yardley, PA (US); John Richard Hadcock, Mount Holly, NJ (US); Laura Alicia Price, Langhorne, PA (US); Eileen Marie Kajkowski, Ringoes, NJ (US); Donald Richard Kirsch, Princeton, NJ (US); Deborah Tardy Chaleff, Pennington, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/057,473

(22) Filed: Apr. 9, 1998

Related U.S. Application Data

(63) Continuation of application No. 08/696,924, filed as application No. PCT/US95/02075 on Feb. 14, 1995, now Pat. No. 6,406,871, which is a continuation-in-part of application No. 08/195,729, filed on Feb. 14, 1994, now Pat. No. 5,091,188.

(51) Int. Cl.$^7$ .................. G01N 33/569; G01N 33/566; C12N 1/20; C12N 1/15

(52) U.S. Cl. ................ 435/254.11; 435/7.31; 435/69.7; 435/69.5; 435/254.2; 435/254.21; 435/320.1; 436/501; 536/23.5; 530/350

(58) Field of Search ............... 435/254.11, 254.2, 435/254.21, 69.1, 7.31, 69.7; 436/501; 530/350; 536/23.5

(56) References Cited

U.S. PATENT DOCUMENTS

| | | | |
|---|---|---|---|
| 5,284,746 A | * 2/1994 | Sledziewski et al. ......... 435/6 |
| 5,401,629 A | 3/1995 | Harpold et al. |
| 5,482,835 A | 1/1996 | King et al. |
| 5,576,210 A | 11/1996 | Sledziewski |
| 5,691,188 A | * 11/1997 | Pausch et al. ................. 435/6 |
| 5,739,029 A | 4/1998 | King et al. |
| 5,789,184 A | 8/1998 | Fowlkes et al. |
| 6,100,042 A | * 8/2000 | Fowlkes et al. ............. 435/7.1 |

FOREIGN PATENT DOCUMENTS

| | | |
|---|---|---|
| WO | WO 91/12273 | 2/1991 |
| WO | WO 92/05244 | 9/1991 |
| WO | WO 94/23025 | 10/1994 |

OTHER PUBLICATIONS

Anderson, JA et al. Functional expression of a probable *Arabidopsis thaliana* potassium channel in *S. cerevisiae*. Proc. Natl. Acad. Sci. USA 89(3736–3740), 92, May 1992.*

Chang, F. and Herskowitz I. Identification of a gene necessary for cell cycle arrest by a negative growth factor of yeast: FAR1 is an inhibitor of G1 cyclin, CLN2. Cell 63(999–1011)92, Nov. 1999.*

Doi, K. et al. MSG5, a novel protein phosphatase promotes adaptation to pheromone response in *S. cerevisiae*. EMBO J. 13:1(61–70)94, 1994.*

Feinstein, PG et al. Molecular cloning and characterization of a Ca/calmodulin insensitive adenylyl cyclase from rat brain. Proc. Natl. Acad. Sci. USA 88(10173–10177), Nov. 1991.*

Kang, Y–S et al. Effects of expression of mamalian G–alpha and hybrid mammalian –yeast G–alpha proteins on the yeast pheromone response signal transduction pathway. Mol. Cell. Biol. 10:6(2582–2590)90, Jun. 1990.*

King K. et al. Control of yeast mating signal transduction by a mammalian Beta–2–adrenergic receptor and Gs–alpha subunit. Science 250(121–123)90, Oct. 1990.*

Kubo Y. et al. Primary structure and functional expression of a rat G–protein–coupled muscarinic potassium channel. Nature 364(802–806)93, Aug. 1993.*

Leberer, E. et al. Molecular characterization of SIG1, a *S. cerevisiae* gene involved in negative regulation of G–protein–mediated signal transduction. EMBO J. 13(3050–3064)1994.*

Sprague, GF and Thorner, JW. Pheromone response and signal transduction during the mating process of *S. cerevisiae*. The Molecular and Cellular Biology of the Yeast Saccharomyces: Gene Expression, Cold Spring Harbor Laboratory Press, 1992.*

Yoko–O, T. et al. The putative phosphoinostitde–specific phospholipase C gene, PLC1, of the yeast *S. cerevisiae* is important for cell growth. Proc. Natl. Acad. Sci. USA 90(1804–1808)93, Mar. 1993.*

Suh, P–G et al. Cloning and sequence of multiple forms of phospholipase C Cell 54(161–169)Jul. 1988.*

Watson, S. and Arkinstall, The G–Protein Linked Receptor Facts Book, Academic Press, London, 1994.*

(List continued on next page.)

*Primary Examiner*—Yvonne Eyler
*Assistant Examiner*—Michael Brannock
(74) *Attorney, Agent, or Firm*—Finnegan, Henderson, Farabow, Garrett & Dunner, L.L.P.

(57) ABSTRACT

A first aspect of the present invention is directed to a transformed yeast cell containing a first heterologous DNA sequence which codes for a G protein-coupled receptor, for example, the somatostatin receptor, and a second heterologous DNA sequence which codes for a G protein a subunit or portions thereof fused to DNA sequences from the yeast G protein in a subunit. A second aspect of the present invention is a transformed yeast cell containing a heterologous DNA sequence which codes for a G protein coupled receptor. A third aspect of the present invention is a method of assaying compounds to determine effects on cell growth.

70 Claims, 28 Drawing Sheets

OTHER PUBLICATIONS

Dohlman et al., "Model Systems for the Study of Seven–Transmembrane–Segment Receptors," 60:653–688, Ann. Rev. Biochem., 1991.

Sprague et al., "Pheromone Response and Signal Transduction during the Mating Process of *Saccharomyces cerevisiae*," 1992, Cold Spring Harbor, pp. 657–743.

Press Release: "Cadus Receives Composition of Matter Patent and Notices of Allowance for Two U.S. Patent Applications on Its Core Yeast Technology," Cadus Pharmaceutical Corporation, Tarrytown, New York, Apr. 14, 1998.

W.C. Probst, L.A. Snyder, D.I. Schuster, J. Brosius, S.C. Sealfron, "Sequence Alignment of the G Protein–Coupled Receptor Superfamily, DNA and Cell Biology," vol. II, No. 1, 1992, pp. 1–20.

Klim King, Henrik G. Dohlman, Jeremy Thorner, Marc G. Caron, Robert J. Lefkowitz, "Control of Yeast Mating Signal Transduction by a Mammalian $\beta$2–Adrenergic Receptor and G $\alpha$ Subunit," Science, vol. 250, pp. 121–123, 1990.

Ira Herskowitz and Lorraine Marsh, "Conservation of a Receptor/Signal Transduction System," Cell, vol. 50, 995–996, Sep. 25, 1987.

Stafano Marullo, Collette Delavier–Klutchko, Jean–Gérard Guillet, Alain Charbit, Arthur Donny Strosberg and Laurent Jean Emorine, "Expression of Human $\beta$1 and $\beta$2 Adrenergic Receptors in *E. coli* as a New Tool for Ligand Screening," Bio/Technology, vol. 7, Sep. 1989, pp. 923–927.

Gretchen McCaffrey, Fiona J. Clay, Kimberly Kelsay and George F. Sprague, Jr., "Identification and Regulation of a Gene Required for Cell Fusion during Mating of the Yeast *Saccharomyces cerevisiae*," Molecular and Cellular Biology, vol. 7, Nov. 8, 1987, pp. 2680–2690.

Joshua Trueheart, Jef D. Boeke, and Gerald R. Fink, "Two Genes Required for Cell Fusion during Yeast Conjugation: Evidence for a Pheromone–Induced Surface Protein," Molecular and Cellular Biology, Jul. 1987, pp. 2316–2328.

J.W. Kronstad, J.A. Holly, and V.L. MacKay, "A Yeast Operator Overlaps an Upstream Activation Site," Cell, vol. 50, 369–377, 1987.

\* cited by examiner

|  |  | Bmax (pmol/mg) |
|---|---|---|
| CHI11 |  | 3.1 |
| CHI17 |  | 1.6 |
| CHI18 |  | 0.7 |

FIG. 26A
FIG. 26B
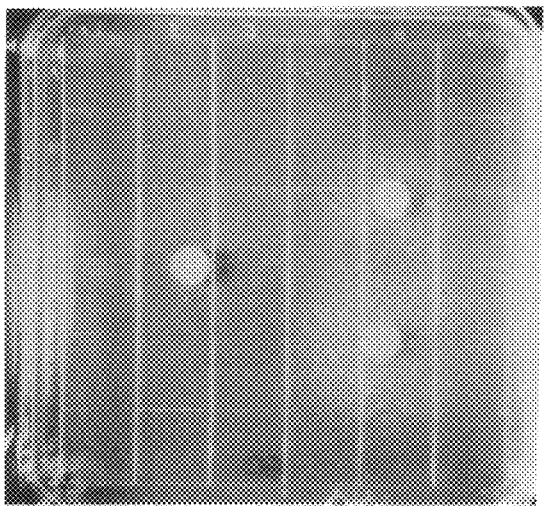
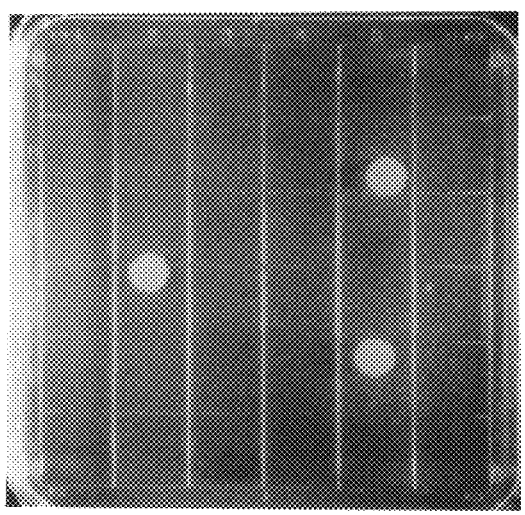

CL compounds (10 μl of 10 mg/ml solution) applied to each position.

CL compounds (10 μl of 10 mg/ml solution) applied to each position.

FIG. 28A
FIG. 28B
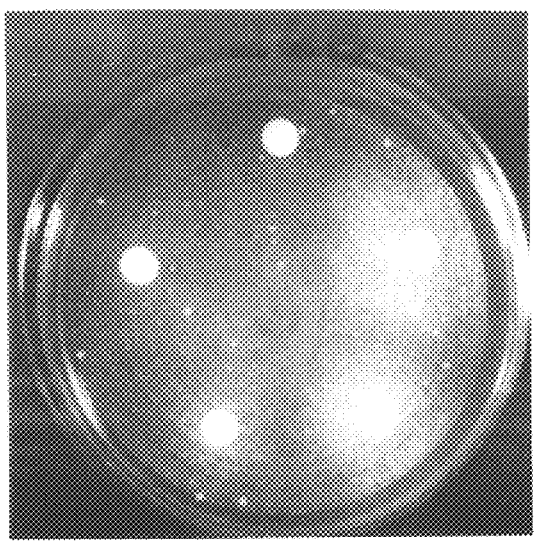
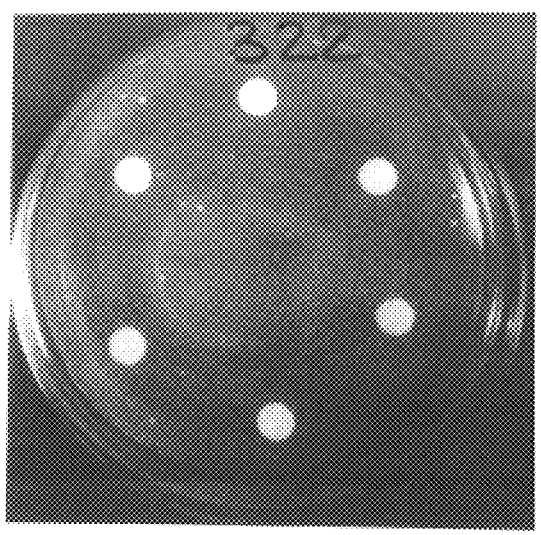

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:1:

AAAAGATCTA AAATGGACCT GCTCAAGCTG                                        30

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:2:

AAAAGATCTT CAGCCAGGCC CCAGTGTGCT                                        30

(2) INFORMATION FOR SEQ ID NO:3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:3:

GAAGATCTAA AAAATGGGCT CCTCGGTGTA C                                      31

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:4:

ACATGCATGC AGATCTTCAG GAAGGGGCAA ACTC                                34

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

TTTCTCGAGC GAATTTCTTA TGATTT                                                26

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:6:

TTTGGTACCG GGCCCGGACG GATTACAACA GGT                                  33

-continued (2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:7:

GGGAGCTCTG ATGGTGGTAC ATAACG                                    26

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:8:

GGGGGATCCT GTATATGAGA TAGTTGA                                   27

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:9:

AAAGATCTAA AATGGGCTCC TCGGTGTAC                                29

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:10:

AAGTCGACTC AGGAAGGGGC AAACTC                                    26

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:11:

AAAAAGATCT AAAATGGAGC CCCTCTCTCT G                            31

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:12:

AGCAGATCTT CAGATCCCAG AAGACAAC                                28

(2) INFORMATION FOR SEQ ID NO:13:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:13:

AAAAGATCTA AAATGTCCAT TCCATTTGAC                               30

(2) INFORMATION FOR SEQ ID NO:14:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (xi) SEQUENCE DESCRIPTION: SEQ ID NO:14:

AAAAGGTACC AGATCTTCAG ATACTGGTTT GGAG                          34

(2) INFORMATION FOR SEQ ID NO:15:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO:15:

ATAGGATCCA AAATGGACCG CCGGATGTGG GGG                           33

(2) INFORMATION FOR SEQ ID NO:16:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (xi) SEQUENCE DESCRIPTION: SEQ ID NO:16:

ATATGGATCC CTAGCACATA GATGTCAG                                 28

(2) INFORMATION FOR SEQ ID NO:17:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (xi) SEQUENCE DESCRIPTION: SEQ ID NO:17:

GTCGACAAAT CAGATGGAGG ACGGTAAACA GG                            32

(2) INFORMATION FOR SEQ ID NO:18:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (iv) ANTI-SENSE: YES (xi) SEQUENCE DESCRIPTION: SEQ ID NO:18:

GAGCTCATTA GAGTCTTCCA CCGGGGG                                  27

HETEROLOGOUS G PROTEIN COUPLED RECEPTORS EXPRESSED IN YEAST, THEIR FUSION WITH G PROTEINS AND USE THEREOF IN BIOASSAY

This is a continuation of U.S. patent application Ser. No. 08/696 924, filed Oct. 15, 1996, now U.S. Pat. No. 6,406, 871, which is an application under 35 U.S.C. § 371 of PCT/US95/02075, filed Feb. 14, 1995, which is a continuation-in-part application of U.S. patent application Ser. No. 08/195,729, filed Feb. 14, 1994, now U.S. Pat. No. 5,091,188—all of which are incorporated herein by reference.

FIELD OF THE INVENTION

This invention relates to heterologous G protein-coupled receptor expression constructs, yeast cells expressing such receptors, vectors useful for making such cells, and methods of making and using same.

BACKGROUND OF THE INVENTION

The actions of many extracellular signals, for example: neurotransmitters, hormones, odorants and light, are mediated by receptors with seven transmembrane domains (G protein-coupled receptors) and heterotrimeric guanine nucleotide-binding regulatory proteins (G proteins). G proteins are comprised of three subunits: a guanyl-nucleotide binding $\alpha$ subunit; a $\beta$ subunit; and a Y subunit [for review, see Conklin, B. R and Bourne, H. R. (1993 Cell 73, 631–641]. G proteins cycle between two forms, depending on whether GDP or GTP is bound to the a subunit. When GDP is bound, the G protein exists as a heterotrimer, the G$\alpha\beta$Ycomplex. When GTP is bound, the a subunit disassociates, leaving a G$\beta$Y complex. Importantly, when a G$\alpha\beta$Y complex operatively associates with an activated G protein coupled receptor in a cell membrane, the rate of exchange of GTP for bound GDP is increased and, hence, the rate of disassociation of the bound G$\alpha$ subunit from the G$\beta$Y complex increases. The free G$\alpha$ subunit and G$\beta$Y complex are capable of transmitting a signal to downstream elements of a variety of signal transduction pathways. This fundamental scheme of events forms the basis for a multiplicity of different cell signaling phenomena. For a review, see H. G. Dohlman, J. Thorner, M. Caron, and R. J. Lefkowitz, Ann. Rev. Biochem, 60, 653–688 (1991). G protein-mediated signaling systems are present in organisms as divergent as yeast and man. The yeast *Saccharomyces cerevisiae* is utilized as a model eukaryotic organism. Due to the ease with which one can manipulate the genetic constitution of the yeast *Saccharomyces cerevisiae*, researchers have developed a detailed understanding of many complex biological pathways. It has been demonstrated in numerous systems that the evolutionary conservation of protein structure is such that many heterologous proteins can substitute for their yeast equivalents. For example, mammalian G$\alpha$ proteins can form heterotrimeric complexes with yeast G$\beta$Y proteins [Kang, Y. S., Kane, J., Kurjan, J., Stadel, J. M., and Tipper, D. J. (1990) Mol. Cell. Biol. 10, 2582–2590). The G protein coupled receptors represent important targets for new therapeutic drugs. Discovery of such drugs will necessarily require screening assays of high specificity and throughput. For example, therapeutic intervention in the somatostatin growth hormone axis requires new chemical agents that act in a somatostatin receptor subtype-selective manner. The somatostatin receptor (SSTR) is a prototype of the seven transmembrane-domain class of receptors in mammalian cells. The cyclic tetradecapeptide somatostatin, first isolated from hypothalamus and shown to be a potent inhibitor of growth hormone release from the anterior pituitary, has been shown to have broad modulatory effects in CNS and peripheral tissues. In response to binding of somatostatin, SSTR activates a heterotrimeric G protein, which in turn modifies the activity of a variety of effector proteins including but not limited to adenylate cyclases, ion channels, and phospholipases. The effects of somatostatin are transduced through the action of gene products encoded in five distinct receptor subtypes that have recently been cloned [Strnad, J., Eppler, C. M., Corbett, M., and Hadcock, J. R. (1993) BBRC 191, 968–976; Yamada, Y., Post, S. R., Wang, K., Tager, H. S., Bell, G. I., and Seino, S. (1992) Proc. Natl. Acad. Sci. USA 89, 251–255; Meyerhof, W., Paust, H. J., Schonrock, C., and Richter, D. (1991); Kluxen, F. W., Bruns, C., and Lubbert, H. (1992) Proc. Natl. Acad. Sci. USA 89, 4618–4622; Li, X. J., Forte, M., North, R. A., Rose, C. A., and Snyder, S. (1992) J. Biol. Chem. 267, 21307–21312); Bruno, J. F., Xu, Y., Song, J., and Berelowitz, M. (1992) Proc. Natl. Acad. Sci. USA 89, 11151–11154; O'Carrol, A. M., Lolait, S. J., Konig, M., and Mahan, L. (1992) Mol. Pharmocol. 42, 939–946]. Screening assays utilizing yeast strains genetically modified to accommodate functional expression of the G protein-coupled receptors offer significant advantages in research involving ligand binding to the somatostatin receptor, as well as a host of other receptors implicated in various disease states.

SUMMARY OF THE INVENTION

A first aspect of the present invention is directed to expression vectors and yeast cells transformed therewith, containing a first heterologous nucleotide sequence which encodes for a G protein-coupled receptor, for example, the somatostatin receptor, and a second nucleotide sequence which encodes for all or a portion of a G protein $\alpha\beta$Y complex. In certain embodiments, all or a portion of a nucleotide sequence encoding for a heterologous G protein a subunit is fused to a nucleotide sequence from the yeast G protein a subunit. In certain preferred embodiments, the expression vectors and transformed cells contain a third heterologous nucleotide sequence comprising a pheromone-responsive promotor and an indicator gene positioned downstream from the pheromone-responsive promoter and operatively associated therewith. The vectors and cells may further contain several mutations. These include 1) a mutation of the yeast SCGl/GPAl gene, which inactivates the yeast G$\alpha$ protein, facilitating interaction of the heterologous receptor with the G protein; 2) a mutation of a yeast gene to inactivate its function and enable the yeast cell to continue growing in spite of activation of the pheromone response signal transduction pathway, preferred embodiments being mutations of the FAR1 and/or FUS3 genes; and, 3) a mutation of a yeast gene, the effect of the which is to greatly increase the sensitivity of the response of the cell to receptor-dependent activation of the pheromone response signal transduction pathway, preferred genes in this regard being the SST2, STE50, SGV1, STE2, STE3, PIKI, AFRI, MSG5, and SIG1 genes.

A second aspect of the present invention is a chimeric expression construct and yeast cells transformed therewith comprising a first nucleotide sequence encoding for a yeast G protein coupled receptor in operative association with a heterologous nucleotide sequence which encodes for a heterologous G protein coupled receptor. The constructs and cells may contain a second heterologous nucleotide sequence comprising a pheromone-responsive promoter and an indicator gene positioned downstream from the pheromone-responsive promoter and operatively associated therewith. The constructs and cells may further contain several mutations. These include 1) a mutation of a yeast gene to inactivate its function and enable the yeast cell to continue growing in spite of activation of the pheromone response signal transduction pathway, preferred embodiments being mutations of the FAR1 and/or FUS3 genes; and, 2) a mutation of a yeast gene, the effect of the which is to greatly increase the sensitivity of the response of the cell to receptor-dependent activation of the pheromone response signal transduction pathway, preferred genes in this regard being the SST2, STE50, SGV1, STE2, STE3, PIKL, AFRI, MSG5, and SIGI genes. A productive signal is detected in a bioassay through coupling of the heterologous receptor to a yeast protein.

A third aspect of the present invention is a method of assaying compounds to determine effects of ligand binding to the heterologous receptors by measuring effects on cell growth. In certain preferred embodiments, yeast cells of the kind described above are cultured in appropriate growth medium to cause expression of heterologous proteins, embedded in agar growth medium, and exposed to compounds applied to the surface of the agar plates. Effects on the growth of embedded cells are expected around compounds that activate the heterologous receptor. Increased growth may be observed with compounds that act as agonists, while decreased growth may be observed with those that act as antagonists.

BRIEF DESCRIPTION OF THE DRAWINGS

FIG. 26 (A&B). Effect of STE50 overexpression on SSTR2 bioassay. Assay medium and yeast strains were prepared as described in Materials and Methods. Plate A contains the STE50 overexpression strain CY560; plate B contains the control strain CY562. Filter discs saturated with solutions of the following peptides were applied to each plate: 1 mM yeast a pheromone (lefthand center), 1 µg/ml somatostatin-14 (righthand top), 100 µg/ml somatostatin-14 (righthand bottom). Plates were incubated at 30° C. for 3 days.

FIG. 28 (A&B) Fusion of STE2 sequences to the amino terminal of SSTR2 reduces signaling effeciency in response to somatostatin. LY268 and LY322 cells were plated in SC Galactose (2%)-ura, trp, his agar medium (2×10$^4$ cell/ml). Sterile filter disks were placed on the surface of the solidified agar and saturated with 10 µl of somatostatin (S-14). The plates were then incubated at 30° C. for 3 days. (A) LY268. S-14 was applied to filter disks clockwise from the top: carrier, 60 =mol, 6 nmol, 600 pmol, 60 pmol, 6 pmol. (B) LY322. S-14 was applied to filter disks clockwise from the top: 0.6 pmol, carrier, 60 =nmol, 6 =mol, 600 pmol, 60 pmol, 6 pmol.

DETAILED DESCRIPTION OF THE INVENTION

Detailed Description of the Invention

Figure 1:
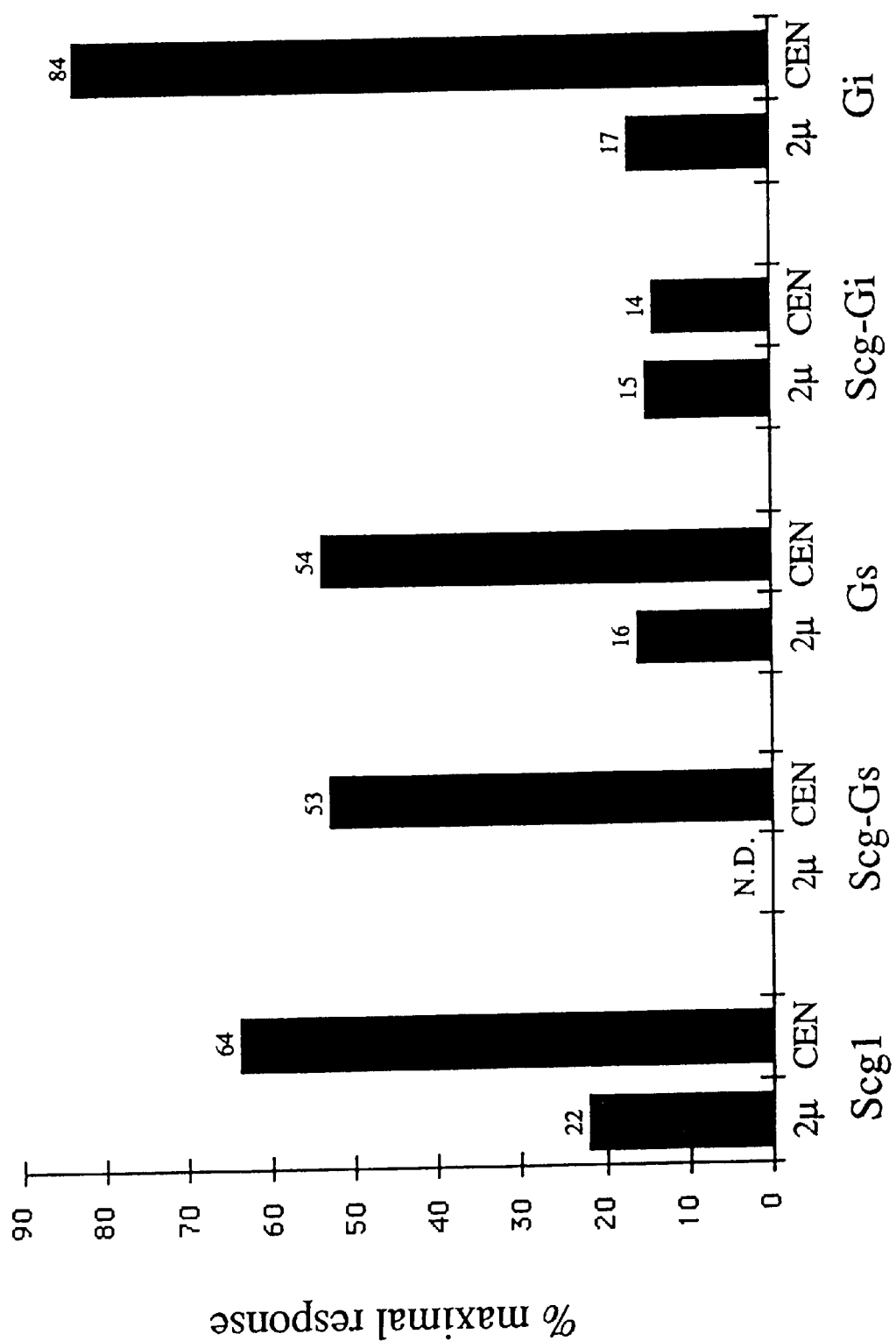
FIG. 1 Strains containing the indicated Gα expression plasmids are treated with mating pheromone (α factor). A measure of resulting signal transduction is provided by a reporter plasmid carrying FUS1-lacZ. Data are represented as a percent of β-galactosidase activity measured in a strain expressing solely the wild type Go protein.

Nucleotide bases are abbreviated herein as follows:

A-Adenine  G-Guanine
C-Cytosine  T-Thymine
U-Uracil (sometimes herein abbreviated as "ura")

-continued

Detailed Description of the Invention

Amino acid residues are abbreviated herein to either three letters or a single letter as follows:

| | |
|---|---|
| Ala;A-Alanine | Leu;L-Leucine |
| Arg;R-Arginine | Lys;K-Lysine |
| Asn;N-Asparagine | Met;M-Methionine |
| Asp;D-Aspartic acid | Phe;F-Phenylalanine |
| Cys;C-Cysteine | Pro;P-Proline |
| Gln;Q-Glutamine | Ser;S-Serine |
| Glu;E-Glutamic acid | Thr;T-Threonine |
| Gly;G-Glycine | Trp;W-Tryptophan |
| His;H-Histidine | Tyr;Y-Tyrosine |
| Ile;I-Isoleucine | Val;V-Valine |

The terms "DNA" and "nucleotide sequence" are used interchangably and are meant to include all forms of linear polymers comprising nucleotide bases, without limitation, including RNA when appropriate.

The term "mammalian" as used herein refers to any mammalian species (e.g. human, mouse, rat, and monkey).

The term "heterologous" is used herein with respect to yeast, and hence refers to DNA sequences, proteins, and other materials originating from organisms other than yeast (e.g., mammalian, avian, amphibian, insect, plant), or combinations thereof not naturally found in yeast.

The term "upstream" and "downstream" are used herein to refer to the direction of transcription and translation, with a sequence being transcribed or translated prior to another sequence being referred to as "upstream" of the latter.

Any G protein-coupled receptor, or portions thereof, as well as the nucleotide sequences encoding same, may be employed in practicing the present invention, Examples of such receptors include, but are not limited to, adenosine receptors, somatostatin receptors, dopamine receptors, cholecystokinin receptors, muscarinic cholinergic receptors, α-adrenergic receptors, β-adrenergic receptors, opiate receptors, cannabinoid receptors, growth hormone releasing factor, glucagon, and serotonin receptors. The term receptor as used herein is intended to encompass subtypes of the named receptors, and mutants and homologs hereof, along with the nucleotide sequences encoding same. One skilled in the art will also understand that in some instances, it may not be necessary that the entire receptor be expressed to achieve the purposes desired. Accordingly, the term receptor is meant to include truncated and other variant forms of a given receptor, without limitation.

Any DNA sequence which codes for a Gα subunit (Gα) may be used to practice the present invention. Examples of Gα subunits include, but are not limited to Gs subunits, Gi subunits, Go subunits, Gz subunits, Gq, G11, G16 and transducing subunits. G proteins and subunits useful for practicing the present invention include subtypes, and mutants and homologs thereof, along with the DNA sequences encoding same.

One skilled in the art will understand from the teachings as presented herein that the G proteins useful in the constructs and yeast cells of the present invention may comprise heterologous Gα subunits, yeast Gα subunits, or chimeric yeast/heterologous versions. One can easily determine which configuration is best suited for adequate coupling to a particular heterologous receptor by simply constructing vectors as taught herein and measuring the signaling of ligand binding in response to a given assay. In certain preferred embodiments, $G\alpha_{12}$ is the Gα subunit of choice, particularly when the heterologous G coupled protein is all or a portion of a somatostatin receptor. It is particularly preferred in this instance that the $G\alpha_{12}$ subunit be coupled to a yeast GβY complex. Certain chimeric constructs may also provide enhanced signal transduction with regard to particular heterologous receptors. Particularly preferred is a chimeric construct formed from fusion of the amino terminal domain of yeast GPA1/SCG1 with the carboxy terminal domain of a heterologous Ga,, Ga,, and especially $G\alpha_{12}$.

Any DNA sequence which codes for a GβY subunit (GβY) may be used to practice the present invention. G proteins and subunits useful for practicing the present invention include subtypes, and mutants and homologs thereof, along with the DNA sequences encoding same. The host cells may express endogenous GβY, or may optionally be engineered to express heterologous GβY (e.g., mammalian) in the same manner as they would be engineered to express heterologous Gα.

Heterologous DNA sequences are expressed in a host by means of an expression "construct" or "vector". An expression vector is a replicable DNA construct in which a DNA sequence encoding the heterologous DNA sequence is operably linked to suitable control sequences capable of affecting the expression of a protein or protein subunit coded for by the heterologous DNA sequence in the intended host. Generally, eukaryotic control sequences include a transcriptional promoter, however, it may be appropriate that a sequence encoding suitable mRNA ribosomal binding sites be provided, and (optionally) sequences which control the termination of transcription. Vectors useful for practicing the present invention include plasmids, viruses (including bacteriophage), and integratable DNA fragments (i.e., fragments integratable into the host genome by genetic recombination). The vector may replicate and function independently of the host genome, as in the case of a plasmid, or may integrate into the genome itself, as in the case of an integratable DNA fragment. Suitable vectors_ will contain replicon and control sequences which are derived from species compatible with the intended expression host. For example, a promoter operable in a host cell is one which binds the RNA polymerase of that cell, and a ribosomal binding site operable in a host cell is one which binds the endogenous ribosomes of that cell.

DNA regions are operably associated when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells of the present invention are cells which have been transformed or transfected with the vectors constructed using recombinant DNA techniques and express the protein or protein subunit coded for by the heterologous DNA sequences. A variety of yeast cultures, and suitable expression vectors for transforming yeast cells, are known. See e.g., U.S. Pat. Nos. 4,745,057; 4,797,359; 4,615,974; 4,880,734; 4,711,844; and 4,865,989. *Saccharomyces cerevisiae* is the most commonly used among the yeasts, although a number of other yeast species are commonly available. See. e.g., U.S. Pat. No. 4,806,472 (*Kluveromyces lactis* and expression vectors therefore); U.S. Pat. No. 4,855,231 (*Pichia pastoris* and expression vectors therefore). Yeast vectors may contain an origin of replication from the endogenous 2 micron yeast plasmid or an autonomously replicating sequence (ARS) which confers on the plasmid the ability to replicate at high copy number in the yeast cell, centromeric (CEN) sequences which limit the ability of the plasmid to replicate at only low copy number in the yeast cell, a promoter, DNA encoding the heterologous DNA sequences, sequences for polyadenylation and transcription termination, and a selectable marker gene. Exemplary plasmids and detailed of materials and methods for making and using same are provided in the Examples section.

Any promoter capable of functioning in yeast systems may be selected for use in the constructs and cells of the present invention. Suitable promoting sequences in yeast vectors include the promoters for metallothionein, 3-phosphoglycerate kinase (PGK) [Hitzeman et al., (1980) J.Biol. Chem. 255, 2073] or other glycolytic enzymes [(Hess et al., (1968) J. Adv. Enzyme Reg. 7, 149]; and Holland et al., (1978) Biochemistry 17, 4900], such as enolase, glyceraldehyde-3-phosphate dehydrogenase, hexokinase, pyruvate, decarboxylase,phosphofructokinase, glucose-6-phosphate isomerase, 3- phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase, 1,2,-isocytochrome C, acid phosphates, degradative enzymes associated with nitrogen metabolism, and the aforementioned metallothionein and glyceraldehyde-3-phosphate dehydrogenase, as well as enzymes responsible for maltose and galactose utilization, such as the galactose inducible promoter, GAL1. Particularly preferred for use herein are the PGK, GAL1, and alcohol dehydrogenase (ADH) promoters. Finally, in constructing suitable expression plasmids, the termination sequences associated with these genes may also be ligated into the expression vector 3' of the heterologous coding sequences to provide polyadenylation and termination of the mRNA. In preparing the preferred expression vectors of the present invention, translational initiation sites are chosen to confer the most efficient expression of a given nucleic acid sequence in the yeast cell (see Cigan, M. and T. F. Donahue 1987, GENE, Volume 59, pp. 1–18, for a description of suitable translational initiation sites].

A particularly preferred nucleotide expression vector useful for carrying out the present invention comprises such an aforementioned promoter sequence, positioned upstream to the translational initiation site of the heterologous nucleotide sequence encoding for the heterologous G protein coupled receptor it is desired to express, and in correct reading frame therewith. Particularly preferred promoters in this regard are the GAL1, PGK, and ADH promoters. Positioning of the aforementioned promotor upstream to the chosen translational initiation site may enhance expression of a heterologous protein. In these preferred embodiments, no yeast G protein coupled receptor segment is fused to the heterologous G protein coupled receptor segment. The present inventors have discovered that such hybrid receptors are not critical to achieve receptor expression in yeast. This is contrary to the art accepted teaching in this regard [see King, et al. cited infra).

In certain other embodiments however, at least a fragment of the 5'-untranslated region of a yeast gene is positioned upstream from the heterologous G protein coupled segment and operatively associated therewith. To that end, the present invention also provides constructs having suitable promoters and translational initiation sites as described above, but these constructs include a yeast segment comprising at least a fragment of the extreme amino-terminal coding nucleotide sequence of a yeast G protein-coupled receptor and a second segment downstream from said first segment and in correct reading frame therewith, the second segment comprising a nucleotide sequence encoding a heterologous G protein-coupled receptor. The yeast segment in this regard may be provided to actually act as a reporter sequence, rather than to serve to enhance effective expression of the heterologous G protein in the yeast system. Thus, certain embodiments comprise a gene sequence encoding a yeast segment of a yeast G protein-coupled receptor, that acts as a reporter segment, in that it encodes a peptide that may be detected through conventional means, such as antibody binding, and the like. Preferred in this regard is all or a portion of a yeast pheromone receptor fused to a heterologous G protein coupled receptor, which may be used primarily as an "epitope tag" for the highly specific detection of expression of the desired heterologous receptor using antibodies directed specifically to the epitope sequence expressed. In constructing such a vector, the yeast segment may be positioned upstream to the heterologous protein, or alternatively, a fragment of the extreme amino-terminal coding sequence of the heterologous G protein-coupled receptor may be deleted, and the yeast segment fused directly thereto. In some cases, one or more of the amino terminal transmembrane domains or intracellular domains of the heterologous protein are deleted. Alternatively, the yeast segment may be added directly to the amino terminus of the heterologous receptor, thereby elongating the overall chimeric receptor construct.

The first and second segments are operatively associated with a promoter, such as the GALL promoter, which is operative in a yeast cell. Coding sequences for yeast G protein-coupled receptors which may be used in constructing such vectors are exemplified by the gene sequences encoding yeast pheromone receptors (e.g., the STE2 gene, which encodes the a-factor receptor, and the STE3 gene, which encodes the a-factor receptor).

Certain preferred chimeric receptors provided herein comprise a yeast Ste2 protein segment fused directly to all or a portion of a heterologous G protein receptor, and preferably, the 5HT1a receptor, muscarinic receptor, α-adrenergic receptor, or a somatostatin receptor.

Any of a variety of means for detecting the effects of ligand binding can be utilized. For example, measurement of the disassociation of Gα from GβY can be made through conventional biochemical techniques. However, it should be noted that the binding of ligand to a receptor may either trigger or block a detectable biological response, which may also lend itself to measurement. One such biological response is the ability of yeast cells to mate. Use of the pheromone induced mating signal transduction pathway is a preferred method of detecting the effects of ligand binding in the assay systems herein presented, the basic premise of which is discussed in more detail, as follows.

G protein-coupled pheromone receptors in yeast control a developmental program that culminates in mating (fusion) of a and α haploid cell types to form the a/αdiploid (for a review, see G. F. Sprague, Jr. and J. W. Thorner, in the Molecular Biology and Cellular Biology of the Yeast Saccharomyces: volume II, Gene Expression). The process of mating is initiated by extracellular peptides, the mating pheromones. Cells of the a mating type secrete α-factor, which elicits a response in a-cells; cells of the α-mating type secrete α-factor which acts only on a cells. Haploid cells respond to the presence of the peptide mating pheromones through the action of endogenous G protein-coupled pheromone receptors (STE2: the α-factor receptor, expressed only in a cells and STE3: the a-factor receptor expressed only in a-cells). Both receptors interact with the same heterotrimeric G proteins and a signal transduction cascade that is common to both haploid cell types. Upon pheromone-binding to receptor, the receptor presumably undergoes a conformational change leading to activation of the G protein. The α-subunit, SCG1/GPA1, exerts a negative effect on the pheromone response pathway, which is relieved by receptor-dependent activation. The complex of βY subunits (STE4, STE18) is thought to transmit the positive signal to an effector, possibly STE20, a putative protein kinase [Leberer, E., Dignard, D., Harcus, D., Thomas, D. Y., Whiteway, M. (1992) EMBO J. 11, 4815–4824]. The effector in turn activates downstream elements of the signal transduction pathway which include STE5, and a presumptive protein kinase cascade composed of the products of the STE11, STE7, FUS3 and KSS1 genes, eventually resulting in cell cycle arrest and transcription induction. The primary interface between elements of the pheromone response pathway and cell cycle regulatory machinery is the FAR1 gene product. Certain recessive alleles of FAR1 and FUS3 fail to undergo cell cycle arrest in response to pheromone, while permitting pheromone dependent transcription to occur. Pheromone-dependent transcription is mediated through the action of the sequence-specific DNA-binding protein STE12. Activation of STE12 results in transcription of genes possessing a cis-acting DNA sequence, the pheromone response element. These pheromone responsive genes encode products that are required for pheromone synthesis (MFa1, MFa2, MFA1, MFA2, STE6, STE13) and the response to pheromone (STE2, STE3, SCG1/GPA1, FUS3), facilitate or participate in cell association and fusion (FUS1), cell cycle arrest (FAR1) , and the morphological events required for mating. In the event that the mating process is not consummated, yeast cells become adapted to the presence of pheromone and resume mitotic growth. Thus, in certain preferred embodiments, the FUS3 or FAR1 gene is mutated or deleted altogether, thereby disconnecting the cell cycle arrest pathway from the signal transduction pathway, and allowing continued growth of the cells in response to mating pheromone binding to the heterologous receptor. Since FAR1 is a primary factor in the cell cycle regulatory pathway, its deletion or mutation is preferred in the expression constructs of the present invention. Yeast cells transformed with such constructs yield superior yeast strains for ligand-binding assays.

The mating signal transduction pathway is known to become desensitized by several mechanisms including pheromone degradation and modification of the function of the receptor, G proteins and/or downstream elements of the pheromone signal transduction by the products of the SST2, STE50, AFR1 (Konopka, J. B. (1993) Mol. Cell. Biol. 13, 6676–6888] and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations e.g. STE50, sgv1, ste2, ste3, pikl, msg5, sig1, and afr1, have the similar effect of increasing the sensitivity of the bioassay. One skilled in the art will understand that increased sensitivity of the assay systems is attained through deletion of one or more of these aforementioned genes, introduction of mutations that down-regulate their expression, or in certain instances, effecting their overexpression. For example, in the STE50 construct, overexpression of the gene is desired, not deletion of the gene.

Introduction of a constellation of mutations in the mating signal transduction pathway results in a yeast cell well suited to expression of heterologous G protein-coupled receptors, which are able to functionally respond to their cognate ligands, while providing a biological response that signals the binding of the receptor to the ligand.

In conjunction with one or more of the above-referenced mutations, a particularly convenient method for detecting ligand-binding to heterologous receptor expressed in yeast cells is to utilize a conventional genetic-indicator system. Thus, in certain preferred embodiments, the cells are provided with an additional heterologous nucleotide sequence, comprising a pheromone-responsive promoter and an indicator gene positioned downstream from the pheromone-responsive promoter and operatively associated therewith. With such a sequence in place, the detecting step can be carried out by monitoring the expression of the indicator gene in the cell. Any of a variety of pheromone responsive promoters could be used, examples being promoters driving any of the aforementioned pheromone responsive genes (e.g. mFa1, mFa2, MFA1, MFA2, STE6, STE13), the BAR1 gene promoter, and the FUS1 gene promoter. Likewise, any of a broad variety of indicator genes could be used, with examples including the HIS3, G418r, URA3, LYS2, CAN1, CYH2, and LacZ genes. A particularly preferred reporter gene construct is utilized by fusing transcription control elements of a FUS1 gene to HIS3 protein coding sequences, and replacing the original FUS1 gene with this reporter construct. Expression of the HIS3 gene product is thereby placed under the control of the pheromone signal transduction pathway. Yeast strains (his3) bearing this construct are able to grow poorly on supplemented minimal medium lacking histidine, and are sensitive to an inhibitor of the HIS3 gene product. In other preferred embodiments, plasmids carry a FUS1-lacZ gene fusion. Expression of the FUS1 gene is stimulated in response to receptor activation by binding of pheromone. Therefore, signal transduction can be quantitated by measuring P-galactosidase activity generated from the FUS1-lacZ reporter gene.

Other useful reporter gene constructs, still under the control of elements of the pheromone signal transduction pathway, but alternative to the above-discussed reporter systems, may involve signals transduced through other heterologous effector proteins that are coexpressed. For example, 1) ligand-dependent stimulation of a heterologous adenylylcyclase may permit a yeast strain lacking its own adenylylcyclase due to mutation in the cdc35 gene to survive, 2)ligand-dependent stimulation of a heterologous G protein-coupled potassium channel may permit a yeast strain unable to grow in medium containing low potassium concentration [(trk1, trk2), for example, see Anderson, J. A. et al (1992)( Proc. Natl. Adad. Sci. USA 89, 3736–3740] to survive, or 3) ligand-dependent stimulation of a heterologous phospholipase C (especially PLC-β) may permit a yeast strain lacking its own PLC [(plc), for example, see Payne, W. E. and Fitzgerald-Hayes, M. (1993) Mol. Cell Biol. 13,4351–4363] to survive.

Any DNA sequence which codes for an adenylylcyclase may be used to practice the present invention. Examples of adenylylcyclase include the product of the D. melanogaster Rutabaga gene and the mammalian subunit types I–VIII [for review see, Tang, W. J. and Gilman, A. G. (1992) Cell 70, 869–872], and mutants and homologs thereof, along with the DNA sequences encoding same, which are useful for practicing the present invention.

Any DNA sequence which codes for a G protein-gated potassium channel may be used to practice she present invention. Examples of G protein-coupled potassium channel include GIRK1 [Kubo, Y. Reuveny, E., Slesinger, P. A., Jan, Y. N., and Jan, L. Y. (1992) Nature 365, 802–806], subunits useful for practicing the present invention, and mutants and homologs thereof, along with the DNA sequences encoding same.

Any DNA sequence which codes for a phospholipase protein may be used to practice the present invention. Examples of phospholipase (PLC) proteins include the D. melanogaster norpA gene product and the PLC-β proteins [for review, see Rhee, S. G., and Choi, K. D. (1992) J. Biol. Chem. 267, 12392–12396], subunits useful for practicing the present invention, and mutants and homologs thereof, along with the DNA sequences encoding same.

A particularly preferred yeast expression system is described herein, having yeast cells bearing SSTR and chimeric G-protein, and dependent upon the presence of somatostatin for continued growth. As noted above, transformed host cells of the present invention express the proteins or protein subunits coded for by the heterologous DNA sequences. When expressed, the G protein-coupled receptor is located in the host cell membrane (i.e., physically positioned therein in proper orientation for both the stereoselective binding of ligands and for functional interaction with G proteins on the cytoplasmic side of the cell membrane). Implementation of the sensitive and specific yeast expression system described herein will facilitate description of structural and functional aspects of receptor-ligand and receptor-G protein interactions. Powerful genetic selection schemes, made possible by modification of elements of the mating signal transduction pathway, may be employed to identify aspects of the receptor that have effects on agonist selectivity, ligand stereo selectivity, and determinants of agonist/antagonist binding. The role of proteins that modify the response of receptors and G proteins to ligand may be worked out in detail with the assistance of this powerful genetic system. Importantly, the system provides a generalized approach to the study of the functioning and components of the G protein-coupled signal transduction system, as well as a generalized approach to screening assays utilizing the G protein coupled signal transduction system. The present invention provides expression constructs and assay systems adapted to receive any of a variety of heterologous G protein coupled receptors, in the form of "expression cassettes". The heterologous G protein-coupled receptor it is desired to study is simply inserted into the vectors herein provided, and expressed in yeast cells. Ligands that may bind to the expressed receptor are allowed to come into contact with the cells in any conventional assay manner, and the effects of the interaction are easily monitored. The systems presented herein thus provide tremendous utility in the identification of ligands for orphan G protein-coupled receptors and for discovering novel therapeutically useful ligands for receptors of medical, veterinary, and agricultural importance.

The following Examples are provided to further illustrate various aspects of the present invention. They are not to be construed as limiting the invention.

EXAMPLE 1

Functional expression of mammalian G α proteins in *Saccharomyces cerevisiae*

A sensitive bioassay is utilized to measure interference of yeast Gα and GβY interactions by expression of heterologous Gα proteins. Mammalian Gα genes are expressed from $2\mu$ or centromere-bearing plasmids under the control of the constitutive PGK or the inducible CUP1 promoter. The data demonstrates that the rat $G\alpha_5$, $G\alpha_{12}$, and chimeric yeast/mammalian Gα can effectively interact with yeast GβY.

Media and Strains. Growth of bacterial strains and plasmid manipulations are performed by standard methods (Maniatis T., Molecular Cloning, (Cold Spring Harbor Laboratory Press, 1982). Growth and transformation of yeast strains are performed as described in Rose et al. (Rose M. D., Methods in yeast genetics, Cold Spring Harbor Laboratory Press, 1990). The yeast strains used in these studies (CY414, MATa ura 3–52 trp1 leu2 his3 pep4::HIS3) originate from strains described by E. Jones (Jones, E. W., Ann,. Rev. Genet 18:233, 1984). CY414 is sequentially transformed with the FUS1-lacZ fusion plasmid pSB234 (Trueheart J., et al Mol. Cell. Biol. 7(7): 2316–2328, 1987) and Gα expression plasmids.

Construction of G α expression plasmids. Rat cDNA clones for $G\alpha_5$ and $G\alpha_{12}$ and for fusions with the yeast SCG1 gene are described elsewhere [Kang, Y. S., Kane, J., Kurjan, J., Stadel, J. M., and Tipper, D. J. (1990) Mol. Cell. Biol. 10, 2582–2590]. To express these genes from low-copy-number plasmids, XhoI-SalI fragments containing each expression cassette (including the PGK promoter and terminator sequences) are isolated and cloned into the CEN plasmid pRS414 digested with XhoI. For inducible expression, the DNA segment containing PGK promoter sequences are replaced with upstream activating sequences form the CUPI gene.

β-galactosidase assays. Cultures are diluted to $5 \times 10^7$ cells/ml and aliquotted into separate tubes. Pheromone is added to a final concentration of $10^{-9}$M to one sample. Cultures are then incubated for 4 hrs at 30° C. Subsequent measurement of β-galactosidase activity is conducted as described elsewhere (Rose M. D., Cold Spring Harbor Laboratory Press, 1990).

High and low-copy-number plasmids carrying the yeast SCG1 or mammalian $G\alpha_5$ or $G\alpha_1$ or chimeric yeast/mammalian Gα genes expressed from the yeast PGK promoter are transformed into a wild-type yeast strain also containing a plasmid carrying a FUS1-lacZ gene fusion. Expression of the FUS1 gene is stimulated in response to receptor activation by binding of pheromone. Therefore, signal transduction can be quantitated by measuring β-galactosidase activity generated from the FUS1-lacZ reporter gene. Interference of normal signal transduction by expression of a heterologous Gα protein is observed as a decrease in β-galactosidase activity.

Strains expressing introduced Gα genes are assayed for pheromone-induced gene activation. Data are represented as percent of wild-type response in FIG. 1. Expression from all Gα plasmids reduced FUS1-lacZ expression levels demonstrating that the Gα proteins functionally coupled to yeast GβY. A dose dependence was observed for Scg1, Gαs and $G\alpha_{12}$. Expression from high-copy-number plasmids greatly reduces signaling suggesting that a large excess of heterologous Gα protein is present. The Scg-Gαi2 chimeric protein reduces signaling to near the unstimulated background levels even from the low-copy-number plasmid. Other CEN expression plasmids reduce signaling to 53 to 84% of wild-type levels.

Figure 2:
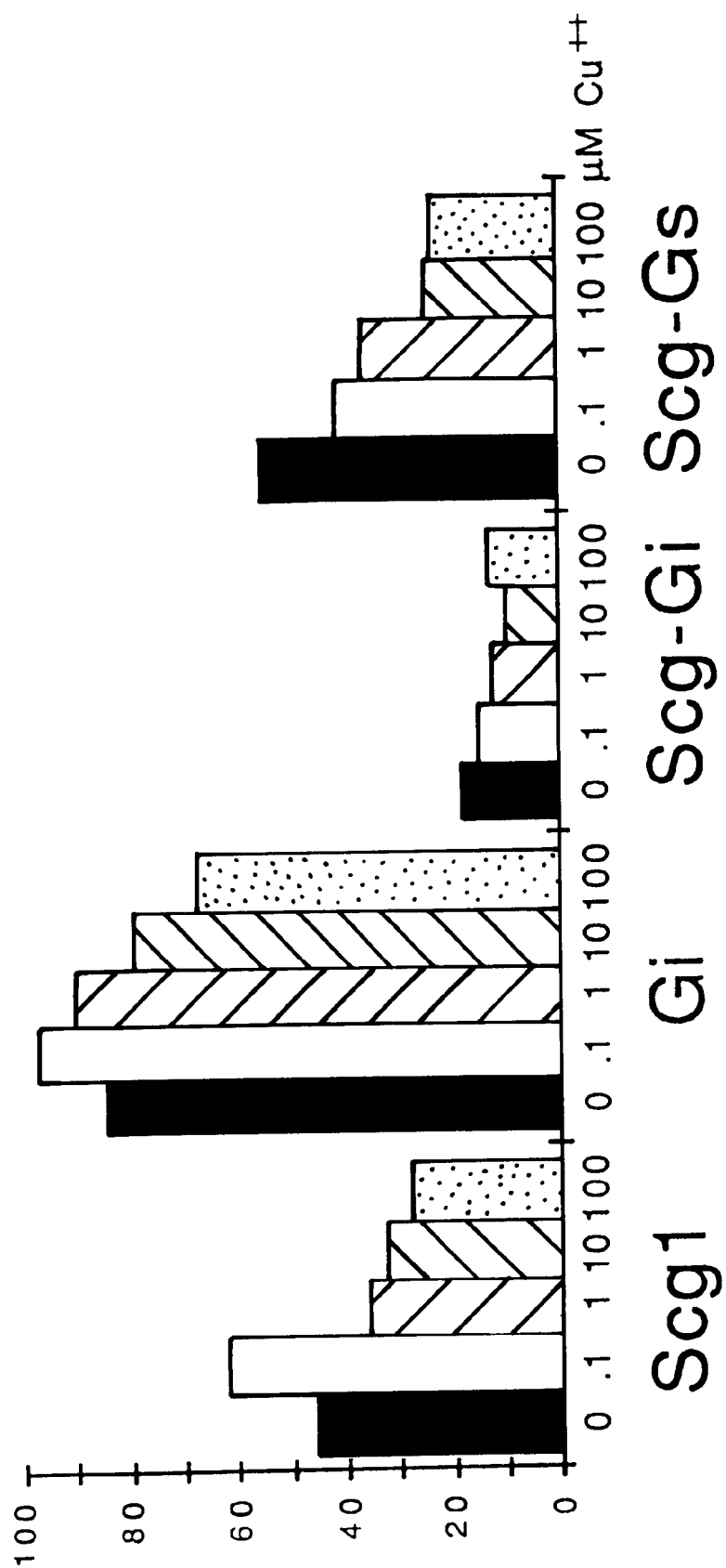
FIG. 2 Strains containing the indicated CUPlp-Gα expression plasmid and grown in medium containing the indicated concentration of copper are treated with mating pheromone (α factor). A measure of resulting signal transduction is provided by a reporter plasmid carrying FUS1-lacZ. Data are represented as a percent of β-galactosidase activity measured in a strain expressing no exogenous Gα protein.

To achieve more precise control of Gα expression and reduce expression to a level sufficiently low that minimal effects on pheromone induced signaling will occur, Gα genes (except Gαs) are placed under the control of the inducible CUP1 promoter and transformed into yeast on low-copy-number plasmids. The level of signaling repression mediated by these plasmids is dependent on the concentration of Cu++4 added to the medium (FIG. 2). However, basal expression (no Cu++4 added) was equivalent to levels observed from the PGK promoter (FIG. 1). As in the previous experiment, the SCG-Gαi2 chimeric protein reduces signaling to almost background levels.

The data presented in FIGS. 1 and 2 indicates that all Gα expression plasmids examined produce functional Gα proteins in that all inhibit the signal transduction pathway. Using a constitutive promoter (PGK), most Gα genes exhibit a dose-dependent effect with high-copy-number 2 micron plasmids drastically reducing signaling (FIG. 1). Lower expression from CEN plasmids reduce signaling levels as little as 16% (See G., FIG. 1). Expression of the Gα genes from the CUP1 promoter shows expected dose/response effects with reduced signaling correlated to increased Cu++concentrations (FIG. 2).

EXAMPLE 2

Pharmacological evaluation of heterologous G protein-coupled receptors expressed in *Saccharomyces cerevisiae*

Yeast strains. Growth and transformation of yeast strains are performed as described (Rore, M. D., Methods in Yeast Genetics, Cold Spring Harbor Laboratory Press, 1990). The yeast strains used in these studies (CY414; MATa ura 3–52 tzp1 leu2 his3 pep4ΔHIS3) originate from strains described by E. Jones (Jones, E. W., Ann. Rev. Genet, 18:233, 1984).

Nucleic acid manipulation. Growth of bacterial strains and plasmid manipulations are performed by standard methods [Sambrook, J., Fritsch, E. F., and Maniatis, T., Molecular Cloning, 2nd ed. (Cold Spring Harbor Laboratory Press, 1989)]. DNA sequencing is performed by high temperature cycle sequencing (Applied Biosystems).

Protein analysis. Receptor expression strains are grown in synthetic complete medium lacking specific nutrients to select for plasmid retention and containing 3% galactose to induce receptor gene expression. Cells are pelleted and washed in lysis buffer (10 mM sodium bicarbonate, pH 7.2, 1 mM EGTA, 1 mM EDTA) then resuspended in lysis buffer plus protease inhibitors (5 μg/ml leupeptin, 10 μg/ml benzamidine, 10 μg/ml Bacitracin, 5 μg/ml pepstatin, 5 μg/ml aprotinin) and lysed by physical disruption with glass beads. Debris is removed by centrifugation at 1000×g for 10 min. The membrane fraction is isolated by centrifugation at 100,000×g for 10 min. This pellet is washed once in lysis buffer plus inhibitors. Polyacrylamide gel electrophoresis of yeast extracts is performed by standard methods except without boiling of samples. Proteins are transferred to Immobilon-P millipore filters by the semi-dry technique. Receptor protein is visualized using ECL reagents with rabbit anti-Ste2 antibodies.

Radioligand binding assays. Reactions are performed in a volume of 0.2 μl with 5 to 50 μg of protein. Binding assays for 5HT1a receptor or β2-adrenergic receptor ligands use buffer of 50 mM Tris, pH 7.4, 10 mM $MgCl_2$. Somatostatin binding is performed in a buffer of 50 mM HEPES, pH 7.4, 5 mM $MgCl_2$. After allowing ligand binding to reach equilibrium at room temperature, membrane fractions are isolated on GFC glass fiber filters. The following final concentrations of ligands are used: radioligands-$^3$H spiperone, 80 nM; $^{125}$I-cyanapindolol, 250 pM; [$^{125}$I-tyr$^{11}$]-somatostatin 14, 250 pM; competitors-serotonin, 10 μM; propranolol, 20 μM somatostatin 14, 1 μM. The guanosine triphosphate analog Gpp(NH)p is used at 100 μM.

Expression of the human 5HT1a serotonergic receptor. The gene encoding the human 5HT1a receptor is modified to add the first 14 amino acids of the yeast Ste2 protein, cloned into the expression plasmid pMP3 and, designated pCHI11. This strain, designated CY382, is grown in medium containing galactose to induce receptor expression, fractioned and tested for receptor activity by binding of the radiolabelled antagonist $^3$H-spiperone.

Figure 3:
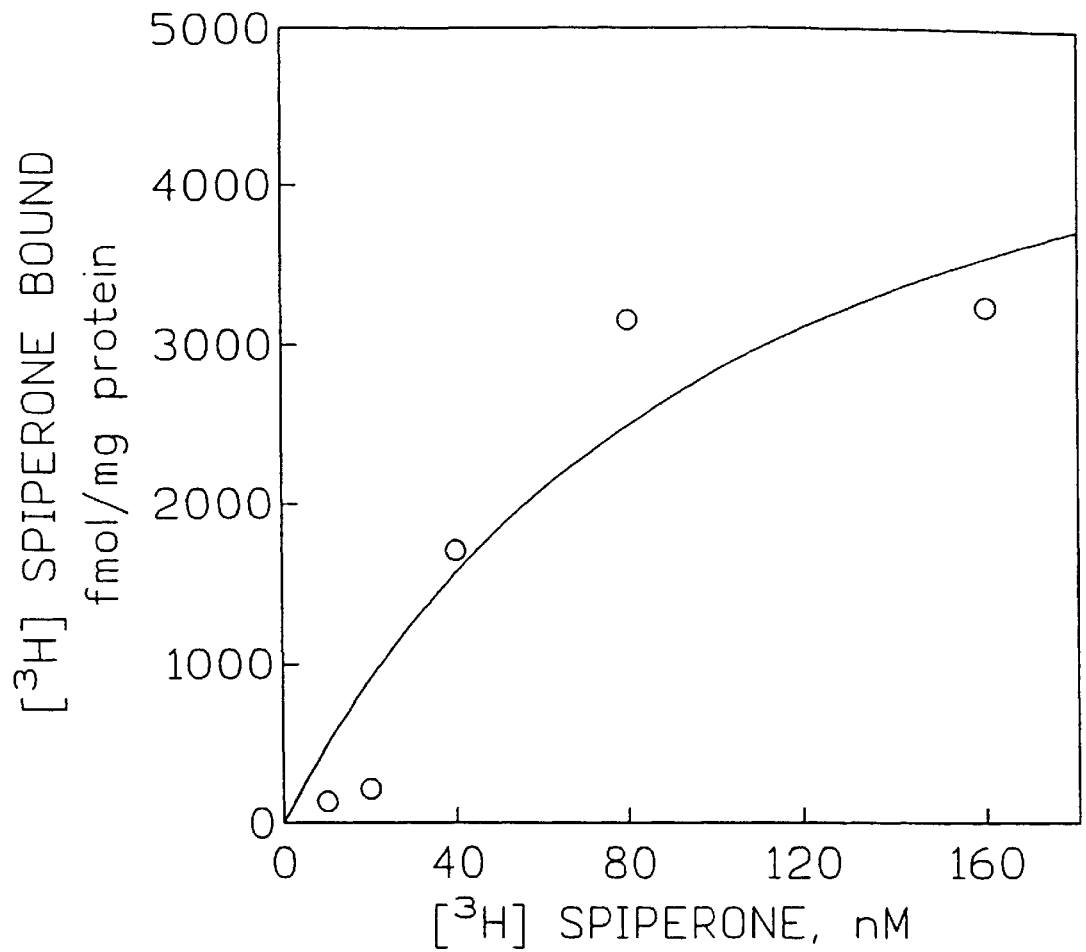
FIG. 3 Saturation binding of $^3$H-spiperone to yeast membrane fractions prepared from a strain (CY382) expressing the 5HTla serotonin receptor. Bmax 32 3.2 pmol/mg protein; Kd–115 nM.
Figure 4:
FIG. 4 Amino-terminal chimeric Ste2/5HTla receptors. The CHI11 receptor contains the first 14 amino acids of the yeast Ste2 protein. The CHI17 receptor has a replacement of the amino-terminus of the 5HTla receptor through the first two transmembrane domains with the corresponding region of the Ste2 receptor. The CHI18 receptor has the same Ste2 sequences fused directly to the amino-terminus of the 5HTla receptor to create a receptor predicted to span the cellular membrane nine times. Bmax values were determined by measuring maximal binding of the radiolabeled ligand 3H-spiperone. Values are given as pmol radioligand bound per mg total protein.
Figure 4:
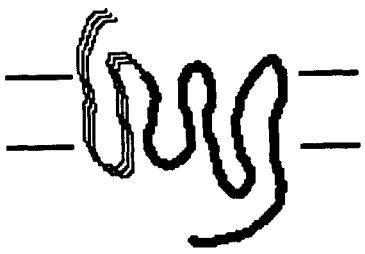
Figure 4:
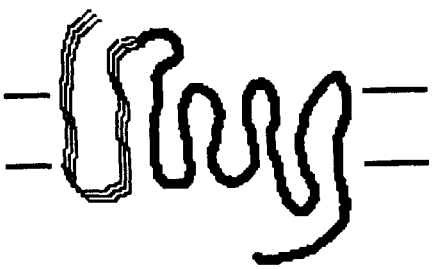

Saturation binding demonstrates that the receptor is expressed at high levels (Bmax=3.2 pmol/mg protein) and that it binds spiperone with an affinity (Kd=115 ZiM; FIG. 3) similar to that observed in mammalian tissues (Kd–20 to 100 nM) Two chimeric receptor genes are engineered; in pCH117, sequences encoding the N-terminus including the first two transmembrane domains of the rHT1a receptor are replaced with the corresponding sequences of the Ste2 receptor, and in pCH118, these Ste2 sequences are added directly to the N-terminus of the 5HT1a receptor to create a novel nine-transmembrane-domain receptor FIG. 4). Strains expressing these receptors are examined for binding of radiolabelled ligand. Both receptors demonstrate specific binding of the 5HT receptor antagonist $^3$H-spiperone (FIG. 4). Replacement of the first two transmembrane domains with those of an unrelated receptor does not apparently affect binding of this ligand. Addition of transmembrane domains do not effect binding, suggesting that this unusual receptor can attain a functional conformation in the cell membrane. Strains carrying pCHI11, pCHI17, or pCHI18 produce Bmax values of 3.1, 1.6, or 0.7 pmol/mg, respectively. Although these chimeric receptors produce interesting results regarding receptor structure, they do not enhance overall levels of functional receptors in the cell.

All intracellular sequences of the 5HT1a receptor are replaced with corresponding sequences of the yeast Ste2 protein to directly couple the receptor to the yeast G protein. The resultant chimeric receptor, CHI16, is expressed in a wild-type yeast strain and examined for high affinity binding of 5HT1a receptor agonists. Agonist binding is not detected. However, the level of radiolabelled spiperone binding is equal to CHI11, indicating that this receptor is expressed at high levels and in a functional conformation.

Figure 5:
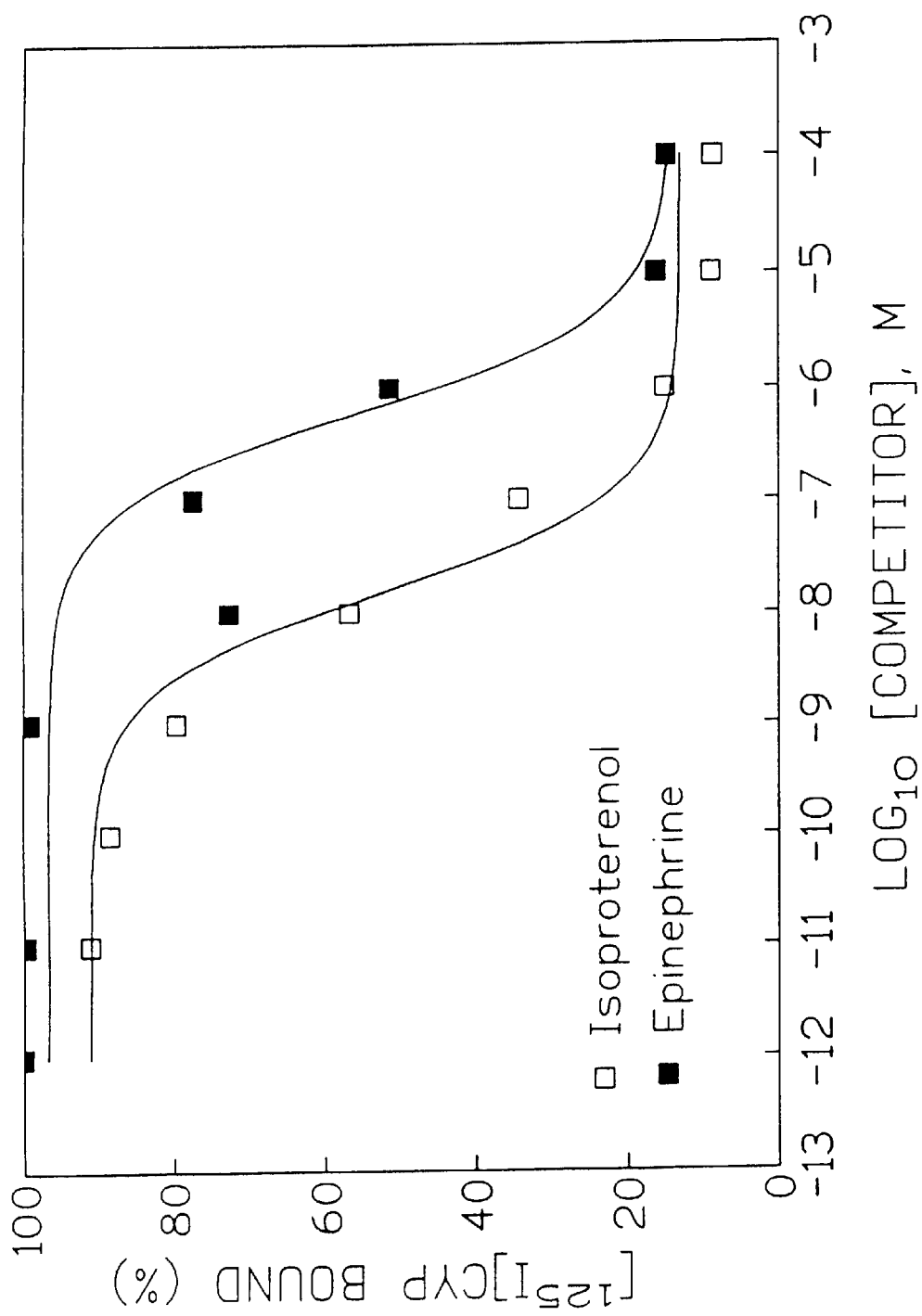
FIG. 5 Competition binding analysis of the agonists isoproterenol or epinephrine against $^{125}$I-cyanopindolol with crude membrane extracts prepared from a wild-type yeast strain expressing the β$_2$-adrenergic receptor. Data are presented as percent maximal radioligand binding. IC$_{50}$ values= 10 nM, isoproterenol; 200 nM, epinephrine.
Figure 6:
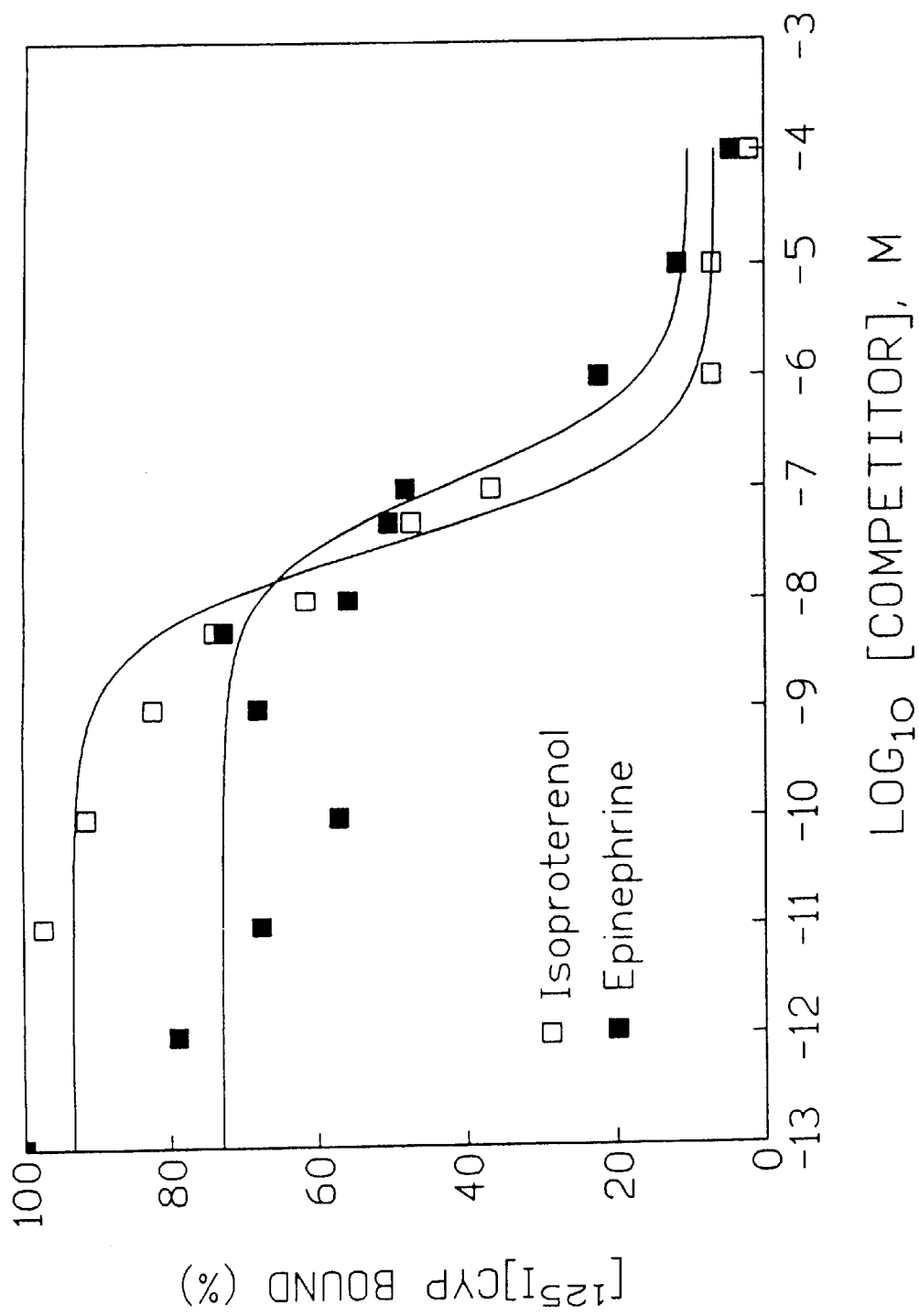
FIG. 6 Competition binding analysis of the agonists isoproterenol or epinephrine against $^{125}$I-cyanopindolol with extracts prepared from a yeast strain coexpressing the β$_2$-adrenergic receptor and mammalian G$_{αs}$.Data are presented as percent maximal radioligand binding. IC$_{50}$ values= 10 nM, isoproterenol; 60 nM, epinephrine.

Expression of the human β2-adrenergic receptor. The human adrenergic receptor is expressed in yeast with the intention of using it as a model to optimize expression and G protein coupling. A yeast strain expressing the receptor is examined by Scatchard analysis for binding of the ligand $^{125}$I-cyanopindolol. Binding is saturable and demonstrated a Kd (23 pM), similar to that reported in mammalian tissues. Strains with or without coexpressed Gαs are then examined in competition assays in which binding of this radioligand is competed with the agonists isoproterenol or epinephrine. High affinity binding, which is only expected to occur if the receptor is actively coupled to G protein, was observed in both strains (FIGS. 5 and 6). The extrapolated Ki values for these ligands (isoproterenol=10 nM; epinephrine=60 n) are consistent with affinities observed in mammalian tissues and exhibit the expected order of potency. However, other data suggest that the high affinity binding of agonists to the β2-adrenergic receptor in yeast is anomalous and not a result of coupling to G protein. In particular, the third intracellular loop (containing the primary Gαcontact points) of the β2-adrenergic receptor is replaced with the corresponding domain of the yeast Ste2 receptor. This receptor exhibits the same affinities for adrenergic agonists suggesting that the β2-adrenergic receptor takes on an inappropriate conformation in yeast.

Figure 7:
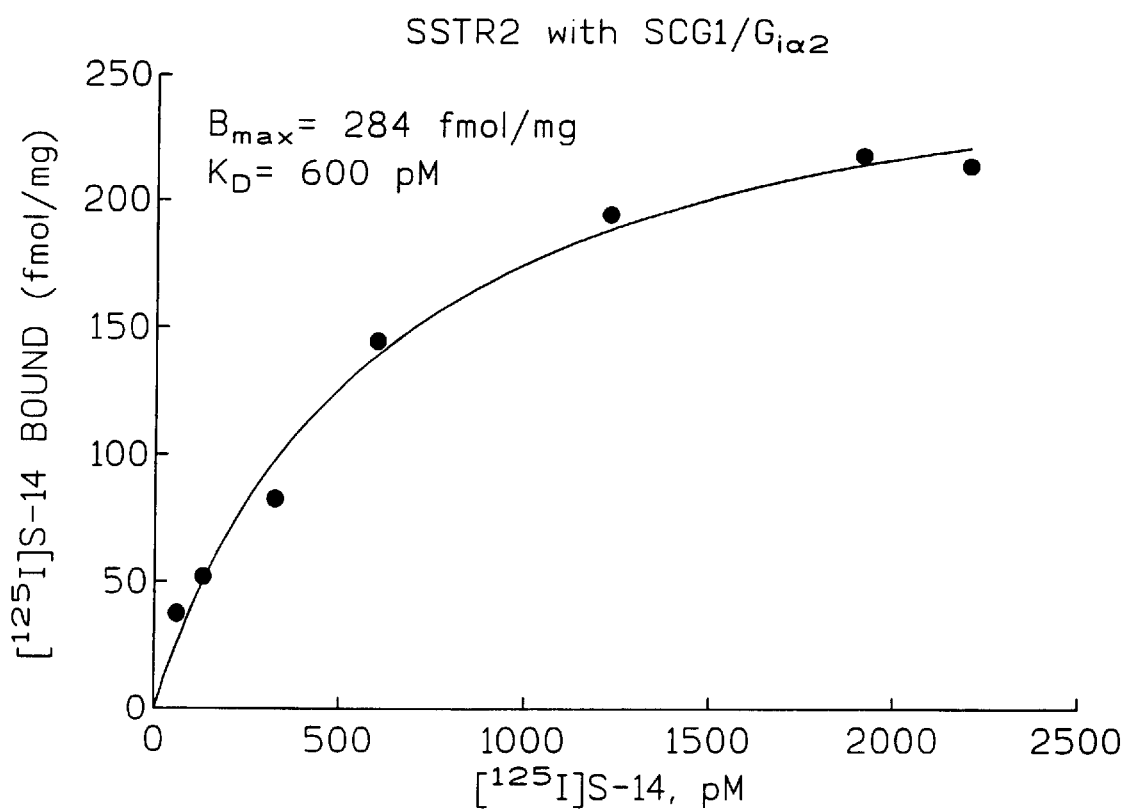
FIG. 7 Saturation binding of [$^{125}$I]tyr$^{11}$S-14 to membranes of yeast cells coexpressing the SSTR2 subtype and Scgl/G$_{iα2}$. Membranes from yeast cells expressing the SST2 subtype were prepared as described in Experimental Procedures. Saturation binding was performed with 20–1600 pM [$^{125}$I]tyr$^{11}$S-14. Non-specific binding for each point as cpm bound in the presence of 1 μM cold S-14 ranged from 10 to 40%. Displayed is a representative experiment performed in duplicate.
Figure 8:
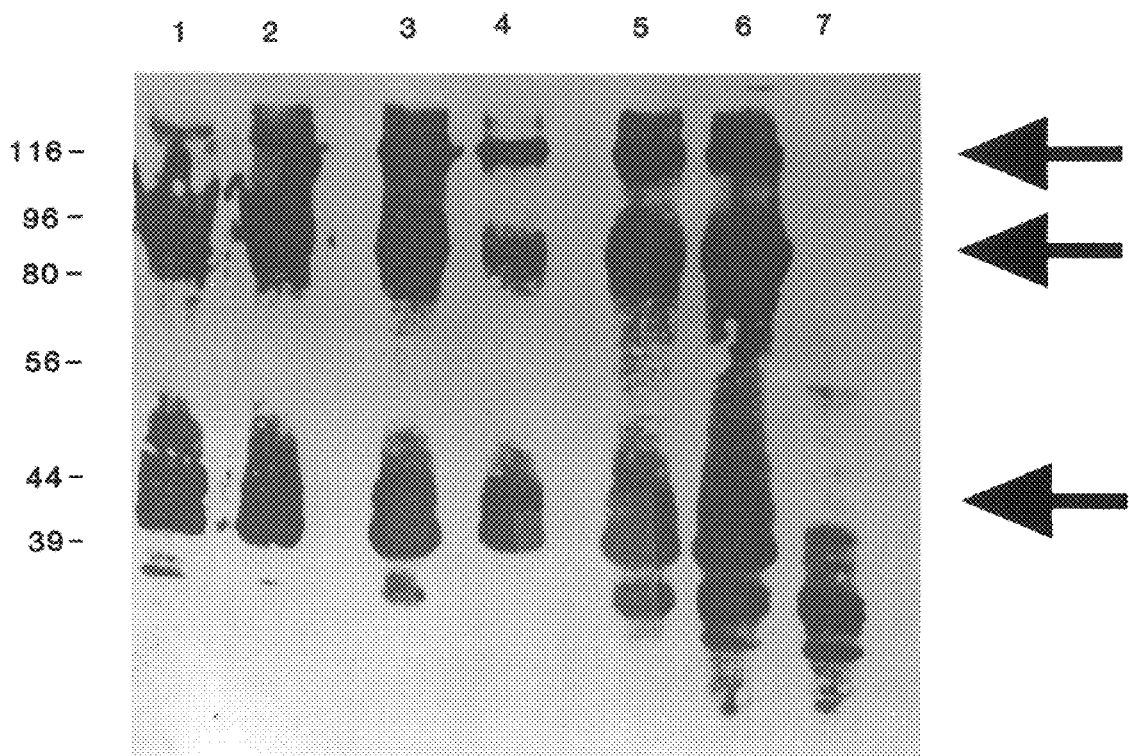
FIG. 8 Immunoblot showing somatostatin receptor expression. Membrane fractions are isolated from the indicated yeast strains. Aliquots of 5 to 30 μg of protein are examined by polyacrylamide gel electrophoresis/Western blot analysis. Molecular weight markers are indicated in kilodaltons. Arrows mark somatostatin receptor protein bands. Several species of this receptor are observed; doublet and triplet bands in addition to the 43 kd single receptor. Lanes, 1+2, CY602 (see Table 1); 3+4. CY603; 5+6, CY624; 7, congenic strain expressing no receptor.

Expression of rat somatostatin receptor. High affinity binding of somatostatin to SSTR2 is dependent on formation of a receptor/G protein complex (Strnad et al, 1993). When SSTR2 and G protein are uncoupled from each other, high affinity binding of [$^{125}$I]tyr$^{11}$S-14 is attenuated. As shown in FIG. 8, binding of [$^{125}$I]tyr$^{11}$S-14 to SSTR2 expressed in yeast coexpressing Scg1/G$_{\alpha i2}$ is saturable and of high affinity. The calculated Kd of [$^{125}$I]tyr$^{11}$S-14 binding SSTR2 expressed in yeast is 500 pM. Similar binding affinities are observed when G$_{gi2}$ is coexpressed with SSTR2 rather than Scg1/G$_{\alpha i2}$. The K$_d$ observed in yeast is in close agreement to the calculated K$_d$ of [$^{125}$I]tyr$^{11}$S-14 binding of SSTR2 expressed in mammalian cells (Strnad et al., 1993). It is demonstrated that addition of the yeast Ste2 receptor to the N-terminus of this receptor has no affect on its ability to bind S-14. The Ste2 sequences act as a tag for immunochemical examination of receptor expression. The immunoblot shown in FIG. 7 illustrates the high level of expression of SSTR2 in three different strains. Yeast-strains expressing the SSTR2 somatostatin receptor and different Gα proteins are derived from strain YPH500. These strains share the genotype MATa scg1ΔhisG lys2–801 ura3–52 leu2Δ1 trp1Δ63 his3Δ200 ade2 SSTR2. Strains designated CY624 (Gαi2), CY602 (Gαs, and CY603 Scg1) are examined for specific binding of radiolabelled somatostatin-14 (S-14). All three exhibit some degree of somatostatin binding (Table 1). High affinity binding of this ligand requires coupling of the receptor to G protein, normally Gαi (Luthin D. R. 1993; Strnad J. 1993), so the high level of binding in the absence of Gαi is unexpected. As confirmation that the receptor is coupled to G proteins, binding is examined in the presence of the nonhydrolyzable guanosine triphosphate analog Gpp (NH)p. The addition of this compound eliminates ligand binding (Table 1), demonstrating that the SSTR2 receptor is coupled to G protein. These data demonstrate that a mammalian G protein-coupled receptor can functionally interact with a G protein composed of its favored Gα protein plus yeast Gβ and GY subunits and that a heterologous receptor can functionally couple to a G protein entirely composed of yeast subunits.

TABLE 1

Binding af $^{125}$I-somatostatin

| STRAIN$^a$ | Gα | Bmax$^b$ | +Gpp (NH) p$^c$ |
|---|---|---|---|
| CY624 | Gαi | 94.5 | 22% |
| CY602 | Gαs | 13.7 | 0% |
| CY603 | Scg1 | 24.7 | 4% |

$^a$Crude membrane extracts were prepared from yeast strains expressing the rat SSTR2 somatostatin receptor subtype and the indicated Gα protein. The maximal binding of radiolabeled somastatin 14 was measured as described in the text.
$^b$Bmax values are given as fmol/mg total protein.
$^c$The non-hydrolyzable GTP analog Gpp (NH)p was added to samples to uncouple receptor and G protein. Data are presented as percent radioligand bound compared to untreated samples.

Crude membrane extracts were prepared from yeast strains expressing the rat SSTR2 somatostatin receptor subtype and the indicated Gα protein. The maximal binding of radiolabeled somatostatin 14 was measured as described in the text. $^b$Bmax values are given as fmol/mg total protein. $^c$ The non-hydrolyzable GTP analog Gpp(NH)p was added tp samples to uncouple receptor and G protein. Data are presented as percent radioligand bound compared to untreated samples.

Expression of Drosophila muscarinic acetylcholie receptor. DNA sequences encoding a Drosophila muscarinic acetylcholine receptor (Dm mAChR) are modified by addition of a SalI site in the 5' coding sequences through the use of PCR. DNA sequences encoding the first 23 amino acids of the STE2 gene product are added to the 5'end of Dm mAChR as a BamHI/SalI fragment. The modified Dm mAChR is inserted into the BamHI site in plasmid pMP3, placing expression of the receptor under the control of the GAL1 promoter,, forming plasmid pMP3-Dm mAChR. Strain CY414 is transformed with this plasmid and cultured for receptor expression by standard methods. Crude membrane preparations are prepared from these cells and tested for the presence of specific binding sites for the muscarinic antagonist 3H-quinuclidinyl benzilate (10 nM) competed with atropine (50 μM). Specific binding sites (Bmax 10 and 30 fmol/mg) are observed.

Figure 9:
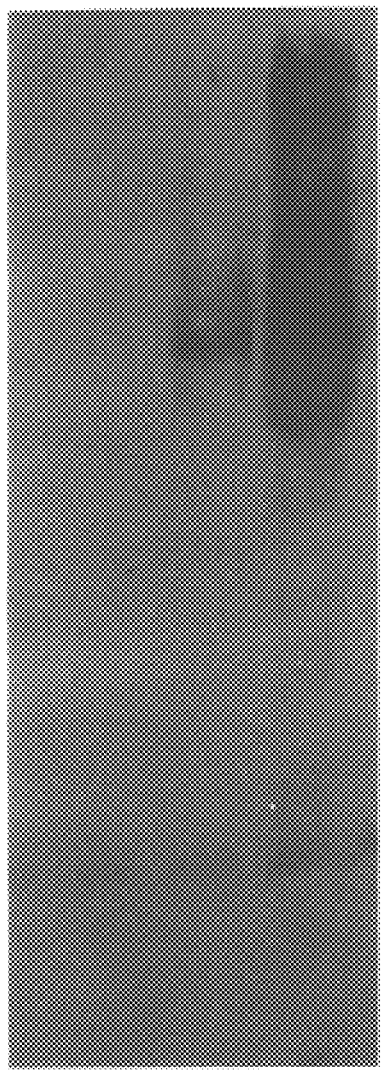
FIG. 9 Immunoblot showing muscarinic acetylcholine receptor (mAchR) expression. Membrane fractions are isolated from the indicated yeast strains. Aliquots of 30 μg of protein are examined by polyacrylamide gel electrophoresis/ Western blot analysis as described in the text. Molecular weight markers are indicated in kilodaltons. Arrows mark mAchR protein bands.

Drosophila mAchR expression is also detectable by immunoblotting methods. An abundant 75 kDa polypeptide, consistent with the predicted molecular weight from the primary sequence of mAchR, as detected n samples of protein (30μg/lane) from crude membrane preparations from cells expressing mAchR from pMP3 using an antibody directed against the associated Ste2 epitope (FIG. 9). Substantially less protein is detected when mAchR is expressed from pMP2 a derivative of pMP3 lacking GAL4 sequences, which is not expected to confirm high level expression of mAchR.

Expression of an α2-adrenergic receptor ( 2α-AR). An EcoRI-NarI fragment from plasmid pMP3 including the GAL10 promoter EcoRI-BamHI fragment, DNA sequences encoding the first 23 amino acids of the STE2 gene product present on a BamHI-SalI fragment, SaiI-SphI polylinker fragment from YEp352, and STE7 terminator sequences, is transferred to pRS424, forming pLP15. A PstI-PvuII fragment encoding a porcine α2A-AR [Guyer, C. A., Horstman, D. A., Wilson, A. L., Clark, J. D., Cragoe, E. J., and Limbird, L. E. (1990) J. Biol. Chem. 265, 17307–17317] is inserted into the PstI-SmaI sites of pLP15, forming pLP50. An EcoRI fragment of GAL4 is inserted into the EcoRI site of pLP50, forming pLP60. Strain LY124 [a derivative of YPH500 (Stratagene) containing the scg1ΔhisG allele and bearing plasmid pLP10 [pLPlO: pUN75 (Elledge, S. J. and Davis, R. W. Genetics 87, 189–194) containing the PGK-Scg1-Gαi2 XhoI-SalI fragment from pPGKH-Scg1-Gαi2 inserted into the SalI site] is transformed with pLP60 and cultured for receptor expression by standard methods. Crude membrane preparations are prepared from these cells and tested for the presence of specific binding sites for the α2-AR antagonist 3H-rauwolscine (200 nM) competed with phentolamine (10 μM). Specific binding sites with a Bmax of between 10 and 84 fmol/mg were observed.

Figure 10:
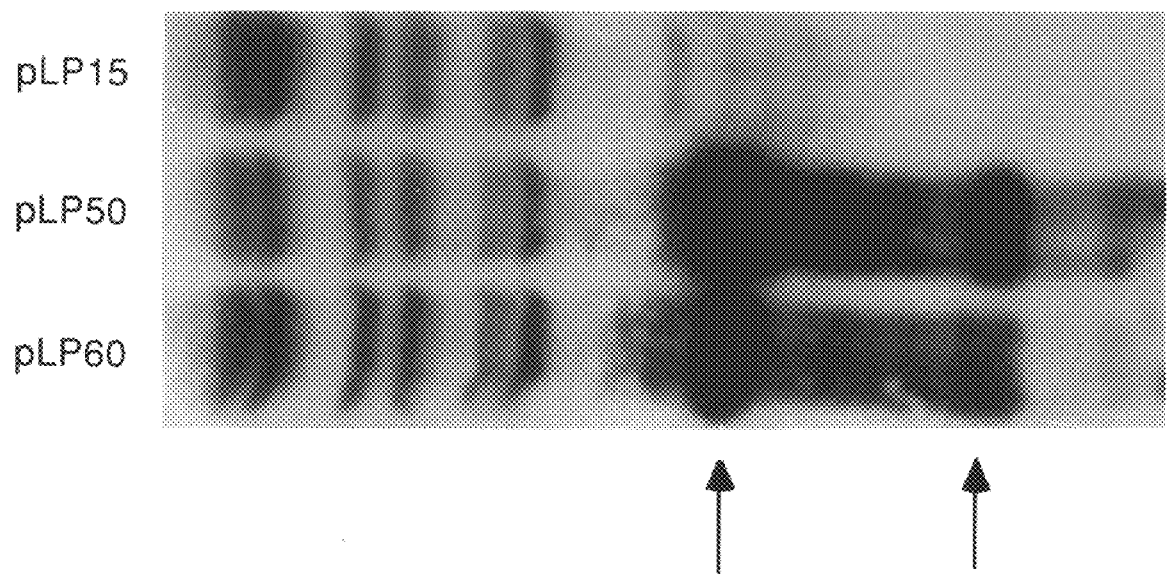
FIG. 10. Immunoblot showing α2-AR expression. Membrane fractions are isolated form the indicated yeast strains. Aliquots of 30 μg of protein are examined by polyacrylamide gel electrophoresis/ western blot analysis. Molecular weight markers are indicated in kilodaltons. Arrows mark α2-AR protein bands.

Porcine α2AR expression is also detectable by immunoblotting methods (FIG. 10). Several abundant polypeptides are detected in samples of protein (30μg/lane) from crude membrane preparations from cells expressing α2AR from pMP3 using an antibody directed against the associated Ste2 epitope.

EXAMPLE 3

Aqonist dependent growth of yeast in response to somatostatin receptor agonists.

Figure 11:
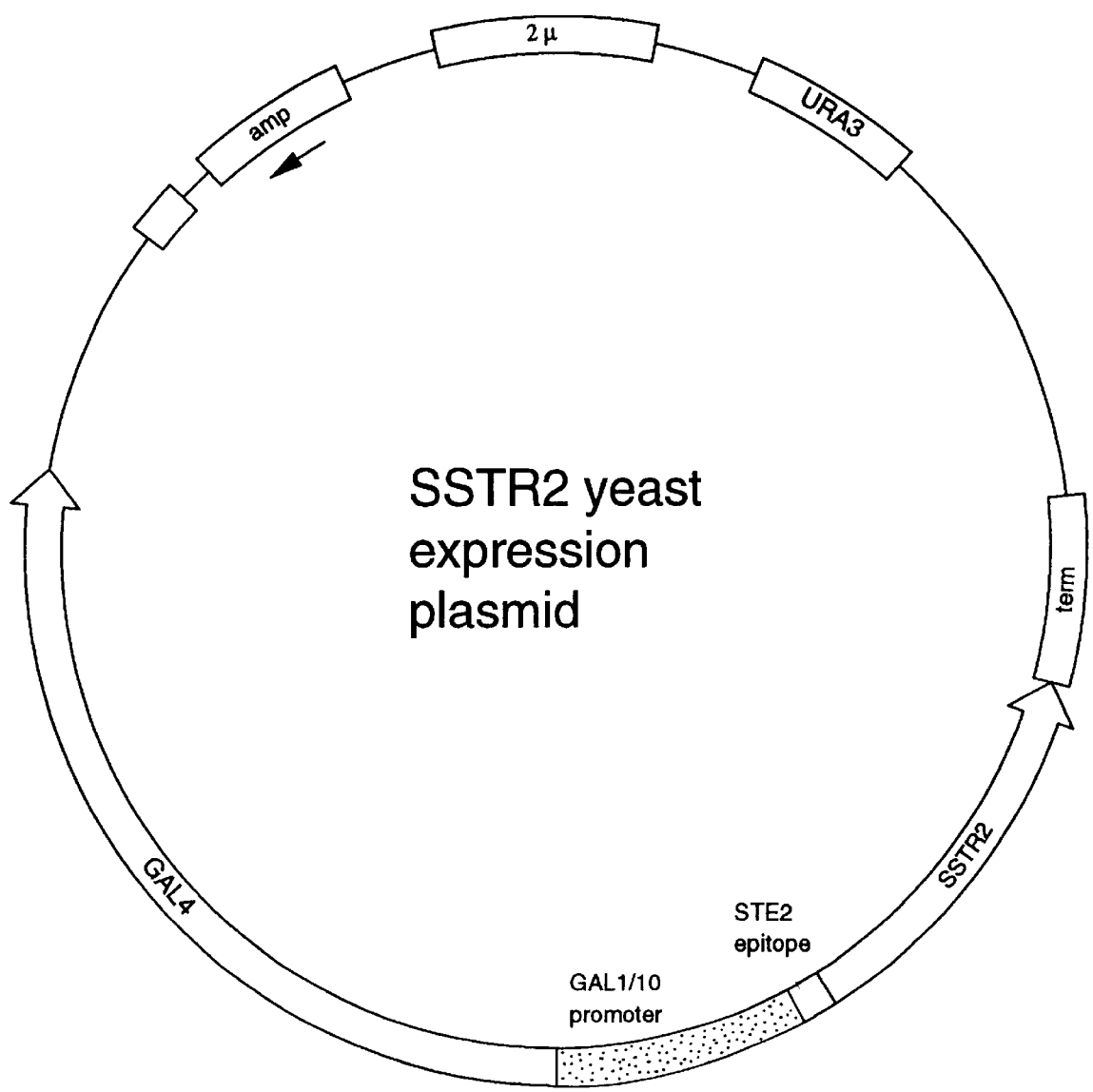
FIG. 11 Somatostatin receptor expression plasmid, pJHl.
Figure 12:
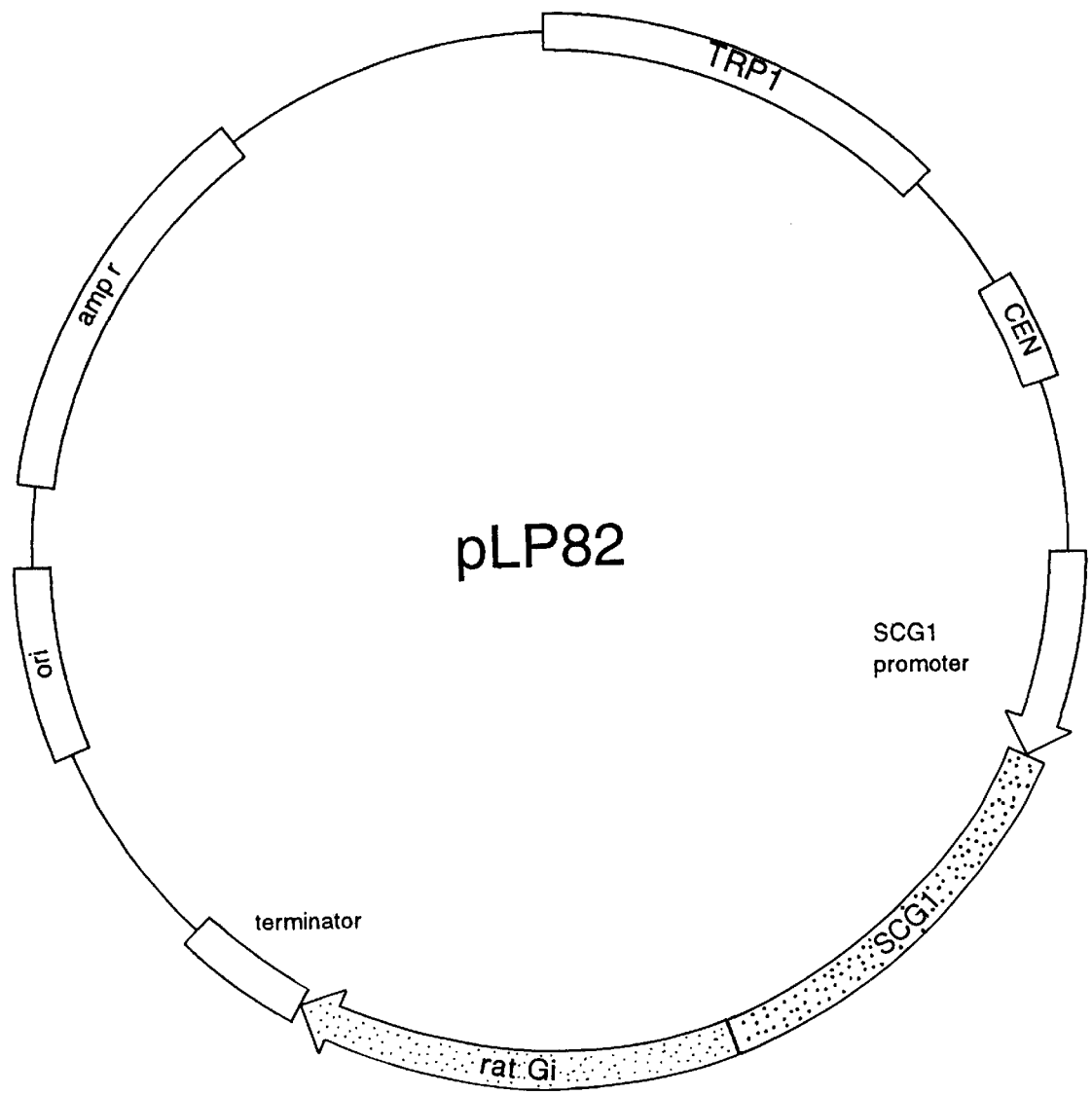
FIG. 12 G protein expression plasmid, pLP82.

Yeast strains that respond to somatostatin are created by introducing several modifications into typical laboratory yeast strains. First, a cDNA encoding the somatostatin receptor subtype 2 (SSTR2) is placed under the control of the galactose-inducible GAL1 promoter in a multicopy yeast plasmid (FIG. 11). High level expression of receptor is accomplished by inducible co-overexpression of the transcriptional activating protein GAL4 from the same plasmid. Second, the endogenous Gα protein gene, GPAI/SCG1, is replaced with a chimeric gene composed of an amino terminal domain from GPAI/SCG1, and C-terminal sequences from rat Gαi2 (FIG. 12). Expression of chimeric G proteins in yeast have previously been shown to suppress the growth defect of scgl/gpal mutant cells [Kang, Y. S., Kane, J., Kurjan, J., Stadel, J. M., and Tipper, D. J. (1990) Mol. Cell. Biol. 10, 2582–2590]. Third, the FAR1 gene is deleted, permitting continued growth in the presence of an activated mating signal transduction pathway. The FAR1 protein is thought to serve as the primary interface between the mating signal transduction pathway and cell cycle machinery (Chang, F. and Herskowitz, I. (1990) Cell 63, 999–1012; Peter, M., Gartner, A., Horecka, J., Ammerer, G., and Herskowitz, I. (1993) Cell. Biol. 13, 5659–5669]. Fourth, the FUSI gene is replaced with a reporter gene construct made by fusing transcription control elements of the FUS1 gene to HIS3 protein coding sequences, thereby placing expression of the HIS3 gene product under the control of the pheromone signal transduction pathway. Yeast strains (his3) bearing this construct are able to grow poorly on supplemented minimal medium lacking histidine and are sensitive to 3-amino-1,2,4-triazole (AT), an inhibitor of the HIS3 gene product. Receptor activation by agonist-binding leads to increased HIS3 protein expression, a corresponding increase in resistance to AT, and, therefore, the ability to grow on medium lacking histidine and/or in the presence of the inhibitor. Adjusting the pH of the growth medium to >pH 5.5 enhances the ability of such cells to grow in presence of agonist, presumably due to an increased ability of somatostatin to bind to SSTR2.

Figure 13A:
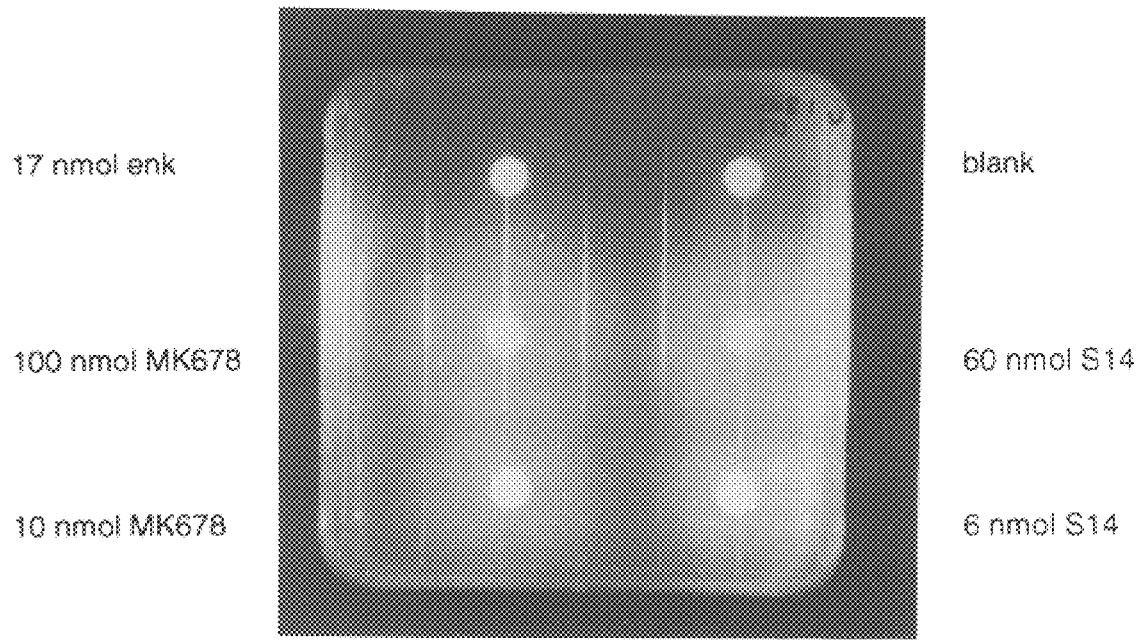
FIG. 13 (A&B). Dose dependent growth response of yeast cells to somatostatin. Cultures of yeast strain LY268 are embedded in agar (top plate) or spread evenly on the surface of agar plates (bottom plate) and exposed to the indicated amounts of designated compounds spotted on paper disks placed on top of the agar. Plates are incubated at 30° C.
Figure 13B:
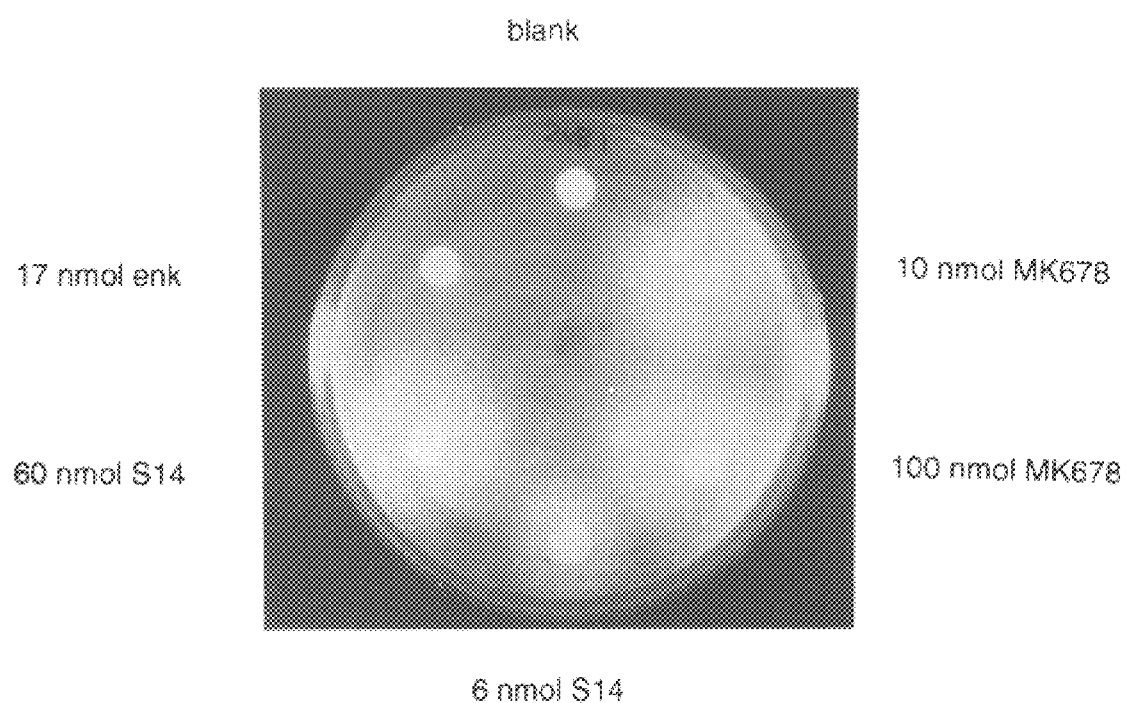

The utility of the yeast expression system lies in its adaptability to rapid mass screening. To facilitate screening for novel therapeutics directed at the SSTRs, a convenient agar plate bioassay is developed in which functional coupling of somatostatin binding to receptor and subsequent activation of the mating signal transduction pathway is detected as a zone of growth (halo) around applied compounds (FIG. 13). overnight liquid cultures of LY268 [a derivative of YPH500 (Stratagene) MATa ura3–52 ys2–801 ade2 trplΔ63 his3Δ200 leu2Δ1 far1ΔLYS2 scg1ΔhisG fus1ΔFUS1-HIS3 sst2ΔADE2 bearing the SSTR2 expression plasmid and the SCG1-Gαi2 expression plasmid pLP82 in SC dextrose (2%) lacking ura, trp were transferred to SC Lactate medium (2%) lacking ura and trp and subsequently SC galactose (2%) medium lacking ura and trp. Cells ($2 \times 10^5$) are then plated in 30 ml of SC galactose (2%) lacking ura, trp, and his agar (FIG. 13, top-panel), or spread evenly on the surface (FIG. 13, bottom panel), the indicated amounts of selected compounds applied to paper disks situated on the surface of the agar plate, and incubated at 30° C. for 3–5 days. Halos of growth are observed around disks saturated with varying concentrations of somatostatin (S-14) and MK678 [a hexapeptide analog of somatostatin that exhibits high affinity binding to SSTR2 [Verber, D., Saperstein, R., Nutt, R., Friedinger, R., Brady, P., Curley, P., Perlov, D., Paleveda, W., Zacchei, A., Cordes, E., Anderson, P., and Hirschmann, R. (1981) Life Sci, 35, 1371–1378]. Halo size increases in proportion to the amount of agonist applied and a significant response is observed even at the lowest amount applied (6 nmol S-14), demonstrating the exquisite sensitivity of the assay. No detectable response is observed with carrier alone, or to metenkephalin, an opiate receptor agonist, demonstrating the high specificity of the assay.

Yeast medium and culture conditions are formulated according to standard procedures and DNA-mediated transformation of yeast is by the LiAc method [Sherman, F., Fink, G. R., and Hicks, J. B. (1986) Methods in Yeast Genetics (Cold Spring Harbor Laboratory Press]. LY268 is constructed by sequential insertional deletion using recombinant scgl:ΔhisG, far1ΔLYS2, FUS1ΔHIS3, and sst2ΔADE2 alleles. The scg1ΔhisG allele is assembled by inserting the hisG-URA3-hisG fragment from pNKY51 [Alani, E., Cao, L., and Kleckner, N. (1987) Genetics 116, 541–5451 between the 5' EcoRI-HindIII and 3' SphI-SnaBI fragments of SCG1/GPA1. After DNA-mediated transformation of appropriate yeast strains and selections for replacement of the chromosomal allele, the URA3 gene is removed by inducing recombination between hisG repeats by growth on 5-fluoroorotic acid (FOA)-containing medium [Boeke, J., Lacroute, F., and Fink, G. (1984) Mol. Gen. Genet. 197, 345–346]. The far1ΔLYS2 allele is constructed by amplifying two fragments of the FAR1 gene [Chang, F. and Herskowitz, I. (1990) Cell 63, 999–1012] from yeast genomic DNA (strain YPH501, Stratagene) using synthetic oligonucleotides that introduce an EcoRI site at 1201 in the 5' fragment and an HindIII site at position 2017 and a SalI site at 2821 in the 3' fragment. The fragments are cloned into the EcoRI/SalI fragment of pBSK (Stratagene) . The completed far1ΔLYS2 construct is digested with EcoRI and used to transform yeast. An EcoRI fragment encoding the FUS1-HIS3 reporter gene is released from pSL1497 [Stevenson, B. J., Rhodes, N., Errede, B., and Sprague, G. F. (1992) Genes Dev. 6, 12931 and used to transform appropriate yeast strains. The sst2ΔADE2 allele [Dietzel, C. and Kurjan, J. (1987) Mol. Cell. Biol. 7, 4169–4177]is built from a 2.5 kb fragment of the ADE2 gene amplified by PCR using oligos that placed a Cla site at position 1 and an NheI site at position 2518. This fragment is used to replace the internal ClaI-NheI fragment in SST2. The sst2ΔADE2 fragment is released by digestion with SalI and used to transform appropriate yeast strains.

The multistep construction of the SSTR2 expression plasmid, pJH2 (FIG. 11), is initiated by inserting a SphI/NarI fragment of 3' untranslated region from the STE7 gene [Teague, M. A., Chaleff, D. T., and Errede, B. (1986) Proc. Natl. Acad. Sci. USA 83, 7371–7375], and an EcoRI/BamHI fragment of the GAL1/10 promoter [Yocum, R. R., Hanley, S., West, R., and Ptashne, M. (1984) Mol. Cell. Biol. 4 1985–1998] into appropriate sites in YEp352 [Hill, J. E., Myers 2, A. M., Koerner, T. J., and Tzagoloff, (1986) Yeast 2, 163–167.], creating pEK1. A PCR product, encoding the open reading frame and transcriptional termination sequences of the GAL4 gene, is amplified with oligos containing 5' EcoRI and 3' AatII sites and inserted into pEKl, creating pMP3. The cDNA encoding rat SSTR2 (Strnad, J., Eppler, C. M., Corbett, M., and Hadcock, J. R. (1993) BBRC 191, 968–976] is modified by PCR using oligonucleotides that add a BglII site in the DNA sequences encoding the amino terminus of SSTR2 and a BglII site directly after the translational stop site. SSTR2 coding sequences are inserted as a BglII PCR fragment into the BamHI site of pMP3.

Plasmid pLP82 (FIG. 12) is constructed by first replacing the XhoI/EcoRI promoter fragment in pPGKH-SCG1-Gαs [Kang, Y. S., Kane, J., Kurjan, J., Stadel, J. M., and Tipper, D. J. (1990) Mol. Cell. Biol. 10, 2582–2590], with a modified SCG1 promoter fragment [Dietzel, C. and Kurjan, J. (1987) Cell 50, 1001–1010] amplified from yeast genomic DNA using oligonucleotides that introduce 5' XhoI and 3' EcoRI sites at positions −200 and −42, forming plasmid pLP61. The BamHI fragment encoding Gα s domain is replaced with a comparable fragment encoding Gαi2, forming plasmid pLP71. The XhoI/SalI fragment of pLP71 encoding an SCGI-Gαi2 chimeric G protein expressed under the control of the SCG1 promoter is transferred to the SalI site in pRS414 (Stratagene), forming pLP82.

Plasmid pLP83 is constructed by replacing the EcoRI fragment in pLP71 with the EcoRI fragment encoding I from pPGKH-SCG1 [Kang, Y. S., Kane, J., Kurjan, J., Stadel, J. M., and Tipper, D. J. (1990) Mol. Cell. Biol. 10, 2582–2590], forming plasmid pLP75. The XhoI/SalI fragment encoding SCG1 is transferred to the SalI site in pRS414 (Stratagene), forming plasmid pLP83.

EXAMPLE 4

Effects of G protein expression on the sensitivity of the bioassay

Figures 14A, 14B:
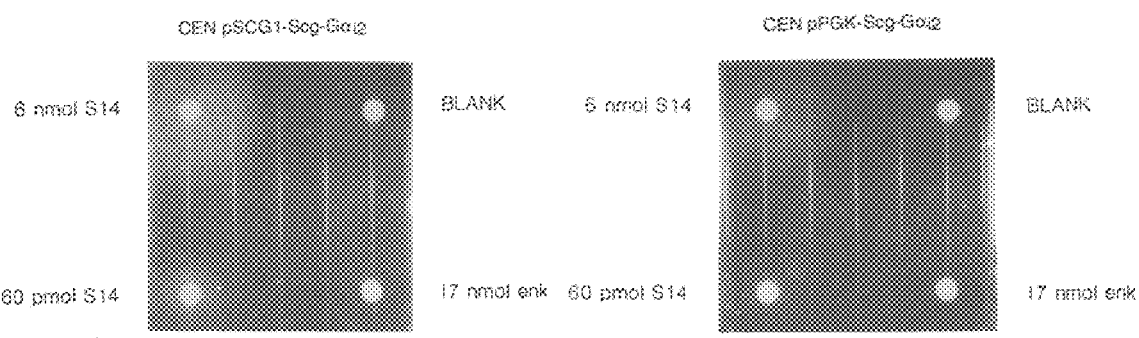
FIG. 14(A,B,C,&D). Growth response of yeast strains exposed to somatostatin is dependent on amount of chimeric G protein expressed. Cultures of yeast strains described in the text are embedded in agar and exposed to the indicated amounts of designated compounds spotted on paper disks placed on top of the agar. Plates are incubated at 30° C.
Figures 14C, 14D:
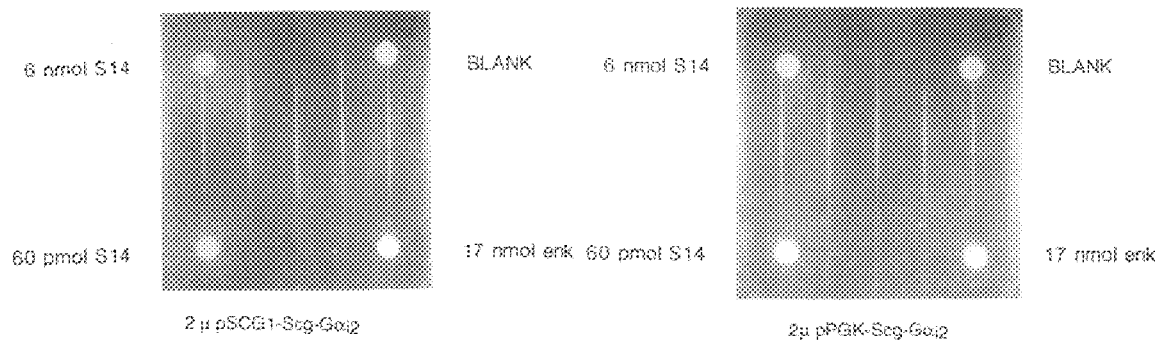

Yeast strains LY268 (pLP82: CEN pSCG1-Scg1-Gαi2), LY262 (pRS414-PGK-Scg1-Gαi2: pRS414 containing the PGK-Scg1-Gαi2 Xho/SalI fragment from pPGKH-Scg1-Gαi2 in the SalI site), LY324 (pLP84:2μ pSCG1-Scg-Gαi2), and LY284 (pRS424-PGK-Scg-Gαi2: pRS424 containing the PGK-Scg1-Gαi2 Xho/SalI fragment from pPGKH-Scg1-Gαi2 in the SalI site) were constructed by placing the designated plasmids in strain LY260 (a. derivative of YPH500 (Stratagene) MATa ura 3–52 lys2–801 ade2 trp1D63 his3Δ200 leu2α1 far1ΔLYS2 scg1ΔhisG fus1ΔFUS1-HIS3 sst2ΔADE2 bearing the SSTR2 expression plasmid]. Overnight liquid cultures in SC-Dextrose (2%) lacking ura and trp were transferred to Sc-Lactate (2%) medium lacking ura and trp and subsequently SC-Glactose (2%) medium lacking ura and trp. Cells (2×10$^5$) are then plated in 30 ml of SC-Gα lactose (2%) lacking ura, trp, and his agar, the indicated amounts of selected compounds applied to paper disks situated on the surface of the agar plate, and incubated at 30° C. for 3–5 days (FIG. 14). The extent of growth around S-14 is dependent upon the G protein expression plasmid contained in each strain. The most luxuriant growth is observed in response to S-14 by LY268 (pLP82: CEN pSCG1-Scg1-Gαi2), less growth is seen in strainy LY262 (pRS414-PGK-Scg1-Gαi2) and LY324 (pLP84: 2μ pSCG1-Scg-Gαi2), while little detectable growth is exhibited by LY284 (pRS424-PGK-Scg1-Gαi2). These results are consistent with the observed inhibition of pheromone stimulated transcriptional induction by elevated amounts of expressed Gα protein. Thus, precise regulation of G protein expression levels in strains expressing heterologous G protein-coupled receptors is critical to the design and successful implementation of a bioassay for compounds that interact with the receptor.

Plasmid pLP84 is constructed by first replacing the XhoI/EcoRI promoter fragment in pPGKH-SCG1-Gα$_s$ [Kang, Y. S., Kane, J., Kurjan, J., Stadel, J. M., and Tipper, D. J. (1990) Mol. Cell. Biol. 10, 2582–2590], with a modified SCG1 promoter fragment [Dietzel, C. and Kurjan, J. (1987) Cell 50, 1001–1010] amplified from yeast genomic DNA using oligonucleotides that introduce 5' XhoI and 3' EcoRI sites at positions –200 and –42, forming plasmid pLP61. The BamHI fragment encoding Gα$_s$ domain is replaced with a comparable fragment encoding Gα$_{12}$ forming plasmid pLP71. The XhoI/SalI fragment of pLP71 encoding a SCG1-Gα$_{12}$ chimeric G protein expressed under the control of the SCGI promoter is transferred to the SalI site in pRS424 (Stratagene), forming pLP84.

EXAMPLE 5

Somatostatin receptor is capable of transmitting signal through the endogenous yeast G α

Figures 15A, 15B:
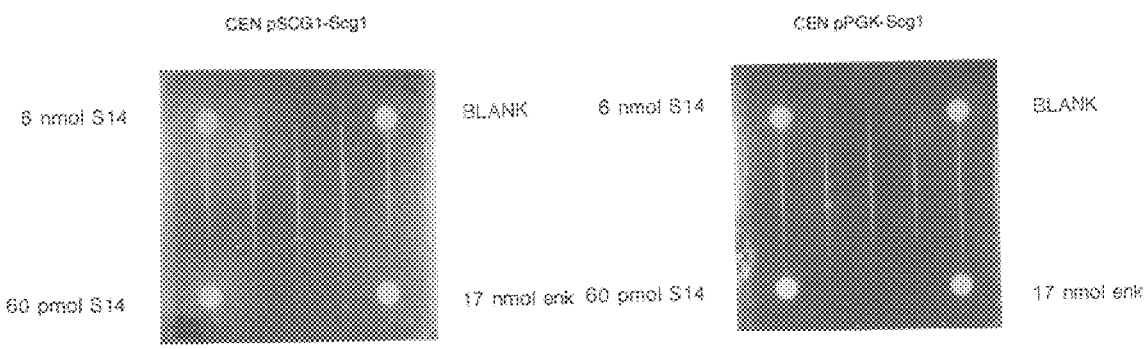
FIG. 15 (A,B,C, &D) Growth response of yeast strains exposed to somatostatin is dependent on amount of yeast G protein expressed. Cultures of yeast strains described in the text are embedded in agar and exposed to the indicated amounts of designated compounds spotted on paper disks placed on top of the agar. Plates are incubated at 30° C.
Figures 15C, 15D:
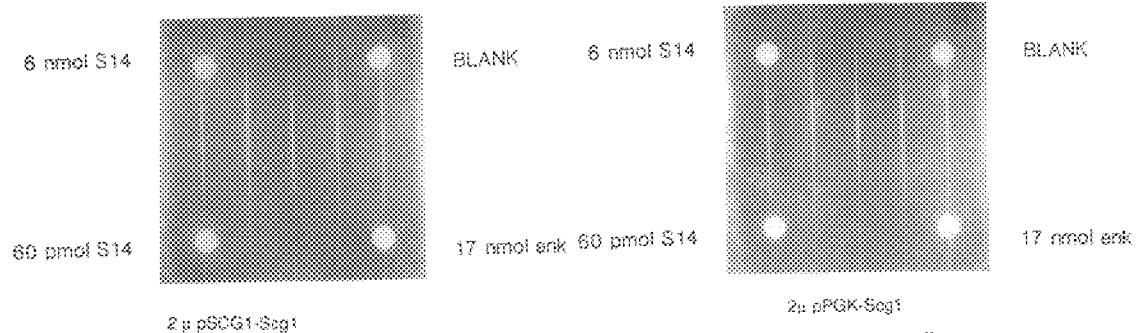

SSTR2 is thought to couple to Gα$_{12}$ and Gα$_{13}$ in mammalian cells [Luthin, D. R., Eppler, C. M., and Linden, J. (1993) J. Biol. Chem. 26B, 5990–5996]. However, when expressed in appropriate yeast strains (described below), SSTR2 is shown to be capable of transmitting a signal through the endogenous yeast Gα protein. Implicit in this observation is the necessary coupling of SSTR2 to the endogenous Gα protein. The ability of heterologous G protein-coupled receptors to couple to the endogenous Gα protein is a significant improvement in existing technology, and is thought not to be possible in the prior art (King K. Dohlman, H. G., Thorner, J., Caron, M. G., and Lefkowitz, R. J. (1990) Science 250, 121–123). Yeast strains LY266 (pLP83: CEN pSCG1-Scgl), LY280 (pRS414-PGK-Scgl: pRS414 containing the PGK-Scgl Xho-SalI fragment from pPGKH-ScgI in the SalI site), LY326 (pLP86: 2μ p SCG1-Scg), and LY282 (pRS424-pPGK-Scg pRS424 containing the PGK-Scgl Xho-SalI fragment from pPGKH-Scgl in the SalI site) were constructed by placing the designated plasmids in strain LY260. Overnight liquid cultures of these strains, which are capable of expressing only SCG1/GPAI, in SC-Dextrose (2%) lacking ura and trp were transferred to SC-Lactate (2%) lacking ura, trp, and subsequently to SC-Glactose (2%) lacking ura and trp medium. Cells (2×10$^5$) are then plated in 30 ml SC-Glactose (2%) lacking ura, trp, and his medium, the indicated amounts of selected compounds applied to paper disks situated on the surface of the agar plate, and incubated at 30° C. for 3–5 days. Halos of growth are observed around disks saturated with varying concentrations of S-14, demonstrating that a productive signal can be transduced through an interaction between SSTR2 and the yeast SCGI/GPAL protein (FIG. 15). These observations demonstrate that a simple and broadly applicable bioassay may be established in which any member of the class of G protein-coupled receptors may be expressed in appropriately modified yeast strains and made to couple to the endogenous Gα protein.

Plasmid pLP86 is constructed by replacing the EcoRI fragment in pLP71 with the EcoRI fragment encoding SCG1 from pPGKH-SCGl [Kang, Y. S., Kane, J., Kurjan, J., Stadel, J. M., and Tipper, D. J. (1990) Mol. Cell. Biol. 10. 25B2–2590], forming plasmid pLP75. The XhoI/SalI fragment - encoding SCGl is transferred to the SalI site in pRS424 (Stratagene), forming pLP86.

EXAMPLE 6

Mutations in SST2 enhance the sensitivity of the response to somatostatin

Figures 16A, 16B:
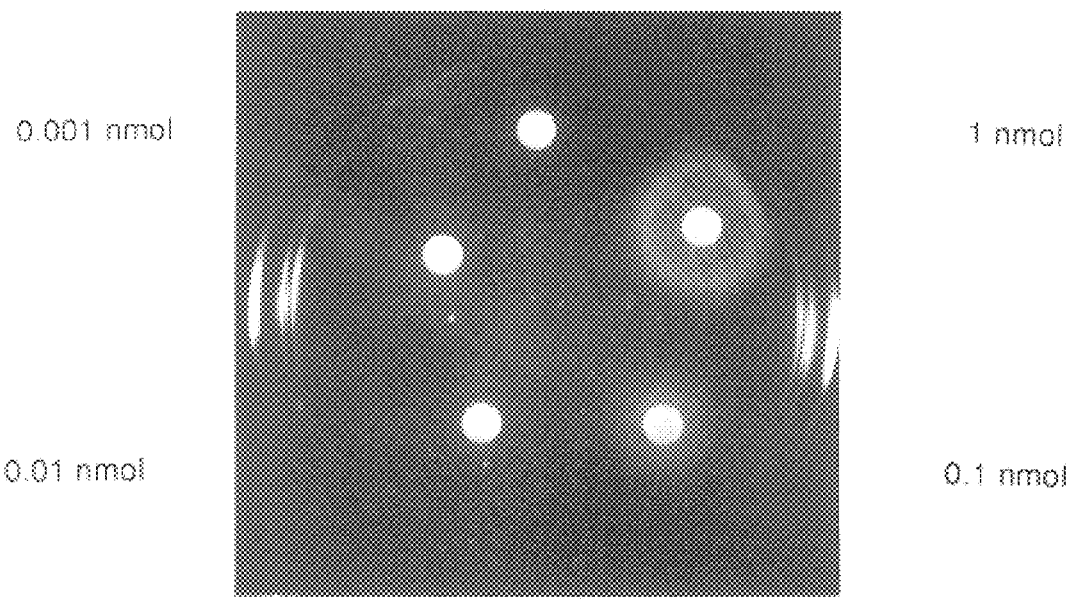
FIG. 16 (A&B). Yeast cells bearing a mutation in the sst2 gene exhibit elevated resistance to AT when exposed to mating pheromone. Cultures of yeast strains are embedded in agar and exposed to the indicated amounts of a mating factor spotted on paper disks placed on top of the agar. Plates are incubated at 30° C.

Mutations in the SST2 gene result in supersensitivity of otherwise wild type cells to mating pheromone. The effect of this mutation on levels of AT resistance expressed in far1, FUS1 -HIS3 strains is examined (FIG. 16). Cells (5×10$^5$) from overnight cultures of LY230 [a derivative of YPH50 (Statagene) MATa SST2 ura 3–52 lys2–801 ade2 trp1Δ63 his3Δ200 leu2Δ1 far1ΔFUS1 -HIS3] and LY238 (a modification of LY230 sst2ΔADE2) in SCD-ura, trp are plated on SCD-ura, trp, his, containing 10 mM AT and incubated at 30° C. for 2 days. Increased AT resistance in response to mating factor is exhibited by LY238 (sst2). Growth of LY238 is observed around disks containing 10 pmol of mating pheromone, while LY230 (SST2) required 1 nmol of mating factor for significant growth to be observed. Thus, introduction of sst2 into these strains raises the sensitivity of the bioassay by at least 100-fold, opening the possibility of increasing the sensitivity of other G protein-coupled receptor bioassays as well.

Figures 17A, 17B:
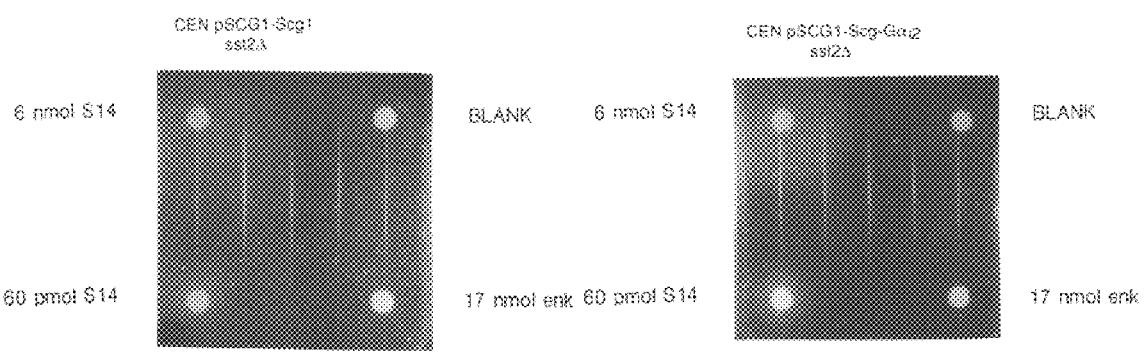
FIG. 17 (A,B,C,&D). A mutation in the sst2 gene enhances the growth of the yeast cells exposed to somatostatin. Cultures of yeast strains described in the text are embedded in agar and exposed to the indicated amounts of designated compounds spotted on paper disks placed on top of the agar. Plates are incubated at 30° C.
Figures 17C, 17D:
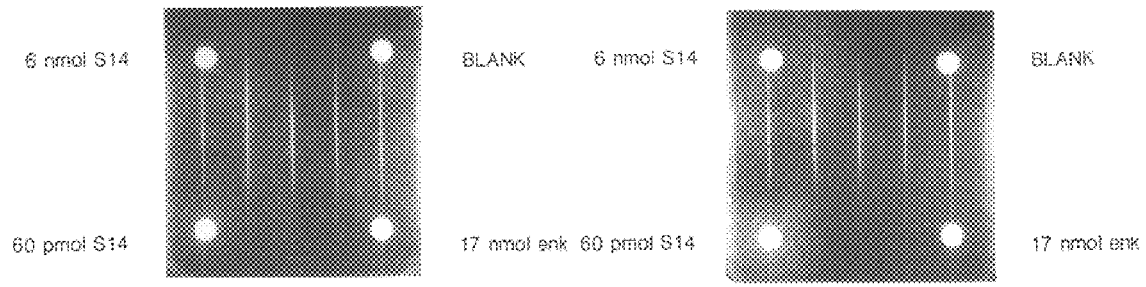

Yeast strains that express SSTR2 and bearing a defective sst2 gene exhibit much greater growth around disks containing various concentrations of somatostatin than is exhibited by strains containing a functional SST2 gene. Overnight cultures of strains LY268 (sst2, containing pLP82), LY266 (sst2, containing pLP83), LY288 [a derivative of YPH500 (Stratagene) MATa SST2 ura3–52 lys2–801 ade2 trp1Δ63 his3Δ200 leu2Δ1 far1ΔLYS2 scg1ΔhisG fus1ΔFUS1-HIS3 bearing the SSTR2 expression plasmid and the SCG1-G$\alpha_{12}$ expression plasmid, pLP82] and LY290 (a modification of LY288 that contains pLP83) in SC Dextrose (2%) lacking ura, trp were transferred to SC Lactate medium (2%) lacking ura and trp, and subsequently to SC Glactose (2%) medium lacking ura and trp. Cells ($2\times10^5$) are then plated in 30 ml SC Glactose (2%) plates lacking ura, trp and his, the indicated amounts of selected compounds applied to paper disks situated on the surface of the agar plate, and incubated at 30° C. for 3–5 days. Halos of growth are observed around disks saturated with varying concentrations of S-14 in both sst2Δ and SST2 strains (FIG. 17), however, the amount of growth exhibited by strain LY268 and LY266 (sst2) is significantly greater than that observed for strains LY288 and LY290 (SST2). Furthermore, the down-regulatory effect of SST2 is more pronounced in those strains that express solely the wild type SCG1/GPA1 protein, consistent with the expectation that SST2 interacts more faithfully with the native protein than the SCG1-G$\alpha_{12}$chimeric protein.

EXAMPLE 7

Functional expression of a rat cholecystokinin ($CCK_B$) receptor in yeast

Cholecystokinin (CCK) is a major intestinal hormone that plays an important role in regulating pancreatic secretion and bile ejection (1). CCK is also one of the most widely distributed of brain neuropeptides (2). CCK promotes its effects through the action of cell surface receptors which can be classified using pharmacological criteria into two subtypes, $CCK_A$ and $CCK_B$ (3). Molecular cloning efforts have identified cDNAs encoding G protein-coupled $CCK_A$ (4) and $CCK_B$ (5–8) receptors. Recently, compounds with selective $CCK_B$ receptor antagonist properties having potent anxiolytic activity have been identified (9). Functional expression of $CCK_B$ receptors in yeast should permit rapid screening for new compounds with $CCK_B$ antagonist properties and facilitate molecular characterization of structural aspects of the $CCK_B$ receptor required for rational design of new $CCK_B$ ligands.

Materials and Methods

Plasmid constructions. All molecular biological manipulations were performed according to standard procedures (10). The rat $CCK_B$ receptor was cloned from rat brain cDNA by PCR using oligonucleotide primers that introduce BglII sites at 5' and 3' ends (5-AAAAGATCTAAA, ATGGACCTGCC,TAAGCTG, (SEQ. ID NO:1) 3'AAAAGATCTTCAGCCAGG CCCCAGTGTGCT(SEQ. ID NO:2). The CcK$_9$ receptor expression plasmid, pJH20, was constructed by inserting the BglII-digested PCR fragment in the correct orientation into BamHI cut pMP3 (11). The Gα protein expression plasmids used in this study were constructed by replacing DNA sequences encoding the 47 carboxy-terminal amino acids of GPA1 in pLPB3 (11) with those of G, (pLP122), G$\alpha_{i2}$ (pLP121)

Strain Constructions

Yeast strains were constructed, and growth media and culture conditions formulated according to standard procedures (12). DNA-mediated transformation of yeast was carried out using the lithium acetate method. The yeast strains used as the basis for all experiments described in this report were constructed by sequential insertional deletion using recombinant alleles. Yeast strains that express the rat $CCK_5$ receptor were constructed by sequential DNA-mediated transformation of LY296 (MATa ura3–52 trp1Δ63 his3Δ200 leu2Δ1 ade2–101 lys2–801 gpa1ΔhisG far1ΔLYS2 FUS1-HIS3 sst2ΔADE2, ref. 7) with pJH20 followed by the Gα protein expression plasmids described above.

Radiolabeled agonist saturation binding assays. Crude yeast membrane extracts from late log phase cultures were prepared by glass-bead lysis and centrifugation at 40,000 xg following a published procedure (13). The protein content of crude membrane fractions was measured using the Biorad protein assay kit according to manufacturers instructions. Radioligand binding assays were conducted according to Strnad et al (14) using $^3$H-CCK-8 (Amersham) in the presence of 150 mM NaCl. Non-specific binding was defined as that observed in the presence of 1 μM CCK-4. Negligible specific binding was observed in membrane fractions made from cells lacking $CCK_B$ receptor (data not shown).

Bioassay.

Functional assay of $CCK_B$ receptor expressed in yeast was accomplished using modification of a standard procedure (11). Yeast strains were grown overnight in 2 ml synthetic complete liquid medium containing glucose (2%) and lacking uracil and tryptophan (SCD-ura-trp) medium, washed to remove residual glucose and grown overnight in 5 ml SC Glactose (2%)-ura-trp liquid medium. Molten (50° C.) SC Glactose (2%)-ura-trp-his agar medium (30 ml, adjusted to pH 6.8 by addition of concentrated KOH or NH,OH prior to autoclaving) was inoculated with the overnight culture ($2\times10^4$ cells/ml) and poured into square (9×9 cm) petri plates. Sterile filter disks were placed on the surface of the solidified agar and saturated with 10 μl of DMSO containing the indicated amounts of the designated compounds. Plates were incubated at 30° C. for 3 days. Cholecystokinins (CCK-4, CCK-8), somatostatin (S-14), and met-enkephalin were from Bachem. Oxymetazoline, isoproterenol, and carbachol were from Sigma.

RESULTS

Figure 18:
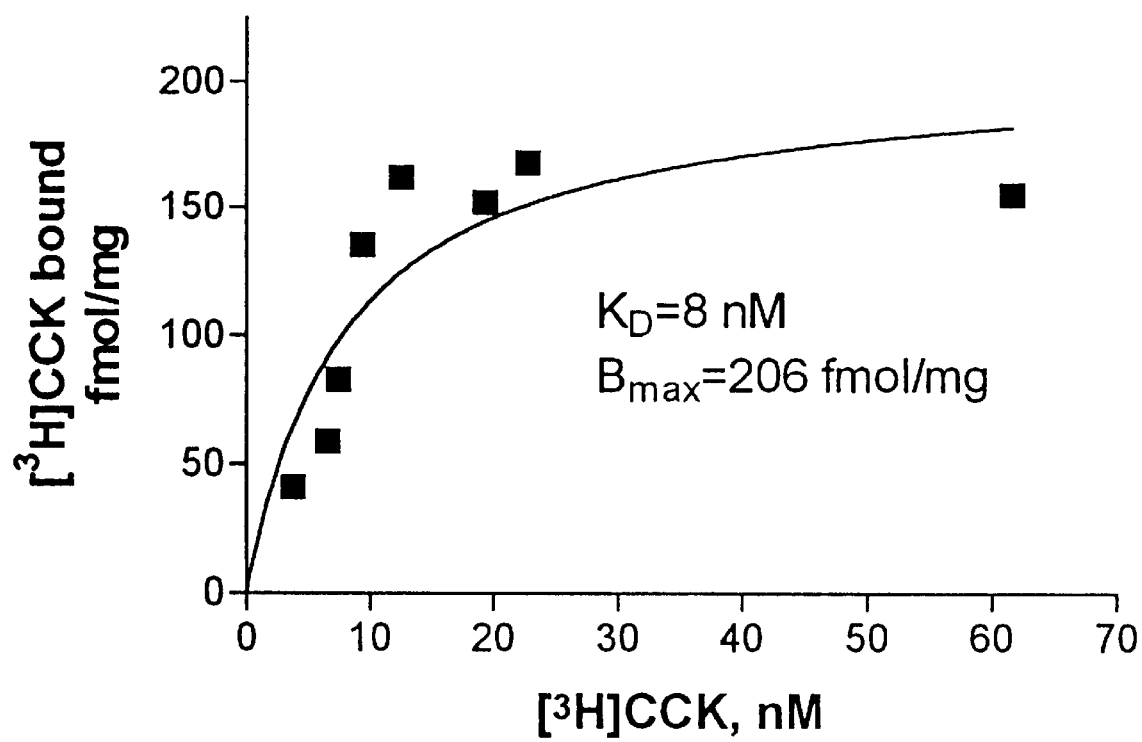
FIG. 18. Ligand-binding to the rat $CCK_B$ receptor expressed in yeast. Crude membrane fractions from overnight liquid cultures of LY631 cells were prepared, and agonist saturation binding assays conducted as described in Methods and Materials. Saturation binding was performed with 4–60 nM[$^3$H] CCK-8 (25 µg protein/tube). Non-specific binding for each point as cpm bound in the presence of 1 µM cold CCK-8 ranged from 20 to 60%. Displayed is a representative experiment performed in duplicate.

Cholecystokinin binding to the rat $CCK_B$ receptor expressed in yeast. High level functional expression of the rat $CCK_B$ receptor in yeast was a necessary prerequisite to the development of a useful bioassay. The rat $CCK_B$ receptor cDNA was placed under the control of the GAL1 promoter in plasmid pJH20. This construct also confers inducible overexpression of Gal4p, the transcriptional activating protein for galactose-inducible genes, resulting in significantly elevated levels of receptor protein in crude membrane fractions compared to receptor expressed from a plasmid lacking GAL4 sequences (data not shown). $CCK_B$receptor sequences were introduced into pJH20 without modification of the protein coding sequences. Previously, King et al. reported that replacement of the amino-terminal domain of the β$_2$-adrenergic receptor with equivalent STE2 sequence was necessary for efficient receptor expression in yeast (15). In contrast, functional expression of $CCK_B$receptor in yeast does not require addition of any yeast sequences to the amino-terminus. Plasmids conferring expression of chimeric Gα proteins composed of amino-terminal βY-interaction domain from Gpa1p and carboxy-terminal receptor interaction domains from rat G$\alpha_{12}$ (pLP121) or G$\alpha_5$ (pLP122) under the control of the GPAL promoter were constructed. Yeast strains that contain expressed $CCK_B$ receptor and chimeric G$\alpha_{12}$ (LY628) and G$\alpha_5$ (LY631) protein were assembled by transformation of a yeast strain (LY296) modified by deletion of genes encoding components of the mating signal transduction pathway with $CCK_B$ receptor and Gα protein expression plasmids. Most G protein-coupled receptors exhibit both high and low agonist-dependent affinity states. High-affinity agonist binding is dependent on functional association of receptor with a heterotrimeric G protein. If the receptor does not associate with, or is uncoupled from the G protein, agonist binding will be of low affinity and undetectable in radiolabeled agonist saturation binding assays. In crude yeast membrane fractions made from LY631 cells, the agonist $^3$H-CCK-8 bound to the $CCK_B$ receptor with high affinity and in a saturable manner (FIG. 18), demonstrating that (1) a functional ligand-binding conformation of the $CCK_B$ receptor was expressed in yeast, and (2) the receptor functionally associated with the chimeric Gα protein, resulting in a high-affinity agonist binding state. The $CCK_B$ receptor expressed in yeast displayed an affinity for $^3$H-CCK-8 ($K_d$=8 nM) substantially lower than the high affinity binding state of the $CCK_B$ receptor expressed in mammalian cells ($K_d$=100 pM, ref. 5), perhaps due to an inefficient interaction with the receptor interaction domain from rat $Gα_5$ These binding parameters would be expected to more closely resemble the native values in extracts from cells containing the cognate Gα protein, Gαq (5–8). The total number of $^3$H-CCK-8 binding sites observed ($B_{max}$=206 fmol/mg) was consistent with values obtained for the yeast α-mating pheromone receptor (200 fmol/mg, ref. 16). For many G protein-coupled receptors, high affinity agonist binding is sensitive to GTP and its analogs. GTP analogs induce dissociation of the receptor/G-protein complex, resulting in a low affinity agonist binding state. Addition of GppNHp (100 μM), a non-hydrolyzable GTP analog, to an agonist binding assay decreased specific binding of $^3$H-CCK-8 to the $CCK_B$ receptor by greater than 50% in crude membrane fractions from LY631 cells. These results represent a further indication of functional coupling between the $CCK_B$ receptor and the chimeric Gα protein. Thus, the rat $CCK_B$ receptor expressed in yeast exhibits high-affinity agonist binding properties comparable to those observed in mammalian tissues.

Figure 19A:
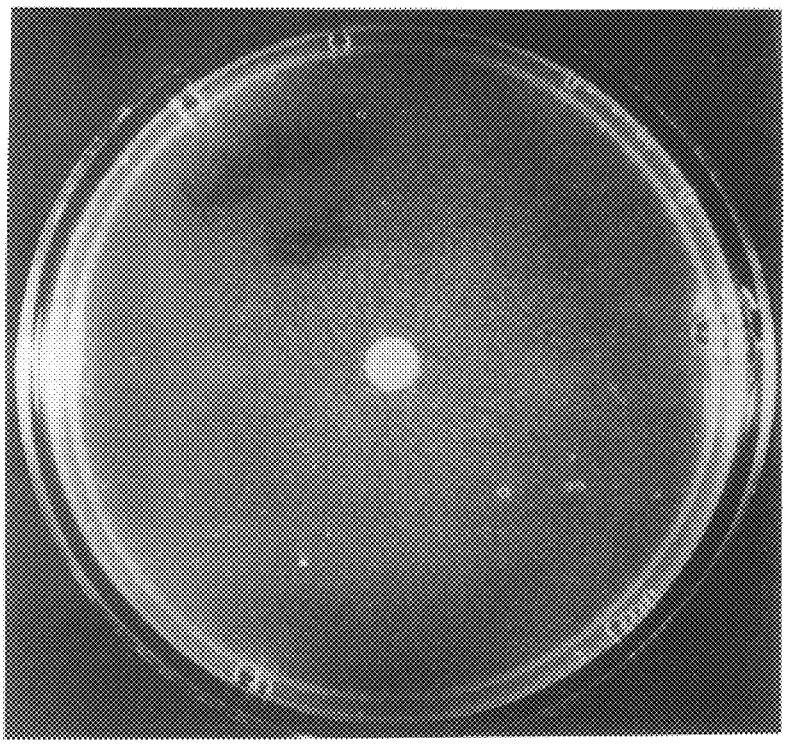
FIG. 19 (A&B). Growth of yeast in response to $CCK_B$ receptor agonists. Yeast strains that functionally express the rat $CCK_B$ receptor (LY628, LLY631) were cultured as described in Materials and Methods were plated in SC Galactose (2%)-ura, trp, his agar medium (2×10$^4$ cells/ml). Sterile filter disks were placed on the surface of the solidified agar and saturated with 10 µl of DMSO containing 10 µl amounts of the indicated compounds. The plates were then incubated at 30° C. for 3 days. (A) CCK-6, (B) CCK-4.
Figure 19B:
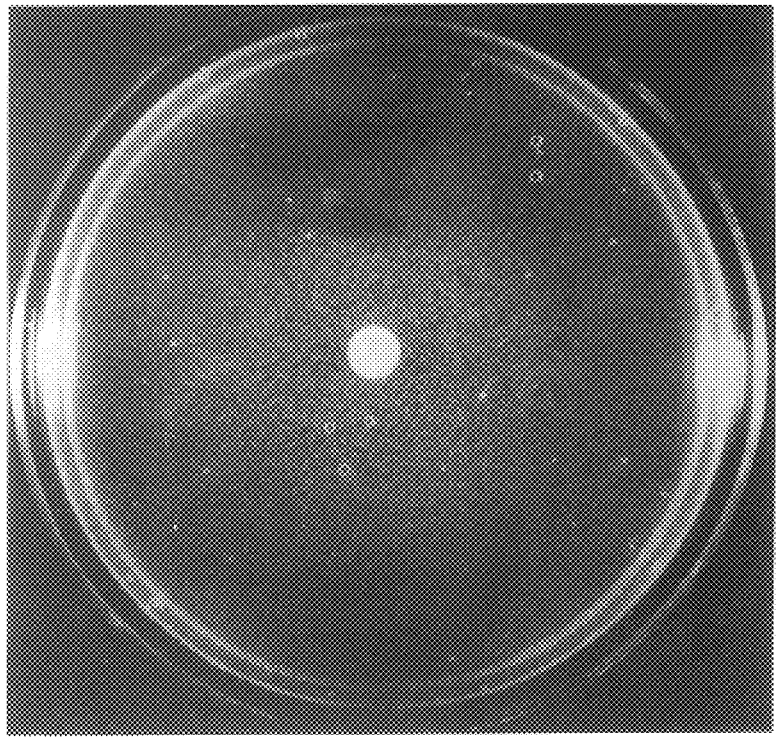

The $CCK_B$ receptor retained agonist selectivity when expressed in yeast. A selective and sensitive bioassay was designed using yeast strains bearing the above described genetic modifications and plasmids conferring expression of the $CCK_B$ receptor and chimeric $G_{αi2}$ and $G_{α5}$ proteins. A dose-dependent growth response of LY628 and LY631 cells was evident around applied CCK-4 (FIG. 19). The assay was selective: the diameter of the growth zones was proportional to the reported affinity of the ligands for the $CCK_B$ receptor (CCK-8>gastrin>CCK-4) reflecting the ability of the bioassay to discriminate between ligands of varying potency (5–8). Detectable growth responses were not observed in response to a variety of agonists selective for other G protein-coupled receptors (somatostatin, metenkephalin, oxymetazoline, isoproterenol, carbachol), nor by yeast cells lacking the $CCK_B$ receptor (data not shown). A detectable response was observed to 10 μg of CCK-4.

DISCUSSION Compounds that act at the CCK receptors, particularly antagonists, may possess great therapeutic potential (3). In the periphery, the inhibitory effects of CCK antagonists make them excellent candidates for treatment of pancreatitis, pancreatic cancer, biliary colic, disorders of gastric emptying, and irritable bowel syndrome. CCK antagonists reverse the development of satiety and might be useful in improving appetite in anorectic patients or others that require increased food intake. Conversely, CCK ago-nists might be useful appetite suppressants. CCK antagonists also potentiate opiate analgesia and so might be appropriate for use in the management of clinical pain. In the CNS, selective CCK antagonists have promise as powerful anxiolytic agents (9). Further, CCK antagonists relieve the anxiety associated with withdrawal from drug use, and so might find a use in the treatment of withdrawal from commonly abused drugs. CCK agonists may have use as antipsychotic agents.

REFERENCES CITED IN THIS EXAMPLE

1. Ivy, A. C. and E. Oldberg. 1928. J. Physiol. (London) 86: 599–613.

2. Dockray, G. J. R. 1976. Immunochemical evidence of cholecystokinin-like peptides in brain. Nature 264: 568–570.

3. Woodruff, G. N. and J. Hughes. 1991. Cholecystokinin antagonists. Annu. Rev. Pharmacol. Toxicol. 31: 469–501.

4. Wank, S. A, R. Harkins, R. T. Jensen, H. Shapiro, A. de Weerth, and T. Slattery. 1992. Purification, molecular cloning, and function expression of the cholecystokinin receptor from rat pancreas. Proc. Natl. Acad. Sci. USA.89: 3125–3129.

5. Kopin, A. S., Y. M. Lee, E. W. McBride, L. J. Miller, M. Liu, N. Y. Lin, L. F. Kolakowski, and M. Beinborn. 1992. Expression cloning and characterization of the canine parietal cell gastrin receptor. Proc. Natl. Acad. Sci. USA 89: 3605–3609.

6. Wank, S. A., J. R. Pisenga, and A. de Weerth. 1992. Brain and gastrointestinal cholecystokinin receptor family: Structure and function. Proc. Natl. Acad. Sci. USA 89: 8691–8695.

7. Lee, Y. M., M. Beinborn, E. W. McBride, M. Lu, L. F. Kolakowski. and A. S. Kopin 1993. The human brain cholecystokinin-B/gastrin Receptor. J. Biol. Chem. 268: 8164–8169.

8. Ito, M., T. Matsui, T. Taniguchi, T. Tsukamoto, T. Murayama, N. Arima, E. Nakata, T. Chiba, and K. Chibura. 1993. Functional characterization of a human brain cholecystokinin-B receptor. J. Biol. Chem. 268: 18300–18305.

9. Hughes, J., P. Boden, B. Costall, A. Domeney, E. Kelly, D. C. Horwell, J. C. Hunter, R. D. Pinnock, and G. N. Woodruff. 1990. Development of a class of selective cholecystokinin type B receptor antagonists having potent anxiolytic activity. Proc. Natl. Acad. Sci. USA 87: 6728–6732.

10. Sambrook, J., E. F. Fritsch, and T. Maniatis. 1989. Molecular Cloning, A Laboratory Handbook. Cold Spring Harbor Press. Cold Spring Harbor, N.Y.

11. Price, L. A., E. M. Kajkowski, J. R. Hadcock, B. A. Ozenberger, and M. H. Pausch. 1995. Yeast cell growth in response to agonist dependent activation of a mammalian somatostatin receptor. submitted.

12. Rose, M., F. Winston, and P. Hieter. 1990. Methods in Yeast Genetics. Cold Spring Harbor Press. Cold Spring Harbor, N.Y.

13. Blumer, K. J., J. E. Reneke, and J. Thorner. 1988. The STE2 gene product is the ligand-binding component of the a-factor receptor of Saccharomyces cerevisiae. J. Biol. Chem. 263: 10836–10842.

14. Strnad, J., C. M. Eppler, M. Corbett, and J. R. Hadcock. 1993. The rat SSTR2 somatostatin receptor subtype is coupled to inhibition of cyclic AMP accumulation. Biochem. Biophys. Res. Comm. 191: 968–976.

15. King, K., B. G. Dohlman, J. Thorner, M. G. Caron, and R. J. Lefkowitz. 1990. Control of yeast mating signal transduction by a mammalian $\beta_2$-adrenergic receptor and G, a subunit. Science 250: 121–123.

16. Weiner, J. L., C. Guttierez-Steil, and K. J. Blumer. 1993. Disruption of receptor-G protein coupling in yeast promotes the function of an SST2-dependent adaptation pathway. J. Biol. Chem. 268: 8070–8077.

EXAMPLE 9

Functional expression of a rat adenosine ($A_{2a}$) receptor in yeast.

Adenosine, as well as ATP and related purinergic compounds, function as both neurohormonal agents and autocoids regulating the process of cell to cell communication (1). In this role, adenosine regulates a broad range of physiological functions including heart rate and contractility, smooth muscle tone, sedation, release of neurotransmitters, platelet function, lipolysis, kidney and white blood cell action. Adenosine promotes its effects through the action of cell surface receptors which can be classified using pharmacological criteria into three subtypes, $A_1$, $A_{2a}$ and $A_{2b}$, and $A_3$. Molecular cloning efforts have identified cDNAS encoding G protein-coupled adenosine $A_1$ (2–5), $A_{2a}$ and $A_{2b}$ (6–9), and $A_3$. receptors (10). Functional expression of adenosine receptors in yeast should permit rapid screening for new compounds with adenosine agonist and antagonist properties and facilitate molecular characterization of structural aspects of the adenosine receptors required for rational design of new adenosine ligands.

MATERIALS AND METHODS

Plasmid constructions. All molecular biological manipulations were performed according to standard procedures (11). The rat $A_{2a}$-adenosine receptor (9) was cloned from rat brain cDNA by PCR using oligonucleotide primers that introduce BamHI sites at 5' and 3' ends (5' G A A G A T C T A A A A A A T G G G C T C C T C G G T G T A C, (SEQ. ID NO:3) 3-ACATGCATGCAGATCTTCAGGAAGGGGCAAACTC (SEQ. ID NO:4). The $A_{2a}$-adenosine receptor expression plasmid, pJH21, was constructed by inserting the BglII-digested PCR fragment in the correct orientation into BamHI cut pMP3 (12). For constitutive expression of the $A_{2a}$-adenosine receptor in glucose-containing medium, the expression vector, pLP100, was constructed. DNA fragments encoding transcriptional regulatory sequences from the ADHI gene (&) were amplified by PCR and inserted into pRS426. An ADHL transcriptional terminator fragment was amplified from yeast genomic DNA (YPH501, Stratagene) using synthetic oligonucleotides that add 5' XhoI (TTTCTCGAGCGAATTTCTTATGATTT(SEQ. ID NO:5)) and 3' KpnI (TTTGGTACCGGGCCCGGACGGATTACAACAGGT (SEQ. ID NO:6)) sites. An ADH1 promoter fragment was amplified from yeast genomic DNA using synthetic oligonucleotides that add 5' SacI GGGAGCTCTGATGGTGGTACATAACG(SEQ. ID NO:7)) and 3' BamHI (GGGGGATCCTGTATATGAGATAGTTGA(SEQ. ID NO:8)) sites. The $A_{2a}$-adenosine receptor expression plasmid, pLP116, was constructed by inserting a PCR fragment encoding the $A_{2a}$-adenosine receptor amplified using oligonucleotides, that add 5' BglII (AAAGATCTAAAATGGGCTCCTCGGTGTAC(SEQ. ID NO:9)) and 3' SalI (AAGTCGACTCAGGAA GGGGCAAACTC(SEQ. ID NO:10) sites BamHI-SalI cut LP100. The Go protein expression plasmids used in this study were constructed by replacing DNA sequences encoding the 47 carboxy-terminal amino acids of GPA1 in pLP83 (12) with those of $G_{\alpha 5}$ (pLP122) and $G\alpha_{12}$ (pLP121).

Strain constructions. Yeast strains were constructed, and growth media and culture conditions formulated according to standard procedures (13). DNA-mediated transformation of yeast was carried out using the lithium acetate method. The yeast strains used as the basis for all experiments described in this report were constructed by sequentional insertional deletion using recombinant alleles. Yeast strains that express the rat $A_{2a}$-adenosine receptor were constructed by sequential DNA-mediated transformation of LY296 (MATa ura3–52 trp1Δ63 his3Δ200 leu2Δ1 ade2–101 lys2–601 gpa1ΔhisG far1ΔLYS2 FUS1-HIS3 sst2ΔAΔE2, ref. 12) with $A_{2a}$, adenosine receptor expression plasmids followed by the Gα protein expression plasmids described above.

Radiolabeled agonist saturation binding assays. Crude yeast membrane extracts from late log phase cultures were prepared by glass-bead lysis and centrifugation at 40,000 xg following a published procedure (14). The protein content of crude membrane fractions was measured using the Biorad protein assay kit according to manufacturers instructions. Radioligand binding assays were conducted according to Strnad et al. (15) using $^3$H-NECA (Amersham). Non-specific binding was defined as that observed in the presence of 1 uM NECA. Negligible specific binding was observed in membrane fractions made from cells lacking $A_{2a}$-adenosine receptor (data not shown).

Bioassay. Functional assay of the $A_{2a}$-adenosine receptor expressed in yeast was accomplished using a modification of a standard procedure (12). Yeast strains were grown overnight in 2 ml synthetic complete liquid medium containing glucose (2%) and Hacking uracil and tryptophan (SCD-ura-trp) medium, washed to remove residual glucose and grown overnight in 5 ml SC Glactose (2%)-ura-trp liquid medium. Molten (50° C.) SC Glactose (2%)-ura-trp-his agar medium (30 ml, adjusted to pH 6.8 by addition of concentrated KOH or NH,OH prior to autoclaving) containing 5 mM 3-aminotriazole (Sigma) was inoculated with the overnight culture (2×10$^4$ cells/ml) and plated in square (9×9 cm) petri plates. For expression of the $A_{2a}$-adenosine receptor in glucose-containing medium, samples were removed from the first overnight culture and assayed in agar medium composed as above with glucose (2%) replacing galactose. Sterile filter disks were placed on the surface of the solidified agar and saturated with 10 μl of DMSO containing the indicated amounts of the designated compounds. Plates were incubated at 30° C. for 3 days. Adenosine ligands CGS-21680, NECA, and DPMA were purchased from RBI. Somatostatin (S-14) and met-enkephalin were from Bachem. Oxymetazoline, isoproterenol, and carbachol were from Sigma.

RESULTS

Adenosine agonist binding to the rat $A_{2a}$-adenosine receptor expressed in yeast. High level functional expression of the $A_{2a}$-adenosine receptor in yeast was a necessary prerequisite to the development of a useful bioassay. In plasmid pJH21, the rat $A_{2a}$-adenosine receptor cDNA was placed under the control of the inducible GALI promoter. This construct also confers inducible overexpression of Gal4p, the transcriptional activating protein for galactose-inducible genes, resulting in significantly elevated levels of receptor protein in crude membrane fractions compared to receptor expressed from a plasmid lacking GAL4 sequences (data not shown). Plasmid pLP116 confers high level constitutive expression of the $A_{2a}$-adenosine receptor under the control of the ADHL promoter. In both plasmids, DNA sequences encoding the $A_{2a}$-adenosine receptor were introduced without modification of the protein coding sequences. Previously, King et al. reported that replacement of the amino terminal domian of the $\beta_2$- with equivalent SIE2 sequence was necessary for efficient receptor expression in yeast (16). In contrast, functional expression of the $A_{2a}$-adenosine receptor in yeast does not require addition of any yeast sequences to the amino-terminus. A chimeric Gα protein composed of the proposed amino-terminal βY-interaction domain from Gpalp and a carboxy-terminal receptor interaction domain from rat $G\alpha_s$ (pLP122) under the control of the GPA1 promoter was constructed. Yeast strains that contain expressed $A_{2a}$-adenosine receptor and chimeric Gα protein were assembled by transformation of a yeast strain (LY296) modified by deletion of genes encoding components of the mating signal transduction pathway with A2a- adenosine receptor and Gα protein expression plasmids.

Figure 20:
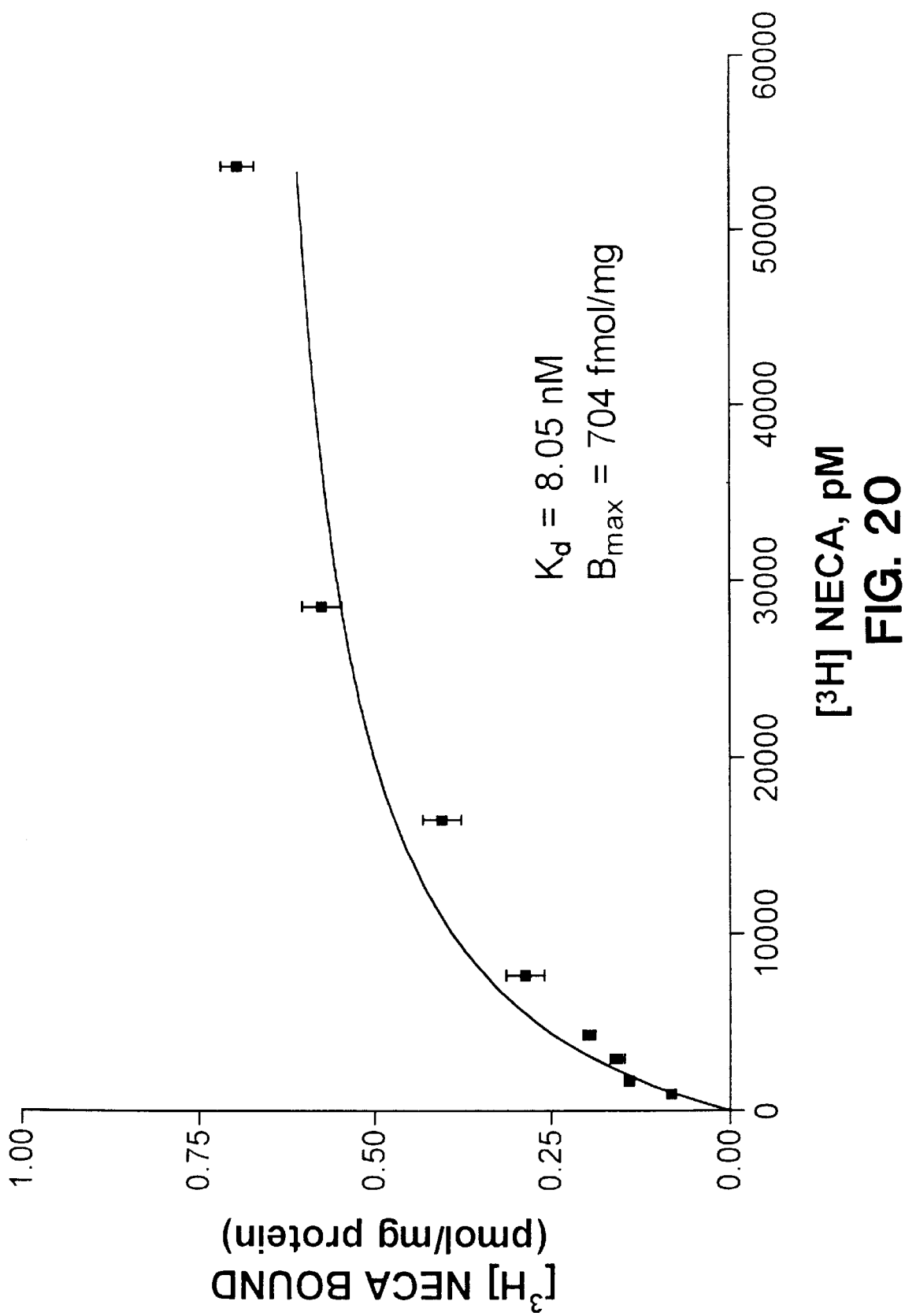
FIG. 20. $A_{2a}$-adenosine receptor saturation binding assay. Radioligand binding assays were performed in 96-well microliter plates using binding buffers (50nM HEPES, pH 7.4, 10 mM MgCl$_{21}$ 0.25% BSA) containing protease inhibitors (5µg/ml leupeptin, 5 µg/ml aprotinin, 100 µg/ml bacitracin, and 100 µg/ml benzamidine). All components were diluted in binding buffer containing protease inhibitors and added to the microliter plate wells in the following order: binding buffer, cold competitor (NECA, 1 µM final concentration), [$^3$NECA (1–50nM). Binding reactions were initiated by adding 82 µg of membrane protein in a 170 µl volume. Final reaction volume was 200 µl/well. All incubations were carried out at room temperature for 2 hours. Free radioligand was separated from bound ligand by rapid filtration through a glass fiber filter using an Inotech cell harvester. The filter disks were then washed several times with cold (4° C.) binding buffer lacking BSA prior to counting.

Most G protein-coupled receptors exhibit both high and low agonist-dependent affinity states. High-affinity agonist binding is dependent on functional association of receptor with a heterotrimeric G protein. If the receptor does not associate with, or is uncoupled from the G protein, agonist binding will be of low affinity and undetectable in radiolabeled agonist saturation binding assays. In crude yeast membrane fractions from cells bearing pLP116 and pLP122 (LY626), the agonist $^3$H-NECA bound to the $A_{2a}$-adenosine receptor with high affinity and in a saturable manner, (FIG. 20) demonstrating that (1) a functional ligand-binding conformation of the $A_{2a}$-adenosine receptor was expressed in yeast, and (2) the receptor functionally associated with the chimeric Gα protein, resulting in a high-affinity agonist binding state. The total number of $^3$H-NECA binding sites observed ($B_{max}$=242 fmol/mg) exceeded values obtained for the yeast α-mating pheromone receptor (200 fmol/mg, ref. 17). The affinity of [$^3$HI] NECA for the $A_{2a}$-adenosine receptor in yeast membranes (Kd-8 $\mu$M) is equivalent to that observed in mammalian cells indicating functional coupling between receptor and G protein.

Figure 21:
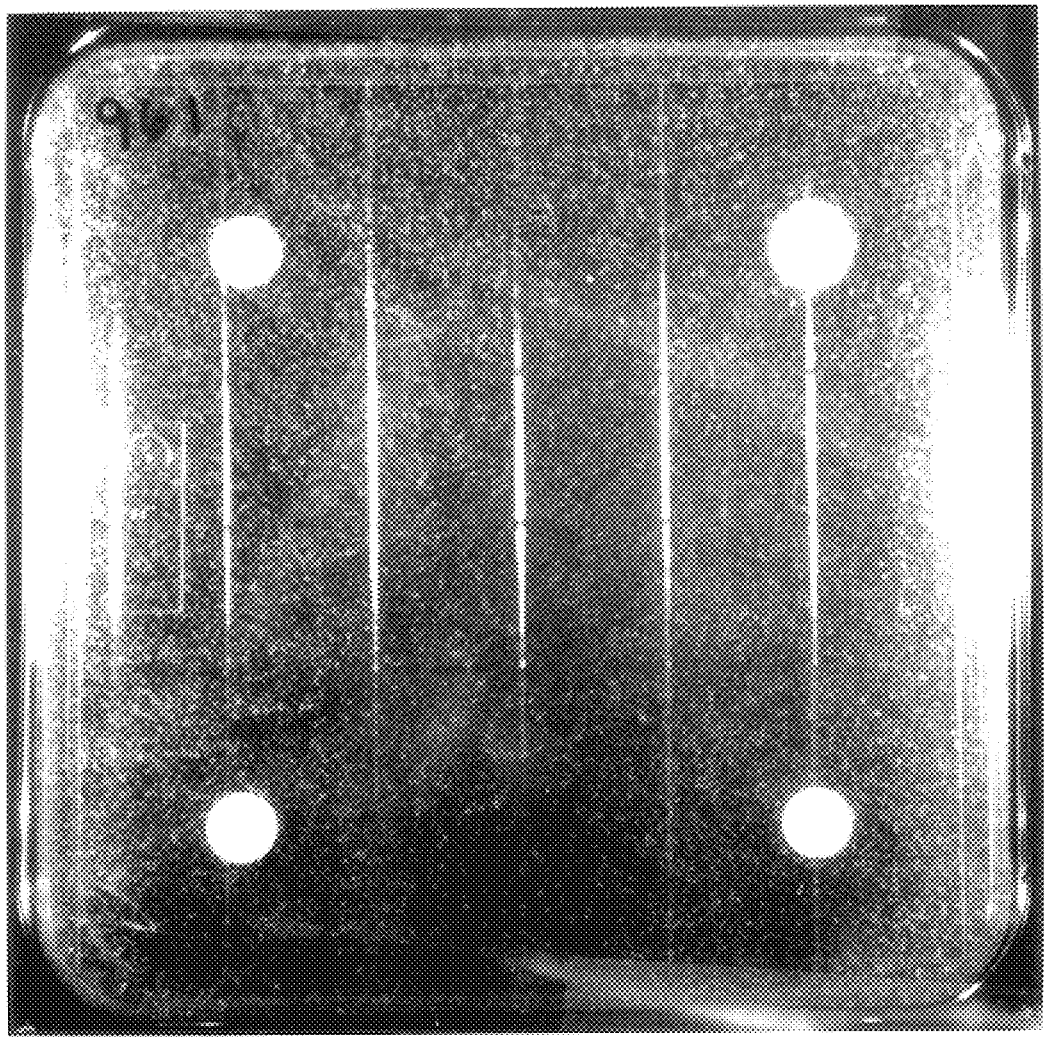
FIG. 21 Growth of yeast in response to $A_{2A}$-adenosine receptor agonists. LY595 cells cultured as described in Materials and Methods were plated in SC Galactose (2%)-ura, trp, his agar medium (2×10$^4$ cells/ml). Sterile filter disks were placed on the surface of the solidified agar and saturated with 10 µl of DMSO containing the 10 µg of the indicated compounds. The plates were then incubated at 30° C. for 3 days. (A, B) CGS-21680, (B) NECA (C) DPMA.

The $A_{2a}$-adenosine receptor retained agonist selectivity when expressed in yeast. A selective and sensitive bioassay was designed using a yeast strain (LY595) bearing the above described genetic modifications and plasmids conferring expression of the $A_{2a}$-adenosine receptor (pLP116) and GPAL (pLP83). A dose-dependent growth response of LY595 cells was evident around applied CGS-21680, an $A_{2a}$-adenosine receptor selective agonist. The growth response was significantly more robust than that exhibited by cells responding to NECA and DPMA (FIG. 21). The assay was selective: the diameter of the growth zones was proportional to the reported affinity of the ligands for the A, adenosine receptor (CGS-21680>NECA=DPMA) reflecting the ability of the bioassay to discriminate between ligands of varying potency. Detectable growth responses were not observed in response to a variety of agonists selective for other G protein-coupled receptors (somatostatin, met-enkephalin, oxymetazoline, isoproterenol, carbachol), nor by yeast cells lacking the $A_{2a}$-adenosine receptor (data not shown). A detectable response was observed to 10 $\mu$g of CGS-21680.

DISCUSSION

Multiple therapeutic opportunities exist for compounds that modulate the function of the adenosine receptors (1). Adenosine agonists may be useful in the treatment of epileptic seizure episodes and in preventing neuronal damage in stroke and neurodegenerative disorders. The antidysrhythmic action adenosine suggests that adenosine agonists could be effective in the treatment of complex tachycardia. $A_2$ adenosine agonists have potent sedative, anticonvulsant and anxiolytic activity. $A_{2a}$-adenosine selective agonists may be useful in stimulating lipolysis in adipose tissue, making them useful as weight loss treatments or antidiabetic agents and in the improvement of carcass quality in agricultural animals. $A_1$ adenosine antagonists may be useful in treatment of acute renal dysfunction. $A_3$-antagonists may be useful in modulating mast cell degranulation for treatment of inflamatory disorders, including asthema.

REFERENCES CITED IN THIS EXAMPLE

1. Jacobson, K. A., P. J. M. van Galen, and M. Williams. 1992. Adenosine receptors: Pharmacology, structure-activity relationships, and therapeutic potential. J. Med. Chem. 35: 407–422.

2. Libert, F., S. N. Schiffmann, A. Lefort, M. Pasmentier, C. Gerard, J. E. Dumont, J. J. Vanderhaeghen, and G. Vassart. 1991. The orphan receptor cDNA RDC7 encodes an Al adenosine receptor. EMBO J. 10: 1677–1682.

3. Mahan, L. C., L. D. McVittie, E. M. Smyk-Randal, H. Nakata, F. J. Monsma, C. R. Green, and D. R. Sibley. 1991. Cloning and expression of an $A_1$ adenosine receptor from rat brain. Mol. Pharmocol. 40: 1–7.

4. Olah, M. E., H. Ren, J. Ostrowski, K. A. Jacobson, and G. L. Stiles. 1992. Cloning, expression and characterization of the unique bovine A, adenosine receptor. J. Biol. Chem. 267: 10764–10770.

5. Tucker, A. L., J. Linden, A. S. Robeva, D. D. D'angelo, and K. R. Lynch. 1992. Cloning and expression of a bovine adenosine $A_1$ receptor cDNA. FEBS Lett. 297: 107–111.

6. Maenhaut, C., J. van Sande, F. Libert, M. Abramowicz, M. Parmetier, J. J. E. Dumont, G. Vassart, and S Schiffmann. 1990. RDC8 codes for an adenosine A2 receptor with physiological constitutive activity. Bioch. Biophys. Res. Comm. 173: 1169–1178.

7. Pierce, K. D., Furlong, T. J., L. A. Selbie, and J. Shine. 1992. Molecular cloning and expression of an adenosine A2b receptor from human brain. Bioch. Biophys. Res. Comm. 187: 86–93.

8. Chern, Y., K. King, H. L. Lai, and H. T. Lai. 1992. Molecular cloning of a novel adenosine receptor gene from rat brain. Bioch. Biophys. Res. Comm. 185: 304–309.

9. Stehle, J. H., S. A. Rivkees, J. J. Lee, D. R. Weaver, J. D. Deeds, and S. M. Reppert. 1992. Molecular cloning and expression of the cDNA for a novel $A_2$ adenosine receptor subtype. Mol. Endocrinol. 6: 384–393.

10. Zhou, Q. Y., C. Li, M. E. Olah, R. A. Johnson, G. L. Stiles, and O. Civelli. 1992. Molecular cloning and characterization of an adenosine receptor: The A3 adenosine receptor. Proc. Natl. Acad. SCI. USA. 89: 7432–7436.

11. Sambrook, J., E. F. Fritsch, and T. Maniatis. 1989. Molecular Cloning, A Laboratory Handbook. Cold Spring Harbor Press. Cold Spring Harbor, N.Y.

12. Price, L. A., E. M. Kajkowski, J. R. Hadcock, B. A. Ozenberger, and M. H. Pausch. 1995. Yeast cell growth in response to agonist dependent activation of a mammalian somatostatin receptor. submitted.

13. Rose, M., F. Winston, and P. Hieter. 1990. Methods in Yeast Genetics. Cold Spring Harbor Press. Cold Spring Harbor, N.Y.

14. Blumer, K. J., J. E. Reneke, and J. Thorner. 1988. The STE2 gene product is the ligand-binding component of the α-factor receptor of Saccharomyces cerevisiae. J. Biol. Chem. 263: 10836–10842.

15. Strnad, J., C. M. Eppler, M. Corbett, and J. R. Hadcock. 1993. The rat SSTR2 somatostatin receptor subtype is coupled to inhibition of cyclic AMP accumulation. Biochem. Biophys. Res. Comm. 191: 968–976.

16. King, K., H. G. Dohlman, J. Thorner, M. G. Caron, and R. J. Lefkowitz. 1990. Control of yeast mating signal transduction by a mammalian $\beta_2$-adrenergic receptor and $G_S$ α subunit. Science 250: 121–123.

17. Weiner, J. L., C. Guttierez-Steil, and K. J. Blumer. 1993. Disruption of receptor-G protein coupling in yeast promotes the function of an SST2-dependent adaptation pathway. J. Biol. Chem. 268: 8070–8077.

EXAMPLE 9

Functional expression of a rat somatostatin subtype 5 receptor in yeast.

The cyclic tetradecapeptide somatostatin is a potent inhibitor of secretion of several hormones, including growth hormone from the pituitary, glucagon and insulin from the pancreas, and gastrin from the gut. Somatostatin also acts as a neurotransmitter and has been shown to have broad modulatory effects in CNS and peripheral tissues (1). The effects of somatostatin are transduced through binding of the hormone to high-affinity, plasma membrane localized somatostatin (SSTR) receptors (2). The SSTR's, encoded in five distinct subtypes (SSTR1-5), which account in part for tissue-specific differences in responses to somatostatin (3–10), comprise a subfamily of the seven-transmembrane domain, G protein-coupled receptor superfamily that mediates responses to a broad variety of extracellular signals. Functional expression of SSTR5 in yeast should permit rapid screening for new subtype-selective somatostatin agonists and compounds with antagonist properties and facilitate molecular characterization of structural aspects of the SSTR5 requited for rational design of new somatostatin ligands.

MATERIALS AND METHODS

Plasmid constructions. All molecular biological manipulations were performed according to standard procedures (11). The rat SSTR5 (7) was cloned from rat genomic DNA by PCR using oligonucleotide primers that introduce BglII sites at,, 5' and 3' ends (5'AAAAAGATCTAAAATGGAGCCCCTCTCTCTG, (SEQ. ID NO:11) 3'AGCAGATCTTCAGATC CCAGAAGACAAC(SEQ. ID NO:12)). The STR5 expression plasmid, pJHl9, was constructed by inserting the BglII-digested PCR fragment in the correct orientation into BamHII cut pMP3 (12). The Gα protein expression plasmids used in this study were constructed by replacing DNA sequences encoding the 47 carboxy-terminal amino acids of GPA1 in pLP83 (12) with those of $G\alpha_S$ (pLP122), $G\alpha_{12}$ (pLP121).

Strain constructions. Yeast strains were constructed, and growth media and culture conditions formulated according to standard procedures (13). DNA-mediated transformation of yeast was carried out using the lithium acetate method. The yeast strains used as the basis for all experiments described in this report were constructed by sequential insertional deletion using recombinant alleles. Yeast strains that express SSTR5 were constructed by sequential DNA-mediated transformation of LY296 (MATA ura3–52 trp1Δ63 his3Δ200 leu2Δ1 ade2–101 lys2–801 gpa1ΔhisG far1ΔLYS2 FUS1-HIS3 sst2ΔADE2, ref. 12) with pJH19 followed by the Gα protein expression plasmids described above.

Bioassay. Functional assay of SSTR5 expressed in yeast was accomplished using modification of a standard procedure (12). Yeast strains were grown overnight in 2 ml synthetic complete liquid medium containing glucose (2%) and lacking uracil and tryptophan (SCD-ura-trp) medium, washed to remove residual glucose, and grown overnight in 5 ml SC Glactose (2%)-ura-trp liquid medium. Molten (55° C.) SC Glactose (2%)-ura-trp-his agar medium (30 μl, adjusted to pH 6.8 by addition of concentrated KOH or $NH_4OH$ prior to autoclaving) was inoculated with the overnight culture ($2 \times 10^4$ cells/ml) and plated in square (9×9 cm) petri plates. Sterile filter disks were placed on the surface of the solidified agar and saturated with 10 μl of sterile water containing the indicated amounts of the designated compounds. Plates were incubated at 30° C. for 3 days. Somatostatin (S-14, S-28), met-enkephalin, and CCK-8 were from Bachem. Oxymetazoline, isoproterenol, and carbachol were from Sigma.

RESULTS

Figure 22:
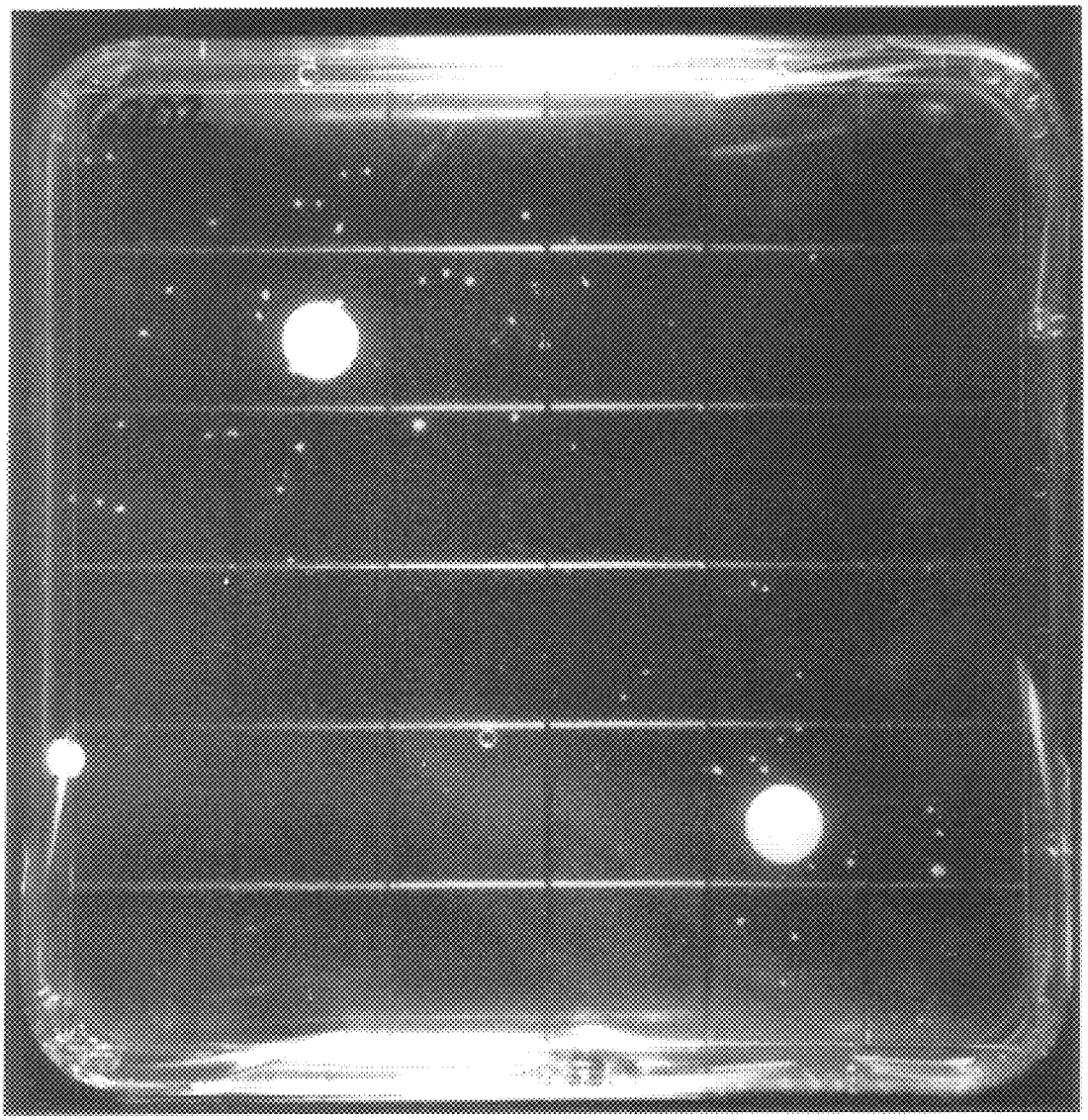
FIG. 22 Growth of yeast cells containing SSTR5 in response to somatostatin receptor agonists. LY620 cells cultured as described in Materials and Methods were plated in SC Galactose (2%)-ura, trp, his agar medium (2×10$^4$ cells/ml). Sterile filter disks were placed on the surface of the solidified agar and saturated with 10 µl of sterile water containing the indicated amounts of the indicated compounds. The plates were then incubated at 30° C. for 3 days. (A) 60 nmol S-14, (B) 30 =mol S-28.

Somatostatin dependent growth response of yeast cells expressing the SSTRS. High level functional expression of the SSTR5 in yeast was a necessary prerequisite to the development of a useful bioassay. The SSTR5 cDNA was placed under the control of the GAL1 promoter in plasmid pJH19. This construct also confers inducible overexpression of Gal4p, the transcriptional activating protein for galactose-inducible genes, resulting in significantly elevated levels of receptor protein in crude membrane fractions compared to receptor expressed from a plasmid lacking GAL4 sequences (data not shown). SSTR5 sequences were introduced into pJH19 without modification of the protein coding sequences. Previously, King et al. reported that replacement of the amino-terminal domain of the $\beta_2$-adrenergic receptor with equivalent STE2 sequence was necessary for efficient receptor expression in yeast (15). In contrast, functional expression of SSTR5 in yeast does not require addition of any yeast sequences to the amino-terminus. A chimeric Gα protein composed of the proposed amino-terminal $\beta_2$-interaction domain from Gpalp and a carboxy-terminal receptor interaction domain from rat $G\alpha_{12}$ (pLP121) under the control of the GPAL promoter was constructed. A yeast strain (LY620) that contains expressed SSTR5 and chimeric Gα protein was assembled by transformation of a yeast strain (LY296) modified by deletion of genes encoding components of the mating signal transduction pathway with SSTR5 (pJH19) and Gα protein expression (pLPl21) plasmids. A dose-dependent growth response of LY620 cells was evident around applied S-14 (FIG. 22). Detectable growth responses were not observed in response to a variety of agonists selective for other G protein-coupled receptors (CCK-8, met-enkephalin, oxymetazoline, isoproteranol, carbachol), nor by yeast cells lacking the SSTR5 (data not shown). A detectable response was observed to 60 nmol of S-14.

REFERENCES CITED IN THIS EXAMPLE

1. Brazeau, P., W. Vale, R. Burgus, N. Ling, M. Butcher, J. Rivier and R. Guillemin. 1973. Hypothalamic polypeptide that inhibits the secretion of immunoreactive pituitary growth hormone. Science 129: 77–79.

2. Reisine, T. and G. I. Bell 1993. Molecular biology of somatostatin receptors. Trends Neurosci. 16: 34–38.

3. Meyerhof, W., H. J. Paust, C. Schonrock, and D. Richter. 1991. Cloning of a cDNA encoding a novel putative G protein-coupled receptor expressed in specific rat brain regions. DNA Cell Biol. 10: 669–694.

4. Bruno, J. F., Y. Xu, J. Song, and M. Berelowitz. 1992. Molecular cloning and functional expression of a brain specific somatostatin receptor. Proc. Natl. Acad. Sci. USA 89: 11151–11155.

5. Kluxen, F. W., C. Bruns, and E. Lubbert. 1992. Expression cloning of a rat brain somatostatin receptor. Proc. Natl. Acad. Sci. USA 89: 4618–4622.

6. Li, X. J., M. Forte, R. A. North, C. A. Ross, and S. H. Snyder. 1992. Cloning and expression of a rat somatostatin receptor enriched in brain. J. Biol. Chem. 267: 21307–21312.

7. O'Carrol, A. M., S. J. Lolait, M. Konig, and L. Mahan. 1992. Molecular cloning and expression of a pituitary somatostatin receptor with preferential affinity for somatostatin-28. Mol. Pharmocol. 42: 939–946.

8. Yasuda, K., S. Rens-Damiano, C. D. Breder, S. F. Law, C. B. Saper, T. Raisine and G. I. Bell. 1992. Cloning of a novel somatostatin receptor, SSTR3, coupled to adenylyl-cyclase. J. Biol. Chem. 28: 20422–20428.

9. Yamada, Y., S. R. Post, K. Wang, E. S. Tager, G. I. Bell and S. Seino. 1992. Cloning and functional characterization of a family of human and mouse somatostatin receptors expressed in brain, gastrointestinal tract, and kidney. Proc. Natl. Acad. Sci. USA 89: 251–255.

10. Strnad, J., C. M. Eppler, M. Corbett, and J. R. Hadcock. 1993. The rat SSTR2 somatostatin receptor subtype is coupled to inhibition of cyclic AMP accumulation. Biochem. Biophys. Res. Comm. 191: 968–976.

11. Sambrook, J., E. F. Fritsch, and T. Maniatis. 1989. Molecular Cloning, A Laboratory Handbook. Cold Spring Harbor Press. Cold Spring Harbor, N.Y.

12. Price, L. A., E. M. Kajkowski, J. R. Hadcock, B. A. Ozenberger, and M. E. Pausch. 1995. Yeast cell growth in response to agonist dependent activation of a mammalian somatostatin receptor. submitted.

13. Rose, M., F. Winston, and P. Rieter. 1990. Methods in Yeast Genetics. Cold Spring Harbor Press. Cold Spring Harbor, N.Y.

14. Blumer, K. J., J. E. Reneke, and J. Thorner. 1988. The STE2 gene product is the ligand-binding component of the α-factor receptor of Saccharomyces cerevisiae. J. Biol. Chem. 263: 10836–10842.

15. King, K., H. G. Dohlman, J. Thorner, M. G. Caron, and R. J. Lefkowitz. 1990. Control of yeast mating signal transduction by a mammalian $\beta_2$-adrenergic receptor and Gα α a subunit. Science 250: 121–123.

16. Weiner, J. L., C. Guttierez-Steil, and K. J. Blir. 1993. Disruption of receptor-G protein coupling in yeast promotes the function of an SST2-dependent adaptation pathway. J. Biol. Chem. 268: 8070–8077.

EXAMPLE 10

Functional expression of the porcine somatostatin subtype 2 (SSTR2) receptor in yeast The cyclic tetradecapeptide somatostatin is a potent inhibitor of secretion of several hormones, including growth hormone from the pituitary, glucagon and insulin from the pancreas, and gastrin from the gut. Somatostatin also acts as a neurotransmitter and has been shown to have broad modulatory effects in CNS and peripheral tissues (1). The effects of somatostatin are transduced through binding of the hormone to high-affinity, plasma membrane localized somatostatin (SSTR) receptors (2). The SSTR's, encoded in five distinct subtypes (SSTR-5), which account in part for tissue-specific differences in responses to somatostatin (3–11), comprise a subfamily of the seven-transmembrane domain, G protein-coupled receptor superfamily that mediates responses to a broad variety of extracellular signals. Functional expression of porcine SSTR2 in yeast should permit rapid screening for new species and subtype-selective somatostatin agonists and compounds with antagonist properties and facilitate molecular characterization of structural aspects of the porcine SSTR2 required for rational design of new somatostatin ligands. Compounds identified in high-throughput, mechanism-based screens represent leads for new growth-enhancing agents for use in pigs.

MATERIALS AND METHODS

Plasmid constructions. All molecular biological manipulations were performed according to standard procedures, (12). The porcine SSTR2 (11) was cloned from a human brain cDMA library by PCR using oligonucleotide primers that introduce BglII sites at 5' and 3' ends (5=AAAAGATCTAAAATGTCCATTCCATTTGAC(SEQ. ID NO: 13), 3' AAAAGGTACCAGATCTTCAGATACTGGTTTGGAG (SEQ. ID NO. 14)). The porcine SSTR2 expression plasmid, pJH18, was constructed by inserting the BglII-digested PCR fragment in the correct orientation into BamHI cut pMP3 (13).

Strain constructions. Yeast strains were constructed, and growth media and culture conditions formulated according to standard procedures (14). DNA-mediated transformation of yeast was carried out using the lithium acetate method. The yeast strains used as the basis for all experiments described in this report were constructed by sequential insertional deletion using recombinant alleles. Yeast strains that express porcine SSTR2 were constructed by sequential DNA-mediated transformation of LY296 (MATa ura3–52 trp1Δ63 his3Δ200 leu2Δ1 ade2–101 lys2–801 gpa1ΔhisG far1ΔLYS2 FUS1-HIS3 sst2ΔADE2 , ref. 13) with the chimeric $G_{\alpha 2}$ protein expression plasmid, pLP82 (13), followed by pJH18 or pJH17.

Radiolabeled agonist saturation binding assays. Crude yeast membrane extracts from late log phase cultures were prepared by glass-bead lysis and centrifugation at 40,000 xg following a published procedure (15). The protein content of crude membrane fractions was measured using the Biorad protein assay kit according to manufacturers instructions. Radioligand binding assays were conducted according to Strnad et al (10) using radiolabeled somatostatin ($^{125}$I-tyr$^{11}$-S-14, Amersham). Non-specific binding was defined as that observed in the presence of 1 μM S-14. Negligble specific binding was observed in membrane fractions made from cells lacking porcine SSTR2 (data not shown).

Bioassay. Functional assay of the porcine SSTR2 expressed in yeast was accomplished using modification of a standard procedure (13). Yeast strains were grown overnight in 2 ml synthetic complete liquid medium containing glucose (2%) and lacking uracil and tryptophan (SCD-uratrp) medium, washed to remove residual glucose, and grown overnight in 5 ml SC Glactose (2%)-ura-trp liquid medium. Molten (55° C.) SC Glactose (2%)-ura-trp-his agar medium (30 ml, adjusted to pH 6.8 by addition of concentrated KOH or NH,OH prior to autoclaving) was inoculated with the overnight culture (2×10⁴ cells/ml) and plated in square (9×9 cm) petri plates. Sterile filter disks were placed on the surface of the solidified agar and saturated with 10 μl of sterile water containing the indicated amounts of the designated compounds. Plates were incubated at 30° C. for 3 days. Somatostatin (S-14, S-28), met-enkephalin were from Bachem. Oxymetazoline, isoproterenol, and carbachol were from Sigma. MK678 and sandostatin were prepared synthetically.

RESULTS

Somatostatin binding to the porcine SSTR2 expressed in yeast. High level functional expression of the porcine SSTR2 in yeast was a necessary prerequisite to the development of a useful bioassay. The porcine SSTR2 cDNA was placed under the control of the GAL1 promoter in plasmid pJH17 and 18. These constructs also confer inducible overexpression of Gal4p, the transcriptional activating protein for galactose-inducible genes, resulting in significantly elevated levels of receptor protein in crude membrane fractions compared to receptor expressed from a plasmid lacking GAL4 sequences (data not shown). The porcine SSTR2 sequences were introduced into pJH18 without modification of the protein coding sequences. Previously, King et al. reported that replacement of the amino-terminal domain of the $β_2$-adrenergic receptor with equivalent STE2 sequence was necessary for efficient receptor expression in yeast (16). In contrast, functional expression of porcine SSTR2 in yeast does not require addition of any yeast sequences to the amino-terminus. A chimeric Gα protein composed of the proposed amino-terminal βY-interaction domain from Gpa1p and a carboxy-terminal receptor interaction domain from rat $Gα_{12}$ (pLP82) under the control of the GPA1 promoter was constructed. Yeast strains that contain expressed porcine SSTR2 and chimeric $G_g$ protein were assembled by transformation of a yeast strain (LY296) modified by deletion of genes encoding components of the mating signal transduction pathway with porcine SSTR2 (pJH17, pJH18) and $G_α$ protein expression (pLP2) plasmids.

Most G protein-coupled receptors exhibit both high and low agonist-dependent affinity states. High-affinity agonist binding is dependent on functional association of receptor with a heterotrimeric G protein. If the receptor does not associate with, or is uncoupled from the G protein, agonist binding will be of low affinity and undetectable in radiolabeled agonist saturation binding assays. In crude yeast membrane fractions from cells bearing pJH17, the agonist $^{125}$I-tyr$^{11}$-S-14 bound to the porcine SSTR2 with high affinity and in a saturable manner, demonstrating that (1) a functional ligand-binding conformation of the porcine SSTR2 was expressed in yeast, and (2) the receptor functionally associated with the chimeric Gα protein, resulting in a high-affinity agonist binding state. The total number of $^{125}$I-tyr$^{11}$-S-14 binding sites observed ($B_{max}$=146 fmol/mg) was consistent with values obtained for the yeast α-mating pheromone receptor (200 fmol/mg, ref. 17).

Figure 23:
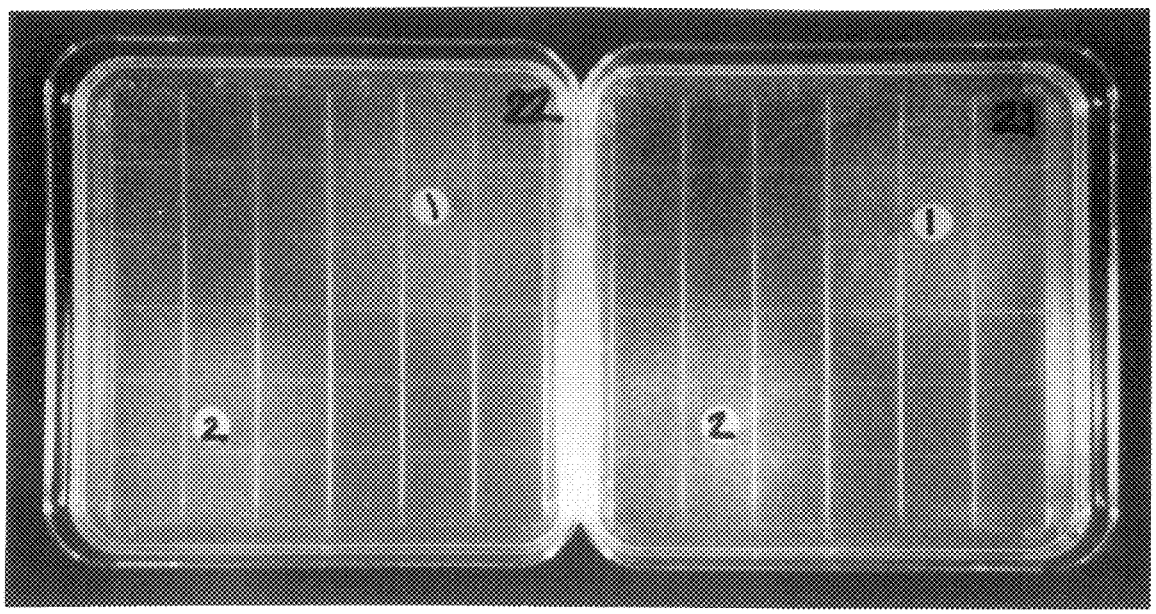
FIG. 23 Growth of yeast cells containing porcine SSTR2 in response to somatostatin receptor agonists. LY474 (two independent isolates: 21,22) were cultured as described in Materials and Methods were plated in SC Galactose (2%)-ura, trp, his agar medium (2×10$^4$ cells/ml). Sterile filter disks were placed on the surface of the solidified agar and saturated with 10 µl of sterile water containing the indicated amounts of the indicated compounds. The plates were then incubated at 30° C. for 3 days. (1) 600 pmol, (2) 60 pmol.

The porcine SSTR2 retained agonist selectivity when expressed in yeast. A selective and sensitive bioassay was designed using a yeast strain (LY474) bearing the above described genetic modifications and plasmids conferring expression of the porcine SSTR2 (pJH18) and a Gpal-$Gα_{12}$ chimeric protein (pLP82) . A dose-dependent growth response of LY474 cells was evident around applied S-14, MK678, and sandostatin (FIG. 23). The assay was selective: the diameter of the growth zones was proportional to the reported affinity of the ligands for the porcine SSTR2 (S-14=MK678>sandostatin) reflecting the ability of the bioassay to discriminate between ligands of varying potency (18). Detectable growth responses were not observed in response to a variety of agonists selective for other G protein-coupled receptors (met-enkephalin, oxymetazoline, isoproterenol, carbachol), nor by yeast cells lacking the porcine SSTR2 (data not shown). A detectable response was observed to as little as 60 pmol of S-14, illustrating the exquisite sensitivity of the bioassay.

REFERENCES CITED IN THIS EXAMPLE

1. Brazeau, P., W. Vale, R. Burgus, N. Ling, M. Butcher, J. Rivier and R. Guillemin . 1973. Hypothalamic polypeptide that inhibits the secretion of immunoreactive pituitary growth hormone. Science 129: 77–79.

2. Reisine, T. and G. I. Bell 1993. Molecular biology of somatostatin receptors. Trends Neurosci. 16: 34–38.

3. Meyerhof, W., H. J. Paust, C. Schonrock, and D. Richter. 1991. Cloning of a cDNA encoding a novel putative G protein-coupled receptor expressed in specific rat brain regions. DNA Cell Biol. 10: 689–694.

4. Bruno, J. F., Y. Xu, T. Song, and M. Berelowitz. 1992. Molecular cloning and functional expression of a brain specific somatostatin receptor. Proc. Natl. Acad. Sci. USA 89: 11151–11155.

5. Kluxen, F. W., C. Bruns, and E. Lubbert. 1992. Expression cloning of a rat brain somatostatin receptor. Proc. Natl. Acad. Sci. USA 89: 4618–4622.

6. Li, X. J., M. Forte, R. A. North, C. A. Ross, and S. H. Snyder. 1992. Cloning and expression of a rat somatostatin receptor enriched in brain. J. Biol. Chem. 267: 21307–21312.

7. O'Carrol, A. M., S. J. Lolait, M. Konig, and L. Mahan. 1992. Molecular cloning and expression of a pituitary somatostatin receptor with preferential affinity for somatostatin-28. Mol. Pharmacol. 42: 939–946.

8. Yasuda, X., S. Rens-Domiano, C. D. Breder, S. F. Law, C. B. Saper, T. Raisine and G. I. Bell. 1992. Cloning of a novel somatostatin receptor, SSTR3, coupled to adenylylcyclase. J. Biol. Chem. 28: 20422–20428.

9. Yamada, Y., S. R. Post, K. Wang, E. S. Tager, G. I. Bell and S. Seino. 1992. Cloning and functional characterization of a family of human and mouse somatostatin receptors expressed in brain, gastrointestinal tract, and kidney. Proc. Natl. Acad. Sci. USA 89: 251–255.

10. Strnad, J., C. M. Eppler, M. Corbett, and J. R. Hadcock. 1993. The rat SSTR2 somatostatin receptor subtype is coupled to inhibition of cyclic AMP accumulation. Biochem. Biophys. Res. Comm. 191: 968–976.

11. Matsumoto, K., Y. Yokogoshi, Y. Fujinaka, C. Z. Xhang, and S. Saito. 1994. Molecular cloning and sequencing of porcine somatostatin receptor 2. Biochem. Biophys. Res. Comm. 199: 298–305.

12. Sambrook, J., E. F. Fritsch, and T. Maniatis. 1989. Molecular Cloning, A Laboratory Handbook. Cold Spring Harbor Press. Cold Spring Harbor, N.Y.

13. Price, L. A., E. M. Kajkowski, J. R. Hadcock, B. A. Ozenberger, and M. E. Pausch. 1995. Yeast cell growth in response to agonist dependent activation of a mammalian somatostatin receptor. submitted.

14. Rose, M., F. Winston, and P. Rieter. 1990. Methods in Yeast Genetics. Cold Spring Harbor Press. Cold Spring Harbor, N.Y.

15. Blumer, K. J., J. E. Reneke, and J. Thorner. 1988. The STE2 gene product is the ligand-binding component of the α-factor receptor of Saccharomyces cerevisiae. J. Biol. Chem. 263: 10836–10842.

16. King, K., H. G. Dohlman, J. Thorner, M. G. Caron, and R. J. Lefkowitz. 1990. Control of yeast mating signal transduction by a mammalian 2-adrenergic receptor and $G_s$ α subunit. Science 250: 121–123.

17. Weiner, J. L., C. Guttierez-Steil, and K. J. Blumer. 1993. Disruption of receptor-G protein coupling in yeast promotes the function of an SST2-dependent adaptation pathway. J. Biol. Chem. 268: 8070–8077.

18. Marbach, P., W. Bauer, and U. Briner. 1988. Structure-function relationships of somatostatin analogs. Horm Res. 29: 54–58.

EXAMPLE 11

Deletion of MSG5 increases the sensitivity of response to agonist.

The responsiveness of a signal transduction system to a persistent stimulus diminishes with time. This phenomenon, known as desensitization or adaptation, is a universal characteristic of signal response systems. Several molecular mechanisms for adaptation have been described for the yeast mating signal transduction pathway (1). Mutations in the SST2 gene confer defects in adaptation and increased mating pheromone sensitivity (2,3): The response to applied somatostatin by yeast cells that functionally express the rat SSTR2 is greatly increased in sst2 mutant cells (4). Mutations in others genes whose products play a role in the adaptation response would be expected to have similar effects. Mutations in the MSG5 gene, which encodes a putative protein tyrosine phosphatase, cause increased sensitivity to mating pheromone (5). In this study, deletion of MSG5 in cells that express the rat SSTR2 greatly increases sensitivity to somatostatin. The effect of the MSG5 mutation is additive with an SST2 deletion mutation. The double mutant sst2 msg5 cells form the basis of an extremely sensitive bioassay for compounds that interact with G protein-coupled receptors and G proteins.

MATERIALS AND METHODS

Strain constructions. All molecular biological manipulations were performed according to standard procedures (6). Yeast strains were constructed, and growth media and culture conditions formulated according to standard procedures (7). DNA-mediated transformation of yeast was carried out using the lithium acetate method. The yeast strains used in these experiments were constructed using the recombinant msg5ΔLEU2 allele in pS/PDel and multicopy YEpMSG5 (5). Yeast strains bearing altered MSG5 levels were constructed by DNA-mediated transformation of LY268 (MATa ura3–52 trp1D63 his3D200 leu2D1 ade2–101 lys2–801 gpa1ΔhisG far1ΔLYS2 FUS1-HIS3 sst2ΔADE2, pJH2, pLP82) yielding MPY459 (LY268 msg5ΔLEU2 sst2ΔADE2) and MPY467 (LY268 YEpMSG5) and LY288 (LY268 SST2) yielding MPY458 (LY288 msg5ΔLEU2 SST2) and MPY466 (LY288 YEpMSG5) (4).

Bioassay. Functional bioassay of the rat SSTR2 expressed in yeast was accomplished using modification of a standard procedure (4). Yeast strains were grown overnight in 2 ml synthetic complete liquid medium containing glucose (2%) and lacking uracil, tryptophan and leucine (SCD-ura-trp-leu) medium, washed to remove residual glucose, and grown overnight in 5 ml SC Glactose (2%)-ura-trp-leu liquid medium. Molten (55° C.) SC Glactose (2%)-ura-trp-leu-his agar medium (35 ml, adjusted to pH 6.8 by addition of concentrated $NH_4OH$ prior to autoclaving) was inoculated with the overnight culture ($2\times10^4$ cells/ml) and plated in square (9×9 cm) petri plates. Sterile filter disks were placed on the surface of the solidified agar and saturated with 10 μl of sterile water containing the indicated amounts of the somatostatin (S-14). Plates were incubated at 30° C. for 3 days. Somatostatin (S-14) was from Bachem.

RESULTS

Figure 24:
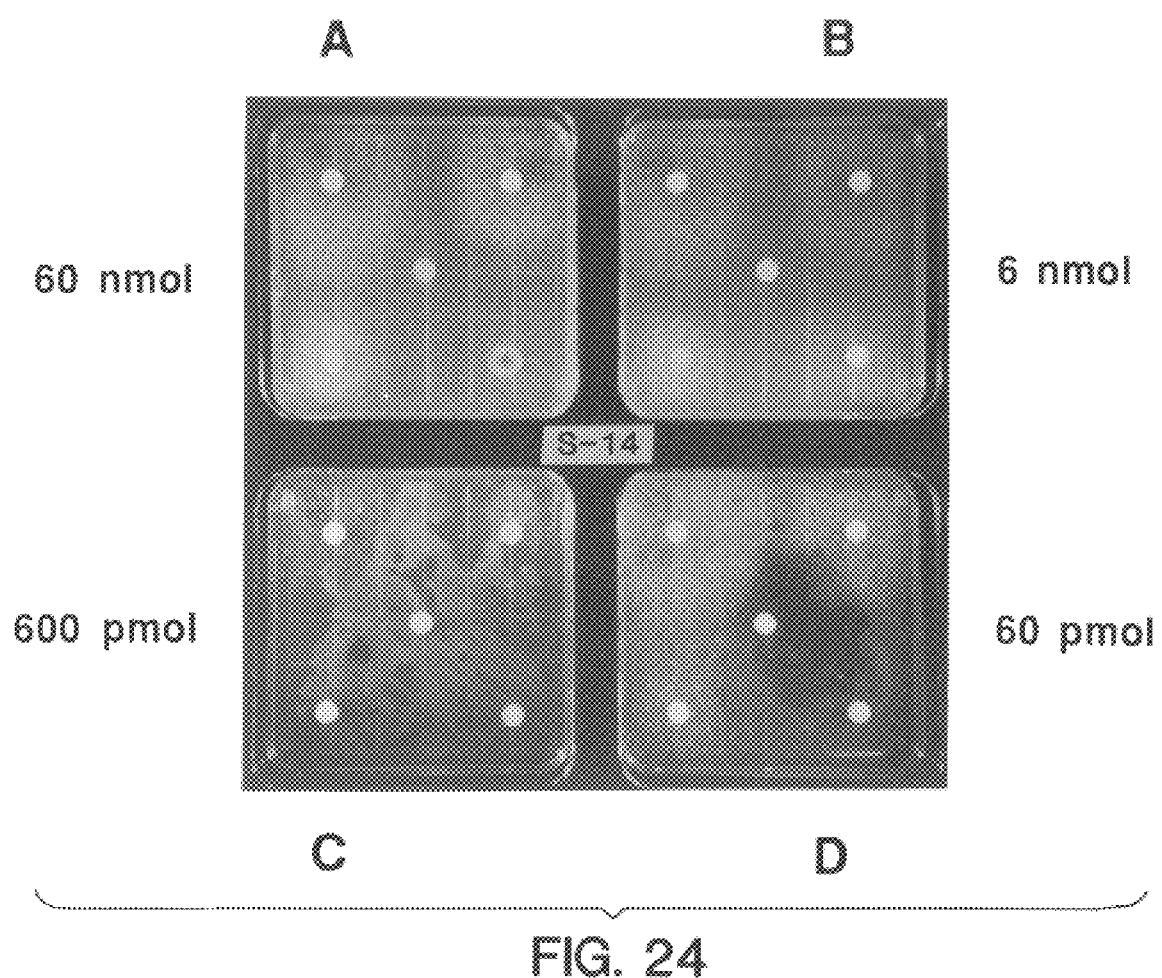
FIG. 24 Deletion of MSG5 increases the sensitivity of the yeast bioassay. Cultures of yeast strains were induced to express the SSTR2 as described in Materials and Methods and were plated in SC Galactose (2%)-ura, trp, his agar medium (2×10$^4$ cells/ml). Sterile filter disks were placed on the surface of the solidified agar and saturated with 10 µl of sterile water containing the indicated amounts of S-14. The plates were then incubated at 30° C. for 3 days. (A) MPY459 sst2ΔADE2 msg5ΔLEU2, (B) MPY458 SST2 msg5ΔLEU2, (C) LY288 SST2 MSG5, (D) LY268 sst2ΔADE2 MSG5.

Deletion of MSG5 promotes increased sensitivity to ligand. The effects of alterations in the expression of the MSG5 gene product were assessed by comparing the growth response to S-14 by cells that express the rat SSTR2 (FIG. 24). Mutations that abolish MSG5 adaptation function would be expected to increase the sensitivity of the bioassay to applied S-14, while overexpression of MSG5 should blunt the growth response. As expected, a dose-dependent growth response to applied S-14 was observed for LY288 (SST2 MSG5). Consistent with expectations, deletion of the MSG5 gene in MPY458 causes a substantial improvement in sensitivity of the bioassay. The growth response of MPY458 is comparable to that exhibited by LY268 (sst2ΔADE2, MSG5). The effects of mutations in both genes was observed in the double mutant MPY459 (msg5ΔLEU2 sst2ΔADE2) which showed a further improvement in the growth response. Overexpression of MSG5 in SST2 (MPY466) and sst2ΔADE2 (MPY467) strains severely reduced the growth response.

REFERENCES CITED IN THIS EXAMPLE

1. Sprague, G. F. and J. W. Thorner. 1992. Pheromone response and signal transduction during the mating process of *Saccharomyces cerevisiae*, 657–744.. In J. R. Pringle, E. W. Jones and J. R. Broach, Gene expression, 2. Cold Spring Harbor Laboratory Press, Cold Spring Harbor, N.Y.

2. Chan, R. K. and C. A. Otte. 1982. Isolation and genetic analysis of Saccharomyces cerevisiae mutants supersensitive to G1 arrest by a factor and a factor pheromones. Mol. Cell. Biol. 2: 11–20.

3. Chan, R. K. and C. A. Otte. 1982. Physiological characterization of Saccharomyces cerevisiae mutants supersensitive to G1 arrest by α factor and a factor pheromones. Mol. Cell. Biol. 2: 21–29.

4. Price, L. A., E. M. Kajkowski, J. R. Hadcock, B. A. Ozenberger, and M. H. Pausch. 1995. Yeast cell growth in response to agonist dependent activation of a mammalian somatostatin receptor. submitted.

5. Doi, K., A. Gartner, G. Ammerer, B. Errede, H. Shinkawa, K. Sugimoto, and K. Matsumoto. 1994. MSG5, a novel protein phosphatase promotes adaptation to pheromone response in *S. cerevisiae*. EMBO J. 13: 61–70.

6. Sambrook, J., E. F. Fritsch, and T. Maniatis. 1989. Molecular Cloning, A Laboratory Handbook. Cold Spring Harbor Press. Cold Spring Harbor, N.Y.

7. Rose, M., F. Winston, and P. Hieter. 1990. Methods in Yeast Genetics. Cold Spring Harbor Press. Cold Spring Harbor, N.Y.

EXAMPLE 12

Functional expression of a human growth hormone release factor (GRF) receptor in yeast The growth hormone release factor (GRF) is a potent stimulator of secretion of growth hormone from the pituitary (1). The effects of GRF are transduced through binding of the hormone to high-affinity, plasma membrane localized GRF receptors. The GRF receptor and related secretin-class receptors comprise a subfamily of the seven-transmembrane domain, G protein-coupled receptor superfamily that mediates responses to a broad variety of extracellular signals, and are distinguished by the presence of a large amino-terminal ligand-binding domain (2). Functional expression of the human GRF receptor (3) in yeast should permit rapid screening for new species-selective agonists and facilitate molecular characterization of structural aspects of the GRF receptor required for rational design of new GPF receptor ligands. GRF agonists represent a new class of growth promoting agents for use in agricultural animals and may find human therapeutic application in the management of growth of children of short stature.

MATERIALS AND METHODS

Plasmid constructions. All molecular biological manipulations were performed according to standard procedures (4). The human GRF receptor (3) was cloned from a human brain cDNA library by PCR using oligonucleotide primers that introduce BamHI sites at 5' and 3' ends (5' ATAGGATCCAAAATGGACCGCCGGATGTGGGGG (SEQ. ID NO:15), 3'ATATGGATCCCTAGCACATAGATGTCAG(SEQ. ID NO:16)). The GRF receptor expression plasmid, pJH25, was constructed by inserting the BamHI-digested PCR fragment in the correct orientation into BamHI cut pMP3 (5). The $G_\alpha$ protein expression plasmids used in this study were constructed by replacing DNA sequences encoding the 47 carboxy-terminal amino acids of GPAL in pLP83 (12) with those of $G_{\alpha s}$ (pLP122).

Strain constructions. Yeast strains were constructed, and growth media and culture conditions formulated according to standard procedures (6). DNA-mediated transformation of yeast was carried out using the lithium acetate method. The yeast strains used as the basis for all experiments described in this report were constructed by sequential insertional deletion using recombinant alleles. Yeast strains that express human GRF receptor were constructed by sequential DNA-mediated transformation of LY296 (MATa ura3–52 trp1Δ63 his3Δ200 leu2Δ1 ade2–101 lys2–801 gpa1ΔhisG far1ΔLYS2 FUS1-HIS3 sst2ΔADE2, ref. 5) with pJH25, followed by the chimeric $G_{\alpha s}$ protein expression plasmid, pLP122 (5).

Bioassay. Functional assay of the human GRF receptor expressed in yeast was accomplished using modification of a standard procedure (5). Yeast strains were grown overnight in 2 ml synthetic complete liquid medium containing glucose (2%) and lacking uracil and tryptophan (SCD-ura-trp) medium, washed to remove residual glucose, and grown overnight in 5 ml SC Glactose (2%)-ura-trp liquid medium. Molten (55° C.) SC Glactose (2%)-ura-trp-his agar medium (30 ml, adjusted to pH 6.8 by addition of concentrated KOH or $NH_4OH$ prior to autoclaving) was inoculated with the overnight culture ($2\times10^4$ cells/ml) and plated in square (9×9 cm) petri plates. Sterile filter disks were placed on the surface of the solidified agar and saturated with 10 μl of sterile water containing the indicated amounts of the designated compounds. Plates were incubated at 30° C. for 3 days. Human GRF (hGRF (1–29)-NH$_2$), (D-ala$^2$)-hGRF (1–29)-NH$_2$, and met-enkephalin were from Bachem. Oxymetazoline, isoproterenol, and carbachol were from Sigma.

RESULTS

GRF binding to the human GRF receptor expressed in yeast. High level functional expression of the human GRF receptor in yeast was a necessary prerequisite to the development of a useful bioassay. The GRF receptor cDNA was placed under the control of the GAL1 promoter in plasmid pJH25. These constructs also confer inducible overexpression of Gal4p, the transcriptional activating protein for galactose-inducible genes, resulting in significantly elevated levels of receptor protein in crude membrane fractions compared to receptor expressed from a plasmid lacking GAL4 sequences (data not shown). The GRF receptor sequences were introduced into pJH25 without modification of the protein coding sequences. Previously; King et al. reported that replacement of the amino-terminal domain of the b$_2$-adrenergic receptor with equivalent STE2 sequence was necessary for efficient receptor expression in yeast (9). In contrast, functional expression of GRF receptor in yeast does not require addition of any yeast sequences to the amino- terminus. A chimeric Gα protein composed of the proposed amino-terminal βY-interaction domain from Gpalp and a carboxy-terminal receptor interaction domain from rat $G_{\alpha 5}$ (pLP122) under the control of the GPA1 promoter was constructed. Yeast strains that contain expressed GRF receptor and chimeric $G_\alpha$ protein were assembled by transformation of a yeast strain (LY296) modified by deletion of genes encoding components of the mating signal transduction pathway with human GRF receptor (pJH25) and chimeric Gpal-Gα$_5$ protein expression (pLP122) plasmids.

Figure 25A:
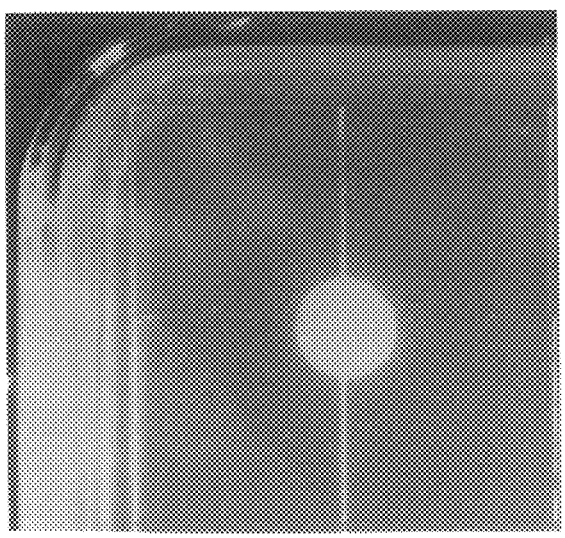
FIG. 25 (A&B). Growth of yeast in response to GRF receptor agonists. CY990 cells cultured as described in Materials and Methods were plated in SC Galactose (2%)-ura, trp, his agar medium (2×10$^4$ cells/ml). Sterile filter disks were placed on the surface of the solidified agar and saturated with 10 µl of sterile water containing 20 nmol of the indicated compounds. The plates were then incubated at 30° C. for 3 days. (A) hGRF(1–29)-NH$_2$, (B) hGRF (1–29), (D-arg$^2$)-hGRF(1–29).
Figure 25B:
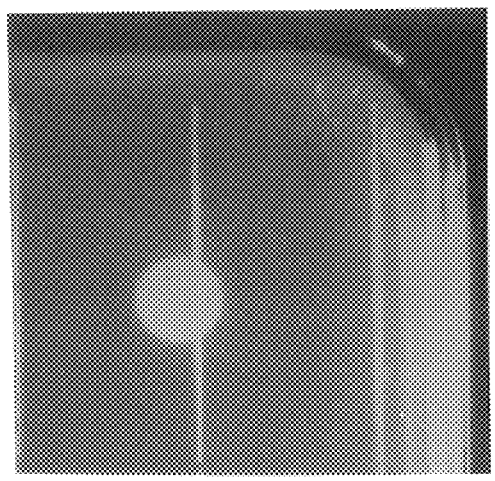

The human GRF receptor retained agonist selectivity when expressed in yeast. A selective and sensitive bioassay was designed using a yeast strain (CY990) bearing the above described genetic modifications and plasmids conferring expression of the human GRF receptor (pJH25) and a Gpal-Gα$_5$ chimeric protein (pLP122). A dose-dependent growth response of CY990 cells was evident around an agonist analog of GRF [hGRF (1–29)-NH$_2$, FIG. 25A] which was inhibited by coadministration of an antagonist analog [(D-arg$^2$)-hGRF (1–29)-NH$_2$, FIG. 25B]. The assay was selective: detectable growth responses were not observed in response to a variety of agonists selective for other G protein-coupled receptors (met-enkephalin, oxymetazoline, isoproteranol, carbachol), nor by yeast cells lacking the GRF receptor (data not shown). A detectable response was observed to 20 nmol of GRF, illustrating the sensitivity of the bioassay.

REFERENCES CITED IN THIS EXAMPLE

1. Bohlen, P. F. Esch, P. Brazeau, N. Ling, and Guillemin. 1983. Isolation and characterization of the porcine hypothalamic growth hormone releasing factor. Biochem. Biophys. Res. Comm. 116: 726–734.

2. Segre, G. V. and S. R. Goldring. 1993. Receptors for secretin, calcitonin, parathyroid hormone (PTH) /PTH-related peptide, vasoactive intestinal peptide, glucagonlike peptide 1, growth hormone releasing hormone, and glucagon belong to a newly discovered G protein linked receptor family. Trends Endo. Metab. 4: 309–314.

3. Gaylinn, B. D., J. K. Harrison, J. R. Zysk, C. E. Lyons, K. R. Lynch, and M. O. Thorner 1993. Molecular cloning and expression of a human anterior pituitary receptor for growth hormone-releasing hormone. Mol. Endocrinol. 7: 77–84.

4. Sambrook, J., E. F. Fritsch, and T. Maniatis. 1989. Molecular Cloning, A Laboratory Handbook. Cold Spring Harbor Press. Cold Spring Harbor, N.Y.

5. Price, L. A., E. M. Kajkowski, J. R. Hadcock, B. A. Ozenberger, and M. H. Pausch. 1995. Yeast cell growth in response to agonist dependent activation of a mammalian somatostatin receptor. submitted.

6. Rose, M., F. Winston, and P. Rieter. 1990. Methods in Yeast Genetics. Cold Spring Harbor Press. Cold Spring Harbor, N.Y.

7. Blumer, K. J., J. E. Reneke, and J. Thorner. 1988. The STE2 gene product is the ligand-binding component of the α-factor receptor of Saccharomyces cerevisiae. J. Biol. Chem. 263: 10836–10842.

8. Strnad, J., C. M. Eppler, M. Corbett, and J. R. Hadcock. 1993. The rat SSTR2 somatostatin receptor subtype is coupled to inhibition of cyclic AMP accumulation. Biochem. Biophys. Res. Comm. 191: 968–976.

9. King, K., E. G. Dohlman, J. Thorner, M. G. Caron, and R. J. Lefkowitz. 1990. Control of yeast mating signal transduction by a mammalian $_{β2}$-adrenergic receptor and $G_3$ α subunit. Science 250: 121–123.

10. Weiner, J. L., C. Guttierez-Steil, and K. J. Blumer. 1993. Disruption of receptor-G protein coupling in yeast promotes the function of an SST2-dependent adaptation pathway. J. Biol. Chem. 268: 8070–8077.

EXAMPLE 13

Overexpression of STE50 enhances the sensitivity of yeast bioassay.

Several molecular mechanisms for adaptation have been described for the yeast mating signal transduction pathway (1). Alterations to one or more of these mechanisms should serve to enhance the sensitivity of a bioassay by altering desensitization pathways and, therefore, prolonging the signal initiated by agonist binding to receptor. The effects of an sst2 mutation on the sensitivity of the yeast bioassay were described previously (Example 6). As an alternative to the genetic modification at sst2, overexpression of the yeast STE50 gene was predicted to have similar effects (2), although by a different mechanism of action (2, 3). The STE50 gene was isolated and placed under the control of a strong constitutive promoter in a high-copy-number plasmid resulting in significant overexpression of the gene. Yeast engineered to respond to the mammalian hormone somatostatin through an expressed SSTR2 somatostatin receptor were found to exhibit a more robust response to hormone if STE50 was overexpressed.

MATERIALS AND METHODS

Construction of STE50 expression plasmid. Growth of bacterial strains and plasmid manipulations were performed by standard methods (4). The protein coding sequences for STE50 were amplified by polymerase chain reaction (PCR) using oligonucleotides selected by examination of the published sequence (2). The sense oligonucletide (5'- GTCGA-CAAATCAG ATG GAG GAC GGT AAA CAG G -3'(SEQ. ID NO:17)) contained the translation star: codon (underlined) and a SalI restriction site and the antisense oligonucleotide (5'- GAGCTCA TTA GAG TCT TCC ACC GGG GG 3'(SEQ. ID NO:18)) contained the Translation stop codon (underlined) and a SacI restriction site. These oligonucleotides were used as primers in a standard PCR to amplify STE50 from Saccharomyces cerevisiae genomic DNA. The 1,100 basepair amplification product was cloned into the pCR2 vector (Invitrogen Corp., San Diego, Calif.) and confirmed by DNA sequencing. The STE50 sequences were then isolated on a SalI-SacI restriction fragment and cloned into a pADH expression vector (5), placing the expression of STE50 under the control of the strong constitutive ADHI promoter. This plasmid was designated pOZ162.

Yeast strain construction. Growth and transformation of yeast strains were performed as described by Rose et al. (6). The SSTR2 somatostatin receptor expression strain LY268 (MATA ura3–52 trp1Δ63 his3Δ200 leu2Δ1 ade2–101 lys2–801 gpa1ΔhisG far1ΔLYS2 FUS1-HIS3 sst2ΔADE2, pJH2 pLP82) was described in prior examples and by Price et al. (7). Strain LY268 was transformed with either the STE50 expression plasmid pOZl62 or the pADH vector. These strains are denoted CY560 or CY562, respectively.

Bioassay. Bioassay of SSTR2 somatostatin receptor expressed in yeast was described in prior examples and by Price et al. (7). Briefly, yeast strains were grown overnight in 2 ml synthetic complete liquid medium containing glucose (2%) and lacking uracil, tryptophan and leucine. (SCD-ura-trp-leu), washed to remove residual glucose, and grown overnight in 5 ml SC Glactose (2%)-ura-trp-leu liquid medium. Molten (52° C.) SC Glactose (2%)-ura-trp-leu-his agar medium (30 ml, adjusted to pH 6.8 by addition of KOH prior to autoclaving) was inoculated with 0.06 ml of the overnight culture to produce a final cell density of approximately $10^5$ cells/ml and poured in square (9×9 cm) petri plates. Sterile filter discs were placed on the surface of the solidified agar and saturated with 10 μl of sterile water containing the indicated amounts of somatostatin-14 (Bachem Bioscience Inc., Philadelphia, Pa.) or a mating pheromone (Sigma, St. Louis, Mo.). Plates were incubated at 30° C. for 3 days.

RESULTS

The effect of STE50 overexpression on the sensitivity of the yeast bioassay was examined by comparing strains differing only in the level of STE50 expression (FIG. 26). Bioassay plates were made containing either the STE50 overexpression strain CY560 or the control strain CY562. The responses of these strains to somatostatin or yeast pheromone were examined as described in Materials and Methods. Both strains had very weak responses to yeast pheromone because the wild-type yeast Gα gene, GPA1, had been disrupted and functionally replaced by a gene expressing a chimeric Gpa1/Gα$_{12}$ protein (7). This chimeric Gα protein does not efficiently interact with the yeast pheromone receptor. However, the response of these cells to somatostatin is strong (FIG. 26). As predicted, the overexpression of STE50 resulted in a more robust response (FIG. 26a). These data demonstrate that the overexpression of STE50 produces a hypersensitivity to ligands acting through G protein-coupled receptors coupled to the yeast signal transduction pathway, even if the ligand and receptor originate from a heterologous source.

REFERENCES CITED IN THIS EXAMPLE

1. Sprague G. F., Thorner J. W. Pheromone response and signal transduction during the mating process of *Saccharomyces cerevisiae*. In: The molecular and cellular biology of the yeast Saccharomyces. E. W. Jones J. R. Pringle and J. R. Broach, eds. Cold Spring Harbor Laboratory Press, 1992.

2. Ramazani-Rad M., Xu G., Hollenberg C. P. 1992 STE50, a novel gene required for activation of conjugation at an early step in mating in *Saccharomyces cerevisiae*. Mol Gen Genet 236:145–154

3. Chan R. K. , Otto C. A. 1982 Isolation and genetic analysis of *Saccharomyces cerevisiae* mutants supersensitive to G1 arrest by a factor and a factor pheromones. Mol Cell Biol 2:11–20

4. Maniatus T., Fritsch E. F., Sambrook J. Molecular cloning. Cold Spring Harbor Laboratory Press, 1982

5. Martin G. A., Viskochil D, Bollag G, et al. 1990 The GAP-related domain of the neurofibromatosis type 1 gene product interacts with ras p21. Cell 63:843–849

6. Rose M. D., Winston F., Hieter P. Methods in yeast genetics. Cold Spring Harbor Laboratory Press, 1990

7. Price L. A., Kajkowski E. N., Hadcock J. R., Ozenberger E. A., Pausch M. H. 1995 Yeast cell growth in response to agonist-dependent activation of a mammalian somatostatin receptor. Submitted.

EXAMPLE 14

Identification of Compounds with Somatostatin Receptor Agonist and/or Antagonist Properties Novel subtype-selective compounds with somatostatin agonist properties have significant therapeutic potential in the detection and treatment of various types of cancer. Compounds with somatostatin antagonist properties may be useful in promoting growth hormone release in agricultural species. Increased growth hormone release may lead to useful improvements in growth performance and carcass quality. To these ends, a yeast-based mechanism-based screening assay was developed to assay compounds for those that possessed desirable somatostatin agonist and/or antagonist properties. Bioassay. A bioassay designed to detect compounds with somatostatin agonist and/or antagonist properties was mobilized using a yeast strain (LY364 MATa ura3–52 trp1Δ63 his3Δ200 leu2Δ1 ade2–101 lys2–801 gpa1ΔhisG far1ΔLYS2 FUS1-HIS33 sst2ΔADE2, pJH2, pLPB2) that functionally expressed the rate SSTR2. The assay was accomplished using a modification of a standard procedure. Y364 was grown overnight in 2 ml synthetic complete liquid medium containing glucose (2%) and lacking uracil and tryptophan (SCD-ura-trp) medium, washed to remove residual glucose, and grown overnight in 5 ml SC Glactose (2%)-ura-trp liquid medium. Molten (55° C.) SC Glactose (2%)-ura-trp-his agar medium (150 ml, adjusted to pH 6.8 by addition of concentrated ($2\times10^4$ cells/ml) and plated in square (500 cm$^2$) petri plates For assay of antagonists, somatostatin (20 nM S-14) was added to the molten agar prior to pouring. Sterile filter disks were placed on the surface of the solidified agar and saturated with 10 μl of sterile water containing candidate compounds. Plates were incubated at 30° C. for 3 days.

Figure 27A:
FIG. 27 (A&B). Bioassay of compounds with somatostatin receptor and/or antagonist properties. IY364 cells were plated in SC Galactose (2%)-ura, trp, his agar medium (2×10$^4$ cells/ml). For assay of antagonists, somatostatin (20 nM S-14) was added to the molten agar prior to pouring. Sterile filter disks were placed on the surface of the solidified agar and saturated with 10 µl of sterile water containing test compounds. The plates were then incubated at 30° C. for 3 days (Left) Assay for somatostatin agonists. Somatostatin (S-14) was applied to positions on the bottom row, left side (6 nmol, 600 pmol, 60 pmol, 600 pmol), (Right) Assay for somatostatin antagonists. Somatostatin (S-14) was applied to positions on the bottom row, left side (6 nmol, 600 pmol, 60 pmol, 600 pmol).
Figure 27B:
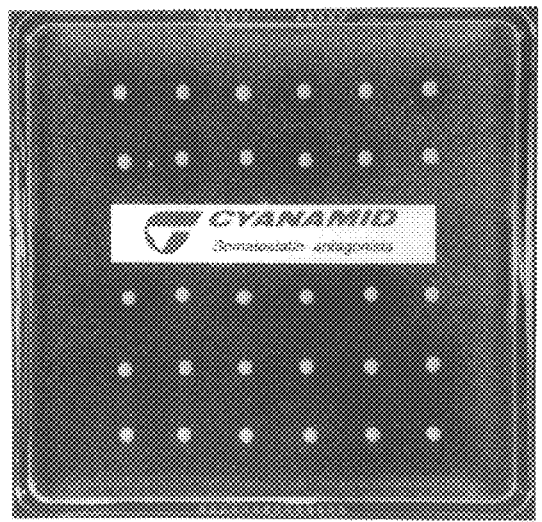

Results. Active compounds from a primary screen were reassayed and the results displayed in FIG. 27. The left hand panel displays the results of an assay for compounds with somatostatin agonist properties. Four compounds exhibited substantial growth promoting activity expected of compounds with somatostatin agonist properties. The compounds found in the bottom left four positions are varying amounts of somatostatin applied as controls. The right hand panel displays the results of an assay for compounds with somatostatin antagonist activity. In the antagonist bioassay, somatostatin is added to the molten agar prior to pouring. In this way, all cells within the plate are induced to grow in response to somatostatin. As applied active compounds with antagonist properties diffuse into the agar medium and come into contact with the cells within, the growth response induced by somatostatin is interrupted, yielding a clear zone of inhibited growth. Several compounds exhibited detectable growth inhibiting properties.

EXAMPLE 15

Fusion of STE2 sequences to the amino terminal of SSTR2 reduces signaling efficiency in response to somatostatin.

High level functional expression in yeast of G protein-coupled receptors in general, and the SSTR2 in particular, was a necessary prerequisite to the development of a useful bioassay. King et al. reported that replacement of the amino-terminal domain of the $\beta_2$-adrenergic receptor with equivalent STE2 sequence was necessary for efficient receptor expression in yeast. To test this hypothesis and the effect of STE2 sequences on expression of the somatostatin receptor in yeast, the rat SSTR2 cDNA was placed under the control of the GAL1 promoter in plasmids pJH1 and pJH2. These constructs confer inducible overexpression of Gal4p, the transcriptional activating protein for galactose-inducible genes, resulting in significantly elevated levels of receptor protein in crude membrane franctions compared to receptor expressed from a plasmid lacking GAL4 sequences (data not shown). In SSTR2 expression plasmid pJH1, DNA sequences encoding the first 13 amino acids of SSTR2 were replaced with coding sequence for the first 23 amino acids of STE2 (FIG. 11). The rate SSTR2 sequences were introduced into pJH2 without modification of the protein coding sequences. Yeast strains containing these constructs (LY322: MATa ura3–52 trp1Δ63 his3Δ200 leu2Δ1 ade2–101 lys2–801 gpa1ΔhisG far1ΔLYS2 FUSI-HIS3 sst2ΔADE2, pJHI, pLP82; LY268: MATa ura3–52 trp1Δ63 his3Δ200 ade2–101 lys2–801 gpa1ΔhisG far1ΔLYS2 FUSI-HIS3 sst2ΔADE2, pJH2, pLP82) bear a plasmid (pLp82) that confers expression of a chimeric Gα protein composed of the proposed amino-terminal βY-interaction domain from Gpalp and carboxy-terminal receptor interaction domain from rat $G_{\alpha 12}$ under the control of the GPA1 promoter. The magnitude of the response of these strains to applied somatostatin (S-14) was measured (FIG. 28). LY268 cells exhibited a robust growth response to applied S-14, demonstrating that rat SSTR2 does not require STE2 sequences to be functionally expressed in yeast (FIG. 28A) The growth response of LY268 cells was substantially greater than that exhibited by LY322 cells (FIG. 28B). The sole difference between these strains is the presence of STE2 sequences in pJH1 found in LY322. Thus, replacement of the amino terminum of SSTR2 with the equivalent segment of STE2 greatly reduces the efficiency of signalling in response to applied somatostatin. In spite of the observations of King et al., heterologous G protein-coupled receptors expressed in yeast do not require amino-terminal protein coding sequences from any yeast protein for functional expression.

What is claimed is:

1. A transformed yeast cell comprising a reporter gene under control of a pheromone-responsive promoter, a heterologous G protein coupled receptor gene, each said gene being under the control of a separate promoter, and a gene mutation causing increased sensitivity to receptor activation selected from the group consisting of sst2, STE50, sgvl, ste2, ste3, pik1, afr1, msg5, and sig1, wherein said heterologous G protein-coupled receptor gene does not include a coding sequence from a yeast G protein-coupled receptor gene fused thereto.

2. A transformed yeast cell comprising a reporter gene under control of a pheromone-responsive promoter, a heterologous G protein-coupled receptor gene, each said gene being under the control of a separate promoter, and a mutation at a gene that permits transcriptional activation of pheromone-responsive genes without cell cycle arrest, wherein said heterologous G protein-coupled receptor gene does not include a coding sequence from a yeast G protein-coupled receptor gene fused thereto.

3. The transformed yeast cell of claim 1, which further comprises a mutation at a gene that permits transcriptional activation of pheromone-responsive genes without cell cycle arrest.

4. The transformed yeast cell of claim 2, which further comprises a mutation of the cdc35 gene.

5. The transformed yeast cell of claim 4, which further comprises a heterologous adenylylcyclase.

6. The transformed yeast cell of claim 2, which further comprises a mutation in the plc1 gene.

7. The transformed yeast cell of claim 6, which further comprises a heterologous $PLC_b$.

8. The transformed yeast cell of claim 2, which further comprises a heterologous G protein-gated potassium channel wherein said yeast cell is unable to grow on low potassium media.

9. The transformed yeast cell of claim 1, wherein the reporter gene is selected from the group consisting of HIS3, G418r, URA3, LYS2, CAN1, Lacz and CYH2, and the pheromone-responsive promoter is FUS1.

10. The transformed yeast cell of claim 9, which further comprises a mutation at a FAR1 or FUS3 gene that permits transcriptional activation of pheromone-responsive genes without cell cycle arrest.

11. The transformed yeast cell of claim 9, which further comprises a mutation at a gene that permits transcriptional activation of pheromone-responsive genes without cell cycle arrest.

12. The transformed yeast cell of claim 1 or 2, herein said G protein-coupled receptor gene encodes a receptor selected from the group consisting of β2-adrenergic receptor, α2-adrenergic receptor, 5HT-1A receptor, muscarinic acetylcholine receptor, growth hormone releasing factor receptor, somatostatin receptor, cholecystokinin receptor, and adenosine receptor.

13. The transformed yeast cell of claim 1 or 2, which further comprises a heterologous Gα subunit.

14. The transformed yeast cell of claim 8, which further comprises trk1 and trk2 mutations.

15. The transformed yeast cell of claim 8, which further comprises heterologous GβY subunits.

16. The transformed yeast cell of claim 2, wherein the reporter gene is selected from the group consisting of HIS3, G418r, URA3, LYS2, CAN1, Lacz and CYH2, and the pheromone-responsive promoter is FUS1.

17. The transformed yeast cell of claim 16, which further comprises a gene mutation causing increased sensitivity to receptor activation selected from the group consisting of sst2, STE50, sgvl, ste2, ste3, pik1, afr1, msg5 and sig1.

18. The transformed yeast cell of claim 16, which further comprises a mutation in a SCGI/GPAI gene.

19. The transformed yeast cell of claim 18, which further comprises a gene mutation causing increased sensitivity to receptor activation selected from the group consisting of sst2, STE50, sgvl, ste2, ste3, pik1, afr1, msg5 and sig1.

20. The transformed yeast cell of claim 1, wherein the gene mutations causing increased sensitivity to receptor activation are sst2 and ste2 mutations.

21. The transformed yeast cell of claim 1, wherein said gene mutation causing increased sensitivity to receptor activation is selected from the group consisting of sst2, STE50, sgv1, ste2, ste3, pik1 and afr1.

22. The transformed yeast cell of claim 12, wherein said G protein-coupled receptor is selected from the group consisting of β2-adrenergic receptor, α2-adrenergic receptor, 5HTI-A receptor, muscarinic acetylcholine receptor, growth hormone releasing factor receptor, and somatostatin receptor.

23. The transformed yeast cell of claim 3, wherein said gene mutation causing increased sensitivity to receptor activation is selected from the group consisting of sst2, STE50, sgvl, ste2, ste3, pik1 and afr1.

24. The transformed yeast cell of claim 2, wherein said mutation at a gene that permits transcriptional activation of pheromone responsive genes without cell cycle arrest is chosen from the group consisting of mutations at a FAR1 or FUS3 gene.

25. The transformed yeast cell of claim 19, wherein said mutation at a gene that permits transcriptional activation of pheromone responsive genes without cell cycle arrest is chosen from the group consisting of mutations at a FAR1 or FUS3 gene.

26. The transformed yeast cell of claim 1, wherein said G protein-coupled receptor is selected from the group consisting of β2-adrenergic receptor, α2-adrenergic receptor, 5HTI-A receptor, muscarinic acetylcholine receptor, growth hormone releasing factor receptor, and somatostatin receptor.

27. The transformed yeast cell of claim 26, wherein said gene mutation causing increased sensitivity to receptor activation is selected from the group consisting of sst2, STE50, sgvl, ste2, ste3, pik1 and afri.

28. The transformed yeast cell of claim 2, wherein said G protein-coupled receptor is selected from the group consisting of β2-adrenergic receptor, α2-adrenergic receptor, 5HTI-A somatostatin receptor.

29. The transformed yeast cell of claim 28, wherein said mutation at a gene that permits transcriptional activation of pheromone responsive genes without cell cycle arrest is chosen from the group consisting of mutations at a FAR1 or FUS3 gene.

30. The transformed yeast cell of claim 17, wherein the gene mutations causing increased sensitivity to receptor activation are sst2 and ste2 mutations.

31. The transformed yeast cell of claim 17, wherein said gene mutation causing increased sensitivity to receptor activation is selected from the group consisting of sst2, STE50, sgvl, ste2, ste3, pik1 and afr1.

32. The transformed yeast cell of claim 19, wherein said gene mutation causing increased sensitivity to receptor activation is selected from the group consisting of sst2, STE50, sgvl, ste2, ste3, pik1 and afr1.

33. The transformed yeast cell of claim 9, wherein said reporter gene is selected from the group consisting of HIS3, G418r, URA3, LYS2, CAN1 and Lacz.

34. The transformed yeast cell of claim 16, wherein said reporter gene is selected from the group consisting of HIS3, G418r, URA3, LYS2, CAN1 and Lacz.

35. The transformed yeast cell of claim 16, wherein said reporter gene is selected from the group consisting of HIS3, G418r, URA3, LYS2, CAN1, and Lacz.

36. The transformed yeast cell of claim 11, wherein said reporter gene is selected from the group consisting of HIS3, G418r, URA3, LYS2, CAN1, and Lacz.

37. The transformed yeast cell of claim 17, wherein said reporter gene is selected from the group consisting of HIS3, G418r, URA3, LYS2, CAN1, and Lacz.

38. The transformed yeast cell of claim 18, wherein said reporter gene is selected from the group consisting of HIS3, G418r, URA3, LYS2, CAN1, and Lacz.

39. The transformed yeast cell of claim 19, wherein said reporter gene is selected from the group consisting of HIS3, G418r, URA3, LYS2, CAN1, and Lacz.

40. The transformed yeast cell of claim 3, wherein said mutation at a gene that permits transcriptional activation of pheromone responsive genes without cell cycle arrest is chosen from the group consisting of mutations at a FAR1 or FUS3 gene.

41. The transformed yeast cell of claim 16, wherein said mutation at a gene that permits transcriptional activation of pheromone responsive genes without cell cycle arrest is chosen from the group consisting of mutations at a FAR1 or FUS3 gene.

42. The transformed yeast cell of claim 17, wherein said mutation at a gene that permits transcriptional activation of pheromone responsive genes without cell cycle arrest is chosen from the group consisting of mutations at a FAR1 or FUS3 gene.

43. The transformed yeast cell of claim 18, wherein said mutation at a gene that permits transcriptional activation of pheromone responsive genes without cell cycle arrest is chosen from the group consisting of mutations at a FAR1 or FUS3 gene.

44. The transformed yeast cell of claim 4, wherein said mutation at a gene that permits transcriptional activation of pheromone responsive genes without cell cycle arrest is chosen from the group consisting of mutations at a FAR1 or FUS3 gene.

45. The transformed yeast cell of claim 5, wherein said mutation at a gene that permits transcriptional activation of pheromone responsive genes without cell cycle arrest is chosen from the group consisting of mutations at a FAR1 or FUS3 gene.

46. The transformed yeast cell of claim 6, wherein said mutation at a gene that permits transcriptional activation of pheromone responsive genes without cell cycle arrest is chosen from the group consisting of mutations at a FAR1 or FUS3 gene.

47. The transformed yeast cell of claim 7, wherein said mutation at a gene that permits transcriptional activation of pheromone responsive genes without cell cycle arrest is chosen from the group consisting of mutations at a FAR1 or FUS3 gene.

48. The transformed yeast cell of claim 8, wherein said mutation at a gene that permits transcriptional activation of pheromone responsive genes without cell cycle arrest is chosen from the group consisting of mutations at a FAR1 or FUS3 gene.

49. The transformed yeast cell of claim 14, wherein said mutation at a gene that permits transcriptional activation of pheromone responsive genes without cell cycle arrest is chosen from the group consisting of mutations at a FAR1 or FUS3 gene.

50. The transformed yeast cell of claim 15, wherein said mutation at a gene that permits transcriptional activation of pheromone responsive genes without cell cycle arrest is chosen from the group consisting of mutations at a FAR1 or FUS3 gene.

51. The method according to claim 13, wherein the heterologous Gα subunit is selected from the group consisting of a Gs subunit, a Gi subunit, a Go subunit, a Gz subunit, a Gq subunit, a G11 subunit, and a G16 subunit.

52. The transformed yeast cell of claim 3, wherein the gene mutations causing increased sensitivity to receptor activation are sst2 and ste2 mutations.

53. The transformed yeast cell of claim 40, wherein the gene mutations causing increased sensitivity to receptor activation are sst2 and ste2 mutations.

54. The transformed yeast cell of claim 53, wherein the mutation at a gene that permits transcriptional activation of pheromone responsive genes without cell cycle arrest is a far1 mutation.

55. The transformed yeast cell of claim 24, wherein the mutation at a gene that permits transcriptional activation of pheromone responsive genes without cell cycle arrest is a far1 mutation.

56. The transformed yeast cell of claim 40, wherein the mutation at a gene that permits transcriptional activation of pheromone responsive genes without cell cycle arrest is a far1 mutation.

57. The transformed yeast cell of claim 3, wherein the gene mutation causing increased sensitivity to receptor activation is a sst2 mutation.

58. The transformed yeast cell of claim 40, wherein the gene mutation causing increased sensitivity to receptor activation is a sst2 mutation.

59. The transformed yeast cell of claim 54, wherein the gene mutation causing increased sensitivity to receptor activation is a sst2 mutation.

60. The transformed yeast cell of claim 1, wherein the gene mutation causing increased sensitivity to receptor activation is a sst2 mutation.

61. The transformed yeast cell of claim 2, further comprising a gene mutation causing increased sensitivity to receptor activation selected from the group consisting of sst2, STE50, sgvl, ste2, ste3, pikl, afrl, msg5, and sig1.

62. The transformed yeast cell of claim 2, further comprising a gene mutation causing increased sensitivity to receptor activation selected from the group consisting of sst2, STE50, sgvl, ste2, ste3, pikl, and afr1.

63. The transformed yeast cell of claim 61, wherein the gene mutations causing increased sensitivity to receptor activation are sst2 and ste2 mutations.

64. The transformed yeast cell of claim 62, wherein the mutation causing increased sensitivity to receptor activation is a sst2 mutation.

65. The transformed yeast cell of claim 1 or 2, wherein said heterologous G protein-coupled receptor is capable of binding to endogenous yeast Gα protein.

66. The transformed yeast cell of any one of claims 1, 2, 3, 24, 40, or 55–58, 60–62, or 64, which further comprises a hybrid Ga protein, wherein the hybrid Ga protein comprises a yeast Ga protein sequence and a heterologous Ga protein sequence.

67. The transformed yeast cell of claim 66, wherein the heterologous G protein-coupled receptor is a mammalian G protein-coupled receptor.

68. The transformed yeast cell of claim 67, wherein the mammalian G protein-coupled receptor is a human G protein-coupled receptor.

69. The transformed yeast cell of any one of claims 2, 54, or 59, wherein the heterologous G protein-coupled receptor is a mammalian G protein-coupled receptor and which further comprises a hybrid Gα protein, wherein the hybrid Gα protein comprises a yeast Gα protein sequence and a mammalian Gα protein sequence.

70. The transformed yeast cell of claim 69, wherein the mammalian Gα protein sequence is a human Gα protein sequence.

* * * * *

UNITED STATES PATENT AND TRADEMARK OFFICE
CERTIFICATE OF CORRECTION

PATENT NO.      : 6,607,906 B1
DATED           : August 19, 2003
INVENTOR(S)     : Mark Henry Pausch et al.

It is certified that error appears in the above-identified patent and that said Letters Patent is hereby corrected as shown below:

Column 51,
Line 52, "5HT-lA" should read -- 5HT-1A --.
Line 59, "trkl" should read -- trk1 --.

Column 52,
Lines 2 and 8, "sgvl" should read -- sgv1 --, "pikl" should read -- pik1 --, "afrl" should read -- afr1 --, and "sigl" should read -- sig1 --.
Line 4, "SCGI/GPAI" should read -- SCG1/GPA1 --.
Line 14, "pikl and afrl" should read -- pik1 and afr1 --.
Lines 18, 38 and 48, "5HTI-A" should read -- 5HT1-A --.
Lines 24, 44, 60 and 64, "sgvl" should read -- sgv1 --, "pikl" should read -- pik1 --, and "afrl" should read -- afr1 --.

Column 54,
Line 43, "sgvl" should read -- sgv1 --, "pikl" should read -- pik1 --, "afrl" should read -- afr1 --, and "sigl" should read -- sig1 --.
Line 47, "sgvl" should read -- sgv1 --, "pikl" should read -- pik1 --, and "afrl" should read -- afr1 --.
Lines 58-59, "1, 2, 3, 24, 40, or 55-58, 60-62, or 64" should read
-- 1, 2, 3, 20, 24, 40, or 52-64 --.
Lines 59-60, (all occurrences), "Ga" should read -- Gα --.

Column 2,
Line 2, both occurrences of "Ga" should read -- Gα --.

Signed and Sealed this

Second Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,607,906 B1
DATED : August 19, 2003
INVENTOR(S) : Mark Henry Pausch et al.

It is certified that error appears in the above-identified patent and that said Letters Patent is hereby corrected as shown below:

<u>Column 56,</u>
Line 2, both occurrences of "Ga" should read -- Gα --.

Signed and Sealed this

Ninth Day of November, 2004

JON W. DUDAS
*Director of the United States Patent and Trademark Office*